(12) United States Patent
Szpirer et al.

(10) Patent No.: US 10,718,001 B2
(45) Date of Patent: Jul. 21, 2020

(54) HOST CELL FOR PRODUCING PROTEINS

(71) Applicant: DELPHI GENETICS, Charleroi (Gosselies) (BE)

(72) Inventors: Cedric Szpirer, Fleurus (BE); Jonathan Cavrenne, Gembloux (BE); Benjamin Michel, Liege (BE)

(73) Assignee: DELPHI GENETICS, Charleroi (Gosselies) (BE)

( * ) Notice: Subject to any disclaimer, the term of this patent is extended or adjusted under 35 U.S.C. 154(b) by 0 days.

(21) Appl. No.: 15/329,087

(22) PCT Filed: Jul. 24, 2015

(86) PCT No.: PCT/EP2015/067036
§ 371 (c)(1),
(2) Date: Jan. 25, 2017

(87) PCT Pub. No.: WO2016/012607
PCT Pub. Date: Jan. 28, 2016

(65) Prior Publication Data
US 2017/0211118 A1 Jul. 27, 2017

(30) Foreign Application Priority Data
Jul. 25, 2014 (EP) .................... 14178656
Aug. 26, 2014 (EP) .................... 14182341

(51) Int. Cl.
*C12N 15/00* (2006.01)
*C12P 21/02* (2006.01)
*C12N 15/65* (2006.01)

(52) U.S. Cl.
CPC .............. *C12P 21/02* (2013.01); *C12N 15/65* (2013.01); *C12Y 207/07006* (2013.01)

(58) Field of Classification Search
None
See application file for complete search history.

(56) References Cited

U.S. PATENT DOCUMENTS

| 4,952,496 | A | 8/1990 | Studier et al. | |
|---|---|---|---|---|
| 8,318,497 | B2 * | 11/2012 | Szpirer | C12N 15/10 435/252.3 |
| 8,470,580 | B2 | 6/2013 | Gabant et al. | |
| 9,555,127 | B2 * | 1/2017 | Cueva-Mendez | A61K 38/164 |
| 2003/0017600 | A1 * | 1/2003 | Gabant | C12N 15/65 435/472 |
| 2004/0115811 | A1 * | 6/2004 | Gabant | C07K 14/245 435/455 |
| 2010/0003738 | A1 * | 1/2010 | Thomas | C12N 15/63 435/252.3 |
| 2013/0011898 | A1 * | 1/2013 | Szpirer | C12N 7/00 435/170 |
| 2014/0147890 | A1 * | 5/2014 | Szpirer | C12N 7/00 435/69.1 |

FOREIGN PATENT DOCUMENTS

| JP | 2003-532381 A | 11/2003 |
|---|---|---|
| JP | 2005-522196 A | 7/2005 |
| JP | 2010-187541 A | 9/2010 |
| JP | 2010-246532 A | 11/2010 |
| WO | 1999058652 | 11/1999 |
| WO | 2001004288 | 1/2001 |
| WO | 01/46444 A1 | 6/2001 |
| WO | 03/078638 A1 | 9/2003 |
| WO | 2010007246 | 1/2010 |
| WO | 2010135742 | 11/2010 |
| WO | 2013004817 | 1/2013 |
| WO | 2003/037504 A1 | 3/2013 |
| WO | 2013/161958 A1 | 10/2013 |

OTHER PUBLICATIONS

Score report Bernard (Year: 1994).*
Score report Thomas (Year: 2009).*
Andersen et al., "Production technologies for monoclonal antibodies and their fragments", Current Opinion in Biotechnology, Oct. 2004;15(5):456-62.
Bernard et al., "Cell Killing by the F Plasmid CcdB Protein Involves Poisoning of DNA-Topoisomerase II Complexes", J. Mol. Biol. Aug. 5, 1992;226(3):735-745.
Datsenko et al., "One-step inactivation of chromosomal genes in *Escherichia coli* K-12 using PCR products", Proc. Natl. Acad. Sci. USA, Jun. 6, 2000; vol. 97, No. 12 6640-6645.
Guglielmini et al., "Automated discovery and phylogenetic analysis of new toxin-antitoxin systems", BMC Microbiology, Jun. 25, 2008;8:104.
Guzman et al., "Tight Regulation, Modulation, and High-Level Expression by Vectors Containing the Arabinose PBAD Promoter", Journal of Bacteriology, Jul. 1995, vol. 177, No. 14:4121-4130.
Henrich et al., "Use of the lysis gene of bacteriophage phi X174 for the construction of a positive selection vector", Gene. 1986;42(3):345-349.
Holliger et al., "Engineered antibody fragments and the rise of single domains", Nature Biotechnology, Sep. 2005; vol. 23 No. 9:1126-36.
Jeong et al., "Constitutive production of human leptin by fed-batch culture of recombinant rpoS-*Escherichia coli*", Protein Expression and Purification, Jul. 2004;36(1):150-156.
Makrides, "Strategies for Achieving High-Level Expression of Genes in *Escherichia coli*", Microbiological Reviews. Sep. 1996;60(3):512-538.
Novagen, "λDE3 Lysogenization Kit". User Protocol TB031, Rev. C 0805, 2005.

(Continued)

*Primary Examiner* — Catherine S Hibbert
(74) *Attorney, Agent, or Firm* — Young & Thompson

(57) ABSTRACT

Disclosed is a host cell for producing a recombinant peptide, polypeptide or protein of interest, wherein the host cell includes at least 2 copies of a nucleic acid sequence encoding a poison protein; and to the use thereof for producing peptides, polypeptides or proteins of interest.

15 Claims, 9 Drawing Sheets
Specification includes a Sequence Listing.

(56) References Cited

OTHER PUBLICATIONS

Peubez et al., "Antibiotic-free selection in *E. coli*: new considerations for optimal design and improved production", Microbial Cell Factories, Sep. 7, 2010;9:65.
Pierce et al., "A positive selection vector for cloning high molecular weight DNA by the bacteriophage P1 system: Improved cloning efficacy", Proc. Natl. Acad. Sci. USA. Mar. 15, 1992;89(6):2056-2060.
Poo et al., "Novel high-level constitutive expression system, pHCE vector, for a convenient and cost-effective soluble production of human tumor necrosis factor-α", Biotech. Lett. 2002;24:1185-1189.
Schlieper et al., "A positive selection vector for cloning of long polymerase chain reaction fragments based on a lethal mutant of the crp gene of *Escherichia coli*", Analytical Biochemistry Mar. 15, 1998;257(2):203-209.
Sodoyer et al., (2012). "Antibiotic-free selection for bio-production: moving towards a new gold standard", In Pana (Ed.), InTech, "Antibiotic resistant bacteria—A continuous challenge in the new millennium".
Stieber et al., "The art of selective killing: plasmid toxin/antitoxin systems and their technological applications", Biotechniques. Sep. 2008;45(3):344-346.
Studier et al., "Use of bacteriophage T7 RNA polymerase to direct selective high-level expression of cloned genes", J. Mol. Biol. May 5, 1986;189(1):113-130.
Szpirer et al., "Interaction between the RP4 coupling protein TraG and the pBHR1 mobilization protein Mob". Mol. Microbiol. Sep. 2000;37(6):1283-1292.
Szpirer et al., "Separate-component-stabilization system for protein and DNA production without the use of antibiotics". Biotechniques. May 2005;38(5):775-781.
Trudel et al., "pGATA: A Positive Selection Vector Based on the Toxicity of the Transcription Factor GATA-1 to Bacteria", Biotechniques. Apr. 1996;20(4):684-93.
Unterholzner et al., "Toxin-antitoxin systems: Biology, identification, and application", Mobile Genetic Elements. Sep. 1, 2013;3(5):e26219.
Warming et al., "Simple and highly efficient BAC recombineering using galK selection", Nucleic Acids Research, Feb. 24, 2005;33(4):e36.
Zielenkiewicz et al., "Mechanisms of plasmid stable maintenance with special focus on plasmid addiction systems", Acta Biochimica Polonica 2001;48(4):1003-1023.
European Search Report dated Jan. 23, 2015; Application No. EP14178656.
International Search Report PCT/EP2015/067036 dated Sep. 28, 2015.
Reschner et al., "Use of Staby(®) technology for development and production of DNA vaccines free of antibiotic resistance gene", Human Vaccines and Immunotherapeutics, Oct. 2013;9(10):1-8.

* cited by examiner

HOST CELL FOR PRODUCING PROTEINS

FIELD OF INVENTION

The present invention relates to heterologous systems for recombinant protein production. In particular, the present invention relates to host cells for use in methods for producing proteins based on an improved poison-antidote system.

BACKGROUND OF INVENTION

Microorganisms are today widely used for protein or DNA production. Usually, these processes require the use of bacterial plasmids as vectors carrying the gene to be expressed. However, plasmid maintenance within microorganisms is limited, and plasmid instability thus represents a significant concern in recombinant protein production or in DNA production.

It has been demonstrated that the growth rate of plasmid-bearing cells is significantly reduced relative to that of a plasmid-free cell. One theory is that plasmid replication and transcription, as well as protein production, represent a significant burden on cellular metabolism. Hence, in a fermentation process, cells losing the plasmid exhibit a higher fitness than cells still bearing the plasmid, and the former rapidly overcome the latter in the bacterial population.

In order to limit plasmid loss in a cell population, and to avoid plasmid-free cells to survive and dominate the culture, selectable markers were inserted in plasmids.

The most common selectable markers used in fermentation procedures are antibiotic-resistance genes. However, contamination of the product or biomass by antibiotics (or genes encoding an antibiotic resistance) is unacceptable from a medical or regulatory perspective. Moreover, antibiotic-resistance genes may propagate in the environment, or be transferred to pathogenic strains. Moreover, recent studies demonstrated that using antibiotic-resistance genes for producing a recombinant protein strongly reduces the yield of protein production (Peubez et al., Microbial Cell factories, 2010, 9:65).

There is thus a need for other systems allowing plasmid maintenance, and free from drawbacks of antibiotic-resistance genes.

An alternative to the use of antibiotic-resistance genes is the complementation of an essential mutated chromosomal gene by a wild-type allele inserted into the plasmid. For example, systems were developed in which the mutant host is unable to synthesize an essential amino acid without a plasmid carrying out the gene that provides this function. However, this approach seriously restricts the possible choices in growth medium.

Another strategy developed is a system in which a plasmid-mediated repressor titration overcomes the repression of an essential chromosomal gene placed under the control of the lac operator. However, this procedure has the following limitations: (i) it makes the Lac promoter unavailable for other purposes such as protein expression, (ii) the system is limited to E. coli or other bacteria wherein the Lac promoter is functional, and (iii) medium containing lactose has to be avoided.

Another alternative system to the use of antibiotic-resistance genes is based on couples of poison proteins (i.e. molecules which are toxic for the host cell) combined to their antidotes. For example, the poison gene may be expressed by the host cell from a chromosomal copy, while the antidote is carried by the plasmid. Therefore, presence of the plasmid is required for the host cell survival. An example of couple poison/antidote is the ccdA (antidote)/ccdB (poison) system. CcdA and CcdB are the antidote and toxin proteins encoded by the E. coli F plasmid. Together, they ensure the death of daughter cells that do not receive a copy of F. Expression of the ccdB protein interferes with the rejoining step of DNA gyrase, causing the host cell chromosome to be cut to pieces. Other examples of antidote/poison couples include, but are not limited to, Kis/Kid proteins, Phd/Doc proteins, RelB/relE proteins, PasB (or PasC)/PasA proteins, mazF/maze proteins.

This antidote/poison system has been extensively used in cloning methods, as described for example in the U.S. Pat. No. 8,470,580: a host cell comprising the gene encoding a poison is used in combination with a plasmid comprising the gene encoding the corresponding antidote. This system thus allows the direct selection of cells having integrated a gene of interest, as only cells expressing the antidote gene survive.

This system is also used for protein production, as previously described by the inventors (Szpirer and Milinkovitch, BioTechniques, 2005, 38(5):775-781). Unexpectedly, an increase of three to five-fold of the recombinant protein production level was observed, demonstrating the great potential of this system for producing recombinant proteins.

However, the Inventors observed that, when this system is used for producing toxic proteins, some drawbacks may appear, such as, for example, mutations within the gene of interest, mutations in the antidote/poison system and the like. Willing to develop an improved plasmid stabilization system, they modified the classic system comprising one copy of the antidote gene combined with one copy of the poison gene. Surprisingly and unexpectedly, they showed that the insertion of an additional copy of the poison gene in the genome of the host cell increases the stability of the plasmid, but also increases the yield of protein production (in a non-correlate manner).

SUMMARY

The present invention thus relates to a host cell for producing a recombinant peptide, polypeptide or protein of interest, wherein said host cell comprises at least 2 copies of a nucleic acid sequence encoding a poison protein. In one embodiment, said at least 2 copies are in a different replicon than a nucleic acid sequence encoding the antidote protein to the poison protein In one embodiment, said poison protein is CcdB, encoded by SEQ ID NO: 1 or any nucleic acid sequence having at least 75% identity with SEQ ID NO: 1.

In one embodiment, the host cell further comprises at least one copy of a nucleic acid sequence encoding the antidote protein to the poison protein. In one embodiment, said antidote protein is CcdA, encoded by SEQ ID NO: 13 or any nucleic acid sequence having at least 75% identity with SEQ ID NO: 13.

In one embodiment, the nucleic acid sequence encoding the antidote protein is carried by a plasmid further comprising an expression system wherein the nucleic acid sequence encoding a recombinant peptide, polypeptide or protein of interest is or may be inserted. In one embodiment, said expression system comprises a promoter selected from the group comprising a T7 promoter, Ptrc, Para and Plac. In another embodiment, said expression system comprises a T7 promoter and the host cell further comprises a T7 RNA polymerase gene, preferably inserted in its genome, more preferably in a T7 expression system. In another embodiment, the expression system comprises a T7 promoter and the host cell further comprises a genetically modified phage inserted within its genome, preferably said phage is defined as a phage wherein:

a T7 expression system is inserted,
the S, R, and/or the Q genes are inactivated, and
the Int and/or Xis gene are inactivated.

In one embodiment, the host cell is a bacterium, preferably a gram negative bacterium, more preferably an Enterobacteriacea, and even more preferably *E. coli*. In one embodiment, the host cell of the invention further comprises inactivation of at least one of the genes tonA, galK, araB, araA, lon, ompT, rcsA, hsdR, mrr, endA and recA. In one embodiment, the host cell of the invention further comprises at least one additional copy of the gyrA gene.

The present invention also relates to a kit comprising a host cell as described hereinabove and a vector comprising at least one copy of the nucleic acid sequence encoding the antidote protein and at least one copy of an expression system wherein the nucleic acid sequence encoding a recombinant peptide, polypeptide or protein of interest is or may be inserted. In one embodiment, the nucleic acid sequence encoding a peptide, polypeptide or protein of interest is under the control of a promoter selected from the group comprising a T7 promoter, Ptrc, Para and Plac.

Another object of the invention is a method for producing a recombinant peptide, polypeptide or protein of interest, wherein said method comprises cultivating the host cell as described hereinabove and recovering the peptide, polypeptide or protein of interest.

In one embodiment, the recombinant protein is a secreted protein, a transmembrane protein or a protein which is toxic for the bacterial strain.

Definitions

In the present invention, the following terms have the following meanings:

As used herein, a "peptide" refers to a linear polymer of amino acids of less than 50 amino acids linked together by peptide bonds; a "polypeptide" refers to a linear polymer of at least 50 amino acids linked together by peptide bonds; and a protein specifically refers to a functional entity formed of one or more peptides or polypeptides, and optionally of non-polypeptides cofactors.

"Recombinant peptide, polypeptide or protein" refers to a peptide, polypeptide or protein generated from recombinant DNA, i.e. from DNA artificially inserted in a producing host cell.

"Poison protein" refers to a protein which is toxic for the host cell producing it. As used herein, a poison protein is thus toxic for the host cell of the invention.

DETAILED DESCRIPTION

The present invention relates to a host cell for producing recombinant peptides, polypeptides or proteins, wherein said host cell comprises at least two copies of a nucleic acid sequence encoding a poison protein. In one embodiment, the host cell comprises 2 copies of the nucleic acid sequence encoding the poison protein, or 3, 4, 5 or 6 copies (or more) of this nucleic acid sequence.

Examples of poison proteins include, but are not limited to, CcdB, Kid, Doc, RelE, PasA, MazE or any other poison molecule such as for example bacteriocins which is or is not of plasmid origin. The poison protein can also be a toxin protein being naturally or artificially toxic and affecting one or more vital functions of a (prokaryote) cell. The protein encoded by the gene sacB (from Bacillus amyloliquefaciens), the protein GpE, the protein GATA-1 and the protein Crp are other examples of such toxic molecules. The gene sacB encodes a levan sucrase which catalyses the hydrolysis of sucrose into products which are toxic for *E. Coli* (Pierce et al. Proc. Natl. Acad. Sci., Vol. 89, N[deg.]6 (1992) p. 2056-2060). The protein GpE is encoded by the E genes from the bacteriophage [phi]X174 which includes six unique restriction sites. GpE causes lysis of *E. Coli* cell (Heinrich et al., Gene, Vol. 42(3) (1986) p. 345-349). The protein GATA-1 has been described by Trudel et al. (Biotechniques 1996, Vol. 20(4), p. 684-693). The protein Crp has been described by Schlieper et al. (Anal. Biochem. 1998, Vol. 257(2), p. 203-209).

Preferably, the host cell of the invention comprises at least two, preferably 2, copies of a nucleic acid sequence encoding the protein CcdB. In one embodiment, the nucleic acid sequence encoding the protein CcdB is the ccdB gene (sequence SEQ ID NO: 1) or any sequence encoding a functional CcdB protein having at least 75%, preferably at least 80, 85, 90, 91, 92, 93, 94, 95, 96, 97, 98, 99% or more identity with SEQ ID NO: 1.

In one embodiment, the at least 2 copies of a nucleic acid sequence encoding a poison protein (preferably CcdB) have not 100% identity (for example have about 30%, preferably about 35, 40, 45, 50, 55, 60, 65, 70, 75, 80, 85, 90, 91, 92, 93, 94, 95, 96, 97, 98, 99% or more identity), in order to avoid recombination events between 2 copies.

In one embodiment, the at least 2 copies of a nucleic acid sequence encoding a poison protein (preferably CcdB) are from different origins (for example are from at least 2 bacterial species) or the first one is of plasmid origin and the second one is of chromosomal origin. For example, the first copy of CcdB may be from *E. coli* O157:H7 and the second copy of CcdB may be from the F plasmid.

In one embodiment, the at least two poison proteins are 100% identical, but are encoded by nucleic acid sequences that do not have 100% identity (i.e. the nucleic acid sequences differ by non-coding differences, such as, for example, a codon encoding a given amino acid is replaced by another codon encoding the same amino acid).

In one embodiment, the at least two poison proteins are not 100% identical (for example have about 30%, preferably about 35, 40, 45, 50, 55, 60, 65, 70, 75, 80, 85, 90, 91, 92, 93, 94, 95, 96, 97, 98, 99% or more identity), but their effect may be counteracted by the same antidote.

In one embodiment, the at least 2 copies of a nucleic acid sequence encoding a poison protein (preferably CcdB) have not 100% identity, but both contain conserved putative domains according to in silico analysis, using for example, the program TAQ V1.0 described in Guglielmini et al. (BMC Microbiology 2008, 8:104). In one embodiment, the second copy of a nucleic acid sequence encoding a poison protein is a putative poison protein related to the first one and identified using the program TAQ V1.0. In one embodiment, the first copy of a nucleic acid sequence encoding a poison protein is CcdB, and the second copy is selected among the 22 CcdB in silica inferred toxins identified using the program TAQ V1.0 by Guglielmini et al., 2008.

In one embodiment of the invention, the at least two copies of a nucleic acid sequence encoding a poison protein (preferably CcdB) are on a different replicon than the nucleic acid sequence encoding the corresponding antidote protein, i.e. on a replicon that does not comprise a nucleic acid sequence encoding the corresponding antidote protein. In particular, according to this embodiment, host cells comprising at least two copies of the plasmid F (plasmid F comprises a replicon comprising both a nucleic acid sequence encoding the poison protein and a nucleic acid sequence encoding the antidote protein) are not part of the present invention.

In one embodiment, the at least two copies of a nucleic acid sequence encoding a poison protein (preferably CcdB) are on the same replicon. In another embodiment, the at least two copies of a nucleic acid sequence encoding a poison protein (preferably CcdB) are on at least two distinct replicons.

In one embodiment, at least one of the at least two copies of a nucleic acid sequence encoding a poison protein (preferably CcdB) is on a plasmid. In another embodiment, the at least two copies of a nucleic acid sequence encoding a poison protein (preferably CcdB) are on a plasmid.

In one embodiment of the invention, the at least two copies of a nucleic acid sequence encoding a poison protein (preferably CcdB) are chromosomal, i.e. are inserted within the genome of the host cell.

In one embodiment of the invention, when two copies of the nucleic acid sequence encoding a poison protein are inserted within the genome of the host cell, each stands at an opposite side on the chromosome of the host cell. Preferably, each copy is inserted in a non-coding region of the chromosome of the host cell or in a gene to be inactivated.

For example, a first copy of a nucleic acid sequence encoding a poison protein is inserted in the dcm gene, and a second copy of a nucleic acid sequence encoding a poison protein is inserted between the yjjK and slt genes, i.e. at the opposite side of the *E. coli* chromosome, in an intergenic non-coding space.

The term "identity" or "identical", when used in a relationship between the sequences of two or more nucleic acid sequences or polypeptides, refers to the degree of sequence relatedness between nucleic acid sequences or polypeptides (respectively), as determined by the number of matches between strings of two or more nucleic acid residues or amino acid residues (respectively). "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics 5 and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988). Preferred methods for determining identity are designed to give the largest match between the sequences tested. Methods of determining identity are described in publicly available computer programs. Preferred computer program methods for determining identity between two sequences include the GCG program package, including GAP (Devereux et al., Nucl. Acid. Res. \2, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well-known Smith Waterman algorithm may also be used to determine identity.

Preferably, the nucleic acid sequence encoding the poison protein is under the control of the native promoter. For example, the nucleic acid sequence encoding the protein CcdB, may be fused downstream to the ccd promoter. Therefore, in the presence of the antidote, the ccd promoter is strongly repressed.

In an embodiment, the host cell is a microorganism, preferably a prokaryote, more preferably a bacterium, and even more preferably a gram negative bacterium. Advantageously, the host cell is a bacterium from the Enterobacteriacea family according to the current applicable taxonomy. Should the taxonomy change, the skilled artisan knows how to adapt the changes in the taxonomy to deduce the strains that could be used in the present invention. Examples of bacteria from the Enterobacteriacea family include, but are not limited to, bacteria belonging to the genera *Escherichia, Enterobacter, Erwinia, Klebsiella, Pantoea, Photorhabdus, Providencia, Salmonella, Serratia, Shigella, Morganella* and *Yersinia*. According to a preferred embodiment, the host cell belongs to the *Escherichia* genus, and more preferably the host cell is *Escherichia coli* (*E. coli*). Examples of strains of *E. coli* which could be used in the present invention include, but are not limited to, strains derived from *E. coli* K-12, *E. coli* B or *E. coli* W, such as, for example, MG1655, W3110, DG1, DG2, Top10, DH10B, DH5alpha, HMS174, BL21, BL21(DE3), HMS174(DE3), BL21(DE3) pLysS and BL21(DE3) pLysE.

In one embodiment, genes of the host cells may be inactivated.

As used herein, the term "inactivated" refers to the interruption or to the suppression of the expression of a gene at transcriptional or translational levels. Preferably, the term "inactivated" refers to a gene whose transcription is suppressed. According to the invention, the inactivation of a gene may be due to the mutation of the gene or to the insertion of an expression system within the coding sequence of the gene. In the meaning of the present invention, the term "mutation" refers to a stable change in the genetic sequence. Examples of mutation which could lead to the inactivation of a gene in the present invention include, but are not limited to, point mutations, insertions, deletions and amplification or gene duplication. Preferably, the mutation is a deletion. The term "deletion" as used herein means the loss or absence of a gene, preferably the total loss or absence of a gene. More preferably, the deletion starts at or before the start codon of the deleted gene, and ends at or after the stop codon of the deleted gene.

In one embodiment, the gene tonA (also known as fhuA, SEQ ID NO: 2) is inactivated. The TonA/FhuA protein is a receptor for the phages T1, T5 and Phi80.

In one embodiment, the gene galK (SEQ ID NO: 3) is inactivated. The deletion of this gene allows the use of the galK positive/negative selection for deletion of genes by a method based on homologous recombination.

In one embodiment, the gene araB (SEQ ID NO: 4) is inactivated. In another embodiment, the gene araA (SEQ ID NO: 5) is inactivated. The inactivation of araB and/or araA is recommended for the use of the Para promoter (inducible by arabinose) within the host cell.

In one embodiment, the gene lon (SEQ ID NO: 6) and/or the gene ompT (SEQ ID NO: 7) are inactivated. The Lon protein is an ATP dependent protease. The OmpT protein is an outer membrane protease. Preferably, the genes lon and ompT are inactivated.

In one embodiment, the gene rcsA (SEQ ID NO: 8) is inactivated. The protein RcsA is a positive regulator of the synthesis of the capsule, which is degraded by the Lon protease.

In one embodiment, the gene hsdR (SEQ ID NO: 9) and/or the gene mrr (SEQ ID NO: 10) are inactivated. The HsdR and Mrr proteins are restriction enzymes with different specificity. Preferably, the genes hsdR and mrr are both inactivated.

In one embodiment, the gene endA (SEQ ID NO: 11) and/or the gene recA (SEQ ID NO: 12) are inactivated. EndA is a DNA specific endonuclease. RecA is a recombination protein with protease and nuclease activity. Preferably, the genes endA and recA are both inactivated.

In one embodiment of the invention, at least one of the genes tonA, galK, araB, araA, lon, ompT, rcsA, hsdR, mrr, endA and recA are inactivated. Preferably, the inactivated genes are deleted.

In a preferred embodiment, the genes tonA, galK, araB, lon, ompT, rcsA, hsdR, mrr, endA and recA are inactivated. Preferably, the genes tonA, galK, araB, lon, ompT, rcsA, hsdR, mrr, endA and recA are deleted.

In one embodiment, the host cell of the invention comprises at least one additional copy of the nucleic acid sequence encoding the target of the poison protein. In one embodiment, the host cell comprises 2 copies of the nucleic acid sequence encoding the target of the poison protein, or 3, 4, 5 or 6 copies (or more) of this nucleic acid sequence. Preferably, said at least one additional copy is chromosomal, i.e. is inserted within the genome of the host cell.

In one embodiment where the poison protein is CcdB, the host cell of the invention may comprise at least one additional copy of the nucleic acid sequence encoding the protein GyrA.

In one embodiment, the nucleic acid sequence encoding the protein GyrA is the gyrA gene (sequence SEQ ID NO: 15) or any sequence encoding a functional GyrA protein having at least 75%, preferably at least 80, 85, 90, 91, 92, 93, 94, 95, 96, 97, 98, 99% or more identity with SEQ ID NO: 15.

In one embodiment, the second copy of the nucleic acid sequence encoding the target protein of the poison protein is inserted in the chromosome of the host cell at the same location that a copy of the nucleic acid sequence encoding the poison protein. In one embodiment, the second copy of the nucleic acid sequence encoding the target protein of the poison protein is inserted concomitantly to a copy of the nucleic acid sequence encoding the poison protein.

In one embodiment, the host cell of the invention comprises at least one copy of a nucleic acid sequence encoding the antidote protein counteracting the effects of the poison protein expressed by the host cell of the invention.

Examples of antidote proteins include, but are not limited to, CcdA (antidote of CcdB), Kis (antidote of Kid), Phd (antidote of Doc), RelB (antidote of RelE), PasB (or PasC) (antidote of PasA), MazF (antidote of MazE) or immunity molecules (antidotes of bacteriocins). The antidote protein to a toxic molecule is any protein able to reduce or suppress the effect of the corresponding toxic molecule on a cell (preferably a prokaryotic cell), when said toxic molecule is produced by said cell.

According to a preferred embodiment, the poison protein is CcdB and the host cell comprises at least one copy of a nucleic acid sequence encoding CcdA. In one embodiment, the nucleic acid sequence encoding the protein CcdA is the ccdA gene (sequence SEQ ID NO: 13) or any sequence encoding a functional CcdA protein having at least 75%, preferably at least 80, 85, 90, 91, 92, 93, 94, 95, 96, 97, 98, 99% or more identity with SEQ ID NO: 13. As used herein, a "functional" CcdA protein relates to a protein having at least 75% identity with SEQ ID NO: 13 and retaining the ability of CcdA to reduce or suppress the effect of CcdB on a cell.

In one embodiment, the nucleotide sequence encoding the antidote protein is carried by a vector, such as, for example, a plasmid, a bacteriophage, a virus, a cationic vesicle or any other type of vector, preferably by a plasmid. Therefore, the skilled artisan may easily deduce that the number of copies of the nucleic acid sequence encoding the antidote protein depend on the type of plasmid used. For example, a plasmid of the pBR322 family is usually present in a cell in a number of copies ranging from about 1 to about 100, preferably from about 20 to about 50; while a plasmid of the pUC family is usually present in a cell in a number of copies ranging from about 100 to about 500, preferably from about 150 to about 200. However, the skilled artisan may also easily deduce that the number of copies of a plasmid within a host cell may also depend on the replication rate and/or on the growth of the host cell.

In a preferred embodiment, the host cell of the invention thus further comprises at least one copy of a vector, preferably a plasmid, carrying (1) a nucleic acid sequence encoding the antidote to the poison protein, and (2) a nucleic acid sequence encoding the recombinant peptide, polypeptide or protein of interest to be produced or an insertion site for inserting the nucleic acid sequence encoding the recombinant peptide, polypeptide or protein of interest to be produced.

In one embodiment, the nucleic acid sequence encoding the recombinant peptide, polypeptide or protein of interest is comprised within an expression system; or the insertion site is such that, when inserted, the nucleic acid sequence encoding the recombinant peptide, polypeptide or protein of interest is comprised within an expression system. In particular, the nucleic acid sequence encoding the recombinant peptide, polypeptide or protein of interest is placed, or will be placed after insertion, under the control of a promoter.

As used herein, an "expression system" refers to a linear or a circular DNA molecule composed of a fragment encoding the nucleic acid sequence encoding the recombinant peptide, polypeptide or protein of interest operably linked to an additional fragment for the transcription of the system.

The additional fragment includes a promoter and a stop codon sequence. The expression system may further contain one or more origins of replication, one or more selection markers and a sequence encoding a ribosome binding site.

"Operably linked" means that fragments are arranged to be functioning as they are supposed to be, for example once transcription starts at the promoter, it goes through coded fragment to stop codon.

"Promoter" in the meaning of the present invention is an expression control element that permits binding of RNA polymerase and the initiation of transcription.

In one embodiment of the invention, the nucleic acid sequence is under the control of a "strong" promoter. A strong promoter is characterized by a high binding affinity of the promoter sequence to an RNA polymerase, usually the naturally occurring corresponding RNA polymerase, on the one hand and by a high rate of formation of mRNA by that RNA polymerase on the other hand.

In a preferred embodiment, the nucleic acid sequence is under the control of an "inducible promoter". An "inducible promoter" is a promoter that may be regulated by external factors, e.g. the presence of an inductor (also termed "inducer") molecule or the absence of a repressor molecule, or physical factors like increased or decreased temperature, osmolarity, or pH value. Different promoters and the respective induction principles were reviewed by Makrides et al. (Microbiological Reviews, 1996, (60)3: 512-538). Examples of inducible promoters which may be used in the present invention include, but are not limited to, the tac or the trc promoter, the lac or the lacUV5 promoter (all inducible by lactose or its analog IPTG (isopropylthiol-β-D-galactoside)), the tightly regulatable araBAD promoter (Para; Guzman et al., 1995, inducible by arabinose), the trp promoter (inducible by ß-indole acrylic acid addition or tryptophan starvation, repressible by tryptophan addition), the lambda promoter pL (λ) (induction by an increase of temperature), the phoA promoter (inducible by phosphate starvation), the PprpB (induction with propionate) or other promoters suitable for recombinant peptide, polypeptide or protein expression, which all use E. coli RNA polymerase.

Among inducible promoters are those that show a "leaky" expression behavior. Such promoters (so-called "leaky promoters") are, in principle, inducible, but show nevertheless also basal expression without being externally induced. Inducible promoters that show leaky expression under non-induced conditions may behave similarly to constitutive promoters (i.e. they are steadily and continuously active or they may be activated or enhanced as a result of certain cultivation conditions). Leaky promoters may be particularly useful for continuously operated cultivation processes. Examples of leaky promoters are the T7 promoter and the trp promoter. In the meaning of the present invention, the term "T7 promoter" includes promoters that are present in the genome of bacteriophage T7, as well as consensus sequences and variants of such promoters with the ability to mediate transcription by the T7 RNA polymerase. The bacteriophage T7 contains seventeen different promoter sequences, all of which comprise a highly conserved nucleotide sequence.

In one embodiment of the invention, the promoter may also be constitutive, i.e. a promoter which controls expression without the need for induction on the one hand, or the possibility of repression on the other hand. Hence, there is continuous and steady expression at a certain level. As an example, the strong constitutive HCD promoter (Poo et al., Biotechnology Letters, 2002, 24:1185-1189; Jeong et al., Protein expression and purification, 2004, 36:150-156) may be applied for constitutive expression.

Advantageously, the expression of the peptide, polypeptide or protein of interest is induced in particular conditions, such as, for example, under selection.

According to a preferred embodiment, the nucleic acid sequence encoding the peptide, polypeptide or protein of interest is placed under the control of a T7 promoter, of a promoter inducible by IPTG, such as, for example, a Ptrc promoter or a Ptac promoter, or of a promoter inducible by Arabinose, such as, for example, Para.

In a preferred embodiment, the nucleic acid sequence encoding the antidote protein is directly functional, i.e. it directly encodes a functional antidote protein. Moreover, in one embodiment, the nucleic acid sequence encoding the peptide, polypeptide or protein of interest or the insertion site is not placed within the nucleic acid sequence encoding the antidote protein.

In one embodiment, the vector of the invention comprises a cer locus. The cer locus allows stable inheritence of ColE1 and related plasmids by preventing the runaway accumulation of multimers known as "dimer catastrophe". Multimer resolution is achieved through action of the XerCd site-specific recombinase at the cer site. Preferably, when a cer locus is inserted within the vector of the invention, the host cell is Escherichia coli.

In one embodiment, the vector of the invention does not comprise any antibiotic resistance gene. In another embodiment, the host cell of the invention does not comprise any antibiotic resistance genes. In one embodiment, neither the vector nor the host cell of the invention comprise any antibiotic resistance gene. Therefore, according to this embodiment, no antibiotic is required when producing peptide, polypeptide or protein of interest using the host cell and the vector of the invention.

The present invention also relates to a kit comprising a host cell of the invention, comprising at least two copies of a nucleic acid encoding a poison protein, and at least one vector (preferably a plasmid) as described hereinabove. Preferably, said vector carries at least one nucleic acid sequence encoding the antidote protein to the poison protein and a nucleic acid sequence encoding the recombinant peptide, polypeptide or protein of interest in an expression system, or an insertion site for inserting the nucleic acid sequence encoding the recombinant peptide, polypeptide or protein of interest in an expression system.

According to a preferred embodiment, the host cell of the invention comprises at least two nucleic acid sequences encoding the protein CcdB inserted in its genome, and the vector of the invention carries at least one nucleic acid sequence encoding CcdA.

In one embodiment, the vector comprises an expression system and an insertion site for inserting the nucleic acid sequence encoding the peptide, polypeptide or protein of interest within said expression system, thereby obtaining a functional vector for producing the peptide, polypeptide or protein of interest. Therefore, prior to transforming host cells with the vector of the invention for producing the peptide, polypeptide or protein of interest, the nucleic acid sequence encoding the peptide, polypeptide or protein of interest has to be inserted within the vector at the insertion site. Methods for inserting a nucleic acid sequence within an insertion site are well-known to the skilled artisan, and are usually based on the use of restriction enzymes.

With regard to the peptide, polypeptide or protein of interest, it may refer to any peptide, polypeptide or protein that is to be produced on a manufacturing scale, e.g. an industrial peptide, polypeptide or protein or a therapeutic peptide, polypeptide or protein.

Examples for peptide, polypeptide or protein that can be produced by the method of the invention are, without limitation, enzymes, regulatory proteins, receptors, peptides (e.g. peptide hormones), cytokines, antibodies, nanobodies, membrane or transport proteins.

The peptide, polypeptide or protein of interest may also be antigens as used for vaccination, vaccines, antigen-binding proteins, immune stimulatory proteins, allergens, full-length antibodies or antibody fragments or derivatives. Antibody derivatives may be selected from the group of single chain antibodies, (scFv), Fab fragments, F(ab')2 fragments, Fv fragments, single domain antibodies (VH or VL fragment), camelid single variable domains (VHH) or other antibody formats as described for instance in Andersen and Reilly (Current Opinion in Biotechnology, 2004, 15:456-462) or Holliger and Hudson (Nature Biotechnology, 2005 (23)9: 1126-1136).

The peptide, polypeptide or protein of interest in the present invention can also be exemplified by protein (viral antigen), e.g., coat protein, core protein, protease, reverse transcriptase, integrase, and so forth, encoded in the genome of a pathogenic virus, e.g., hepatitis B virus, hepatitis C virus, I-HV, influenza, and so forth; growth factors such as platelet-derived growth factor (PDGF), stem cell growth factor (SCF), hepatocyte growth factor (HGF), transforming growth factor (TGF), nerve growth factor (NGF), epidermal growth factor (EGF), fibroblast growth factor (FGF), insulin-like growth factor (IGF), and so forth; cytokines such as tumor necrosis factor, interferon, interleukin, and so forth; hematopoietic factors such as erythropoietin, granulocyte colony-stimulating factor, granulocyte-macrophage colony-stimulating factor, macrophage colony-stimulating factor, thrombopoietin, and so forth; peptide hormones such as luteinizing hormone-releasing hormone (LB-RH), thyrotropin-releasing hormone (TRH), insulin, somatostatin, growth hormone, prolactin, adrenocorticotropic hormone (ACTH), melanocyte-stimulating hormone (MSH), thyroid-stimulating hormone (TSH), luteinizing hormone (LU), follicle-stimulating hormone (FSH), vasopressin, oxytoxin, calcitonin, parathyroid hormone (PTH), glucagon, gastrin, secretin, pancreozymin, cholecystokinin, angiotensin, human placenta lactogen, human chorionic gonadotropin (HCG), cerulein, motilin, and so forth; analgesic peptides such as enkephalin, endorphin, dynorphin, kyotorphin, and so forth; enzymes such as superoxide dismutase (SOD), urokinase, tissue plasminogen activator (TPA), asparaginase, kallikrein, and so forth; peptide neurotransmitters such as bombesin, neutrotensin, bradykinin, substance P, Alzheimer's amyloid peptide (AD), SODI, presenillin 1 and 2, renin, Dsynuclein, amyloid A, amyloid P, activin, anti-HER-2, bombesin, enkephalinase, protease inhibitors, therapeutic enzymes, D 1-antitrypsin, mammalian trypsin inhibitor, mammalian pancreatic trypsin inhibitor, calcitonin, cardiac hypertrophy factor, cardiotrophins (such as cardiotrophin-1), CD proteins (such as CD-3, CD-4, CD-8 and CD-19), CFTR, CTNF, DNase, human chorionic gonadotropin, mouse gonadotropin-associated peptide, cytokines, transthyretin, amylin, lipoproteins, lymphokines, lysozyme, a growth hormone (including human growth hormone), bovine growth hormone, growth hormone releasing factor, parathyroid hormone, thyroid stimulating hormone, growth factors, brain-derived neurotrophic growth factor, epidermal growth factor (EGF), fibroblast growth factor (such as D FGF and D FGF), insulin-like growth factor-I and -II, des(1-3)-IGF-I (brain IGF-I), insulin-like growth factor binding proteins, nerve growth factor (such as NGF-D), platelet derived growth factor (PDGF), vascular endothelial growth factor (VEGF), receptors for growth hormones or growth factors, transforming growth factor (TGF) (such as TGF-D, TGF-D 1, TGF-D2, TGF-D3, TGF-D4 or TGF-D5), neurotrophic factors (such as neurotrophin-3, -4, -5, or -6), gelsolin, glucagon, kallikreins, mullerian-inhibiting substance, neurotrophic factors, p53, protein A or D, prorelaxin, relaxin A-chain, relaxin B-chain, rheumatoid factors, rhodopsin, a serum albumin (such as human serum albumin), inhibin, insulin, insulin chains, insulin A-chain, insulin D-chain, insulin receptor, proinsulin, luteinizing hormone, integrin, interleukins (ILs) (such as IL-1 to IL-10, IL-12, IL-13), erythropoietin, thrombopoietin, fibrillin, follicle stimulating hormone, clotting factors (such as factor VIIIC, factor IX, tissue factor, and von Willebrands factor), anti-clotting factors (such as Protein C, atrial naturietic factor, lung surfactant), a plasminogen activator (such as human tissue plasminogen activator or urokinase), thrombin, tumor necrosis factor-D or D, D-ketoacid dehydrogenase, addressins, bone morphogenetic proteins (BMPs), collagen, colony stimulating factors (CSFs) (such as M-CSF, GM-CSF and G-CSF), decay accelerating factor, homing receptors, interferons (such as interferon-alpha, -gamma and -beta), keratin, osteoinductive factors, PRNP, regulatory proteins, superoxide dismutase, surface membrane proteins, transport proteins, T-cell receptors, antigens such as gpl 20 (HIb) immuno toxins, atrial natriuretic peptide, seminal vesicle exocrine protein, D 2-microglobulin, PrP, precalcitonin, ataxin 1, ataxin 2, ataxin 3, ataxin 6, ataxin 7, huntingtin, androgen receptor, CREB-binding protein, gpl 20, p300, CREB, API, ras, NFAT, jun, fos, dentaorubral pallidoluysian atrophy-associated protein, a microbial protein (e.g., maltose binding protein, ABC transporter, glutathione S transferase, thioredoxin, D-lactamase), green fluorescent protein, red fluorescent protein, an enzyme such as superoxide dismutase, asparaginase, arginase, arginine deaminase, adenosine deaminase, ribonuclease, catalase, uricase, bilirubin oxidase, trypsin, papain, alkaline phosphatase, beta-glucoronidase, purine nucleoside phosphorylase or batroxobin, an opioid, e.g. endorphins, enkephalins or non-natural opioids, a hormone or neuropeptide, e.g. calcitonin, glucagon, gastrins, adreno-corticotropic hormone (ACTH), cholecystokinins, lutenizing hormone, gonadotropin-releassing hormone, chorionic gonadotropin, corticotrophin-releasing factor, vasopressin, oxytocin, antidiuretic hormones, thyroid-stimulating hormone, thyrotropin-releasing hormone, relaxin, prolactin, peptide YY, neuropeptide Y, pancreastic polypeptide, leptin, CART (cocaine and amphetamine regulated transcript), a CART related peptide, perilipin, melanocortins (melanocyte-stimulating hormones) such as MC-4, melanin-concentrating hormones, natriuretic peptides, adrenomedullin, endothelin, secretin, amylin, vasoactive intestinal peptide (VIP), pituary adenylate cyclase activating polypeptide (PACAP), bombesin, bombesin-like peptides, thymosin, heparin-binding protein, soluble CD4, hypothalamic releasing factor and melanotonins or functional analogs thereof. In another embodiment of the invention the peptide, polypeptide or protein of interest may be a processing enzyme such as proteases (eg. enterokinase, caspases trypsine like serine proteases), lipase, phosphatase, glycosyl hydrolases (eg. mannosidases, xylosidases, fucosidases), kinase, mono or dioxidase, peroxidase, transglutaminase, car-boxypeptidase, amidase, esterase, phosphatase and the like.

Preferred sources for such mammalian polypeptides include human, bovine, equine, porcine, lupine and rodent sources, with human proteins being particularly preferred.

The peptide, polypeptide or protein of interest of the present invention also encompasses variants of the aforementioned peptide, polypeptide or protein of interest. These variants encompass, for example, peptide, polypeptide or protein that has the same activity as the aforementioned peptide, polypeptide or protein of interest and that comprises an amino acid sequence with, in the amino acid sequence of the aforementioned peptide, polypeptide or protein of interest, one or more deleted, substituted, inserted and/or added amino acids. Such peptide, polypeptide or protein can be exemplified by peptide, polypeptide or protein that has the same activity as the aforementioned peptide, polypeptide or protein of interest and that comprises an amino acid sequence with, in the amino acid sequence of the aforementioned peptide, polypeptide or protein of interest, one or more deleted, substituted, inserted and/or added amino acids. Two or more different types of modifications selected from deletion, substitution, insertion, and addition may be carried out concurrently.

The peptide, polypeptide or protein of interest of the present invention also encompasses "partial peptides or polypeptides" of the aforementioned peptide, polypeptide or protein of interest. A partial peptide or polypeptide of the peptide, polypeptide or protein of interest can be exemplified by a partial peptide or polypeptide comprising an amino acid sequence in which a portion of the amino acid sequence of the aforementioned peptide, polypeptide or protein of interest runs uninterrupted, wherein the partial peptide or polypeptide preferably has the same activity as said peptide, polypeptide or protein of interest. Such a partial peptide or polypeptide can be exemplified by an amino acid sequence comprising at least 20 and preferably at least 50 of the amino acid residues in the amino acid sequence of the aforementioned peptide, polypeptide or protein of interest. This peptide or polypeptide preferably contains the amino acid sequence that corresponds to the region that is involved with the activity of the aforementioned peptide, polypeptide or protein of interest. In addition, the partial peptide or polypeptide used in the present invention may also be a partial peptide or polypeptide as yielded by a modification of this peptide wherein 1 or a plurality of amino acid residues (for example, approximately 1 to 20, more preferably approximately 1 to 10, and even more preferably approximately 1 to 5) is deleted from, substituted in, inserted into, and/or added to its amino acid sequence. The partial peptide or polypeptide used in the present invention can also be used as an antigen for antibody production.

In one embodiment of the invention, the peptide, polypeptide or protein of interest is selected from the group comprising Human growth hormone, human insulin, follicle-stimulating hormone, Factor VIII, Erythropoeietin, Granulocyte colony-stimulating factor, Alpha-glactosidase A, Alpha-L-iduronidase, N-actetylgalactosamine-4-sulfatase, Dornase alfa, Tisssue plasminogen activator, Glucocerebrosidase, Interferon, Insulin-like growth factor 1, bovine somatotropin, Porcine somatotropin, bovine chymosin, and envelop protein of the hepaptitis B virus.

The peptide, polypeptide or protein of interest also encompasses modified peptides, polypeptides or proteins that have underwent posttranslational and post-export modifications in the periplasm such as cyclization, glycosylation, phophorylation, methylation, oxidation, dehydratation, proteolytic cleavage.

In one embodiment, the peptide, polypeptide or protein of interest is an enzyme for metabolizing a biomolecule in the extracellular medium (herein referred as "extracellular biomolecule"). In one embodiment, the extracellular biomolecule comprises a polysaccharide or a lipid. In one embodiment of the invention, the polysaccharide comprises alginate, pectin, cellulose, cellobiose, laminarin, or a mixture thereof. In one embodiment of the invention, the lipid comprises a fatty acid, a glycolipid, a betaine lipid, a glycerolipid, a phospholipid, a glycerolphospholipid, a sphingolipid, a sterol lipid, a prenol lipid, a saccharolipid, a polyketide, or a mixture thereof. In one embodiment of the invention, the peptide, polypeptide or protein of interest is an enzyme converting a polysaccharide to a monosaccharide, an oligosaccharide, or both. In one embodiment of the invention, the peptide, polypeptide or protein of interest is an enzyme converting a lipid to a fatty acid, a monosaccharide, or both. In one embodiment of the invention, the monosaccharide or oligosaccharide is oligoalginate, mannuronate, guluronate, mannitol, a-keto acid, 4-deoxy-L-erythro-hexoselulose uronate (DEHU), 2-keto-3-deoxy D-gluconate (KDG), glucose, glucuronate, galacturonate, galactose, xylose, arabinose, or mannose. In one embodiment of the invention, the fatty acid is 14:0, trans-14, 16:0, 16:1n-7, trans-16, 16:2n-6, 18:0, 18:1n-9, 18:2n-6, 18:3n-6, 18:3n-3, 18:4n-3, 20:0, 20:2n-6, 20:3n-6, 20:4n-3,20:4n-6, or 20:5n-3.

In one embodiment of the invention, the peptide, polypeptide or protein of interest is an enzyme converting an extracellular biomolecule to a commodity chemical. In one embodiment of the invention, the commodity chemical is ethanol, butanol, or biodiesel. In one embodiment of the invention, the biodiesel is a fatty acid, a fatty acid ester, or a terpenoid.

In one embodiment, the peptide, polypeptide or protein of interest is a secreted protein. In one embodiment, the peptide, polypeptide or protein of interest is naturally secreted, i.e. the nucleic acid sequence encoding the same naturally comprises a signal peptide leading to its secretion. In another embodiment, the peptide, polypeptide or protein of interest is artificially secreted, i.e. the nucleic acid sequence encoding the same is fused to a signal peptide, thereby allowing its secretion. Examples of signal peptides that may be used in the context of the present invention include, but are not limited to, OmpA signal peptide (SEQ ID NO: 17), DsbA signal peptide (SEQ ID NO: 18) or PhoA signal peptide (SEQ ID NO: 19).

In another embodiment, the peptide, polypeptide or protein is a transmembrane protein.

In another embodiment, the peptide, polypeptide or protein is a protein which is toxic for the host cell.

In one embodiment, the host cell of the invention further comprises a nucleic acid sequence encoding a protein that induces the expression of the peptide, polypeptide or protein of interest, preferably placed in an expression system.

Examples of such nucleic acid sequences include, but are not limited to, the gene encoding the T7 RNA polymerase, T7 gene 1. In that case, the expression of the T7 RNA polymerase induces the expression of the peptide, polypeptide or protein of interest placed under the control of a T7 promoter.

Preferably, the nucleic acid sequence encoding a protein that induces the expression of the peptide, polypeptide or protein of interest is the T7 expression system. The T7 expression system was described in U.S. Pat. No. 4,952,496, which is incorporated herein by reference. The T7 expression system comprises a DNA fragment from the T7 phage, containing the entire coding sequence for the T7 RNA polymerase (i.e. the T7 gene 1). Any natural active promoter of the T7 gene 1 was removed and an inducible lacUV5 promoter was inserted ahead of the coding sequence. The lacUV5 promoter is induced by addition of IPTG to the culture medium.

In one embodiment, the host cell of the invention comprises a phage inserted within its genome. In one embodiment where the peptide, polypeptide or protein of interest is placed under the control of a T7 promoter, said genetically modified phage is as described in the PCT patent application WO2013/004817 (incorporated herein by reference). In one embodiment, said genetically modified phage is further defined as a phage wherein:
  an expression system is inserted (preferably a T7 expression system), and
  the S and/or the R genes are inactivated.

In one embodiment of the invention, the Int and/or Xis gene(s) of the phage is/are inactivated.

In one embodiment, the genetically modified phage is further defined as a phage wherein:
  an expression system is inserted (preferably a T7 expression system), the 5, R and/or the Q gene(s) is/are inactivated, and
the Int and/or Xis gene(s) is/are inactivated.

Examples of phages which can be used in the invention include, but are not limited to, the lambda (λ) phage (Enterobacteria phage lambda, accession number NC_001416), lambda-like and lambdoid phages. Lambda phage, also known as coliphage lambda, is a virus that infects *Escherichia coli*. Lambda is a temperate bacteriophage. Lambda-like phages form a family of bacteriophages and archaeal viruses which are characterized by long, non-contractile tails. Lambdoid phages are natural relatives of lambda phage. Most of them grow on *E. coli*, but a few come from other host cells, such as, for example, *Salmonella typhimurium*. Examples of lambda-like and lambdoid phages which could be used in the present invention include, but are not limited to, coliphage 434, phi80, phi81, HK97, P21 and P22.

In one embodiment, the phage is lambda DE3 (accession number EU078592). The Lambda DE3 phage is a modified lambda phage D69, comprising the gene encoding the T7 RNA polymerase under the control of a lacUV5 promoter.

According to a preferred embodiment, the genetically modified phage is the phage P11 having the sequence SEQ ID NO: 14 and being (DE3) ΔS-C, Δxis-ea10 (DE3 refers to lambda phage DE3 wherein the T7 RNA polymerase gene has been integrated within the sequence of int gene). Said modified phage P11 corresponds to the sequence NC_001416 wherein the coding sequences of genes S, R, Rz, Xis and Int are deleted.

According to another embodiment, the genetically modified phage is P12 corresponding to the sequence NC_001416 wherein the coding sequences of genes Int and S are deleted (one example of P12 is the sequence DE3 ΔS, Δxis-ea10).

According to another embodiment, the genetically modified phage is P13 corresponding to the sequence NC_001416 wherein the coding sequences of genes S, R, Rz, Q, Xis and Int are deleted (one example of P13 is the sequence DE3 ΔS-C, Δxis-ea10, ΔQ).

According to another embodiment, the genetically modified phage is P14 corresponding to the sequence NC_001416 wherein the coding sequences of genes R and Int are deleted (one example of P14 is the sequence DE3 ΔR).

According to another embodiment, the genetically modified phage is P15 corresponding to the sequence NC_001416 wherein the coding sequences of genes Q and Int are deleted (one example of P15 is the sequence DE3 ΔQ).

According to another embodiment, the genetically modified phage is P16 corresponding to the sequence NC_001416 wherein the coding sequences of genes S and Xis are deleted (one example of P16 is the sequence NC_001416 ΔS, Δxis-ea10).

According to another embodiment, the genetically modified phage is P17 corresponding to the sequence NC_001416 wherein the coding sequences of genes R and Xis are deleted (one example of P17 is the sequence NC_001416 ΔR, Δxis-ea10).

According to another embodiment, the genetically modified phage is P18 corresponding to the sequence NC_001416 wherein the coding sequences of genes Q and Xis are deleted (one example of P18 is the sequence NC_001416 Δxis-ea10, ΔQ).

According to another embodiment, the genetically modified phage is P19 corresponding to the sequence NC_001416 wherein the coding sequences of genes R, Rz and Int are deleted (one example of P19 is the sequence DE3 ΔR, ΔRz).

According to another embodiment, the genetically modified phage is P20 corresponding to the sequence NC_001416 wherein the coding sequences of genes S, Rz and Int are deleted (one example of P20 is the sequence DE3 ΔS, ΔRz).

According to another embodiment, the genetically modified phage is P21 corresponding to the sequence NC_001416 wherein the coding sequences of genes Rz, Q and Int are deleted (one example of P21 is the sequence DE3 ΔRz, ΔQ).

According to another embodiment, the genetically modified phage is P22 corresponding to the sequence NC_001416 wherein the coding sequences of genes S, Q and Int are deleted (one example of P22 is the sequence DE3 ΔS, ΔQ).

According to another embodiment, the genetically modified phage is P23 corresponding to the sequence NC_001416 wherein the coding sequences of genes R, Q, and Int are deleted (one example of P23 is the sequence DE3 ΔR, ΔQ).

According to another embodiment, the genetically modified phage is P24 corresponding to the sequence NC_001416 wherein the coding sequences of genes S, R and Int are deleted (one example of P24 is the sequence DE3 ΔS, ΔR).

According to another embodiment, the genetically modified phage is P25 corresponding to the sequence NC_001416 wherein the coding sequences of genes R, Rz and Xis are deleted (one example of P25 is the sequence NC_001416 ΔR, Δxis-ea10, ΔRz).

According to another embodiment, the genetically modified phage is P26 corresponding to the sequence NC_001416 wherein the coding sequences of genes S, Rz and Xis are deleted (one example of P26 is the sequence NC_001416 ΔS, Δxis-ea10, ΔRz).

According to another embodiment, the genetically modified phage is P27 corresponding to the sequence NC_001416 wherein the coding sequences of genes Q, Rz and Xis are deleted (one example of P27 is the sequence NC_001416 ΔRz, Δxis-ea10, ΔQ).

According to another embodiment, the genetically modified phage is P28 corresponding to the sequence NC_001416 wherein the coding sequences of genes S, Q and Xis are deleted (one example of P28 is the sequence NC_001416 ΔS, Δxis-ea10, ΔQ).

According to another embodiment, the genetically modified phage is P29 corresponding to the sequence NC_001416 wherein the coding sequences of genes R, Q and Xis are deleted (one example of P29 is the sequence NC_001416 ΔR, Δxis-ea10, ΔQ).

According to another embodiment, the genetically modified phage is P30 corresponding to the sequence NC_001416 wherein the coding sequences of genes R, S and Xis are deleted (one example of P30 is the sequence NC_001416 ΔS, Δxis-ea10, ΔR).

According to another embodiment, the genetically modified phage is P31 corresponding to the sequence NC_001416 wherein the coding sequences of genes R, Xis and Int are deleted (one example of P31 is the sequence DE3 ΔR, Δxis-ea10).

According to another embodiment, the genetically modified phage is P32 corresponding to the sequence NC_001416 wherein the coding sequences of genes S, Xis and Int are deleted (one example of P32 is the sequence DE3 ΔS, Δxis-ea10).

According to another embodiment, the genetically modified phage is P33 corresponding to the sequence NC_001416 wherein the coding sequences of genes Q, Xis and Int are deleted (one example of P33 is the sequence DE3 Δxis-ea10, ΔQ).

According to another embodiment, the genetically modified phage is P34 corresponding to the sequence NC_001416 wherein the coding sequences of genes S, R, Xis and Int are deleted (one example of P34 is the sequence DE3 ΔS, Δxis-ea10, ΔR).

According to another embodiment, the genetically modified phage is P35 corresponding to the sequence NC_001416 wherein the coding sequences of genes R, Q, Xis and Int are deleted (one example of P35 is the sequence DE3 ΔR, Δxis-ea10, ΔQ).

According to another embodiment, the genetically modified phage is P36 corresponding to the sequence NC_001416 wherein the coding sequences of genes S, Q, Xis and Int are deleted (one example of P36 is the sequence DE3 ΔS, Δxis-ea10, ΔQ).

According to another embodiment, the genetically modified phage is P37 corresponding to the sequence NC_001416 wherein the coding sequences of genes R, Rz, Xis and Int are deleted (one example of P37 is the sequence DE3 ΔR, Δxis-ea10, ΔRz).

According to another embodiment, the genetically modified phage is P38 corresponding to the sequence NC_001416 wherein the coding sequences of genes S, Rz, Xis and Int are deleted (one example of P38 is the sequence DE3 ΔS, Δxis-ea10, ΔRz).

According to another embodiment, the genetically modified phage is P39 corresponding to the sequence NC_001416 wherein the coding sequences of genes Rz, Q, Xis and Int are deleted (one example of P39 is the sequence DE3 ΔRz, Δxis-ea10, ΔQ).

According to another embodiment, the genetically modified phage is P40 corresponding to the sequence NC_001416 wherein the coding sequences of genes S, R, Q and Int are deleted (one example of P40 is the sequence DE3 ΔS, ΔR, ΔQ).

According to another embodiment, the genetically modified phage is P41 corresponds to the sequence NC_001416 wherein the coding sequences of genes S, R, Rz and Int are deleted (one example of P41 is the sequence DE3 ΔS-C).

According to another embodiment, the genetically modified phage is P42 corresponding to the sequence NC_001416 wherein the coding sequences of genes R, Rz, Q and Int are deleted (one example of P42 is the sequence DE3 ΔR, ΔRz, ΔQ).

According to another embodiment, the genetically modified phage is P43 corresponding to the sequence NC_001416 wherein the coding sequences of genes S, Rz, Q and Int are deleted (one example of P43 is the sequence DE3 ΔS, ΔRz, ΔQ).

According to another embodiment, the genetically modified phage is P44 corresponding to the sequence NC_001416 wherein the coding sequences of genes S, R, Q and Xis are deleted (one example of P44 is the sequence NC_001416 ΔS, ΔR, Δxis-ea10, ΔQ).

According to another embodiment, the genetically modified phage is P45 corresponds to the sequence NC_001416 wherein the coding sequences of genes S, R, Rz and Xis are deleted (one example of P45 is the sequence NC_001416 ΔS-C, Δxis-ea10).

According to another embodiment, the genetically modified phage is P46 corresponding to the sequence NC_001416 wherein the coding sequences of genes R, Rz, Q and Xis are deleted (one example of P46 is the sequence NC_001416 ΔR, ΔRz, Δxis-ea10, ΔQ).

According to another embodiment, the genetically modified phage is P47 corresponding to the sequence NC_001416 wherein the coding sequences of genes S, Rz, Q and Xis are deleted (one example of P47 is the sequence NC_001416 ΔS, ΔRz, Δxis-ea10, ΔQ).

According to another embodiment, the genetically modified phage is P48 corresponding to the sequence NC_001416 wherein the coding sequences of genes S, R, Q, Xis and Int are deleted (one example of P48 is the sequence DE3 ΔS, ΔR, Δxis-ea10, ΔQ).

According to another embodiment, the genetically modified phage is P49 corresponding to the sequence NC_001416 wherein the coding sequences of genes S, Rz, Q, Xis and Int are deleted (one example of P49 is the sequence DE3 ΔS, ΔRz, Δxis-ea10, ΔQ).

According to another embodiment, the genetically modified phage is P50 corresponding to the sequence NC_001416 wherein the coding sequences of genes R, Rz, Q, Xis and Int are deleted (one example of P50 is the sequence DE3 ΔR, ΔRz, Δxis-ea10, ΔQ).

According to another embodiment, the genetically modified phage is P51 corresponding to the sequence NC_001416 wherein the coding sequences of genes S, R, Q, Rz and Int are deleted (one example of P51 is the sequence DE3 ΔS-C, ΔQ).

According to another embodiment, the genetically modified phage is P52 corresponding to the sequence NC_001416 wherein the coding sequences of genes S, R, Rz, Q and Xis are deleted (one example of P52 is the sequence NC_001416 ΔS-C, Δxis-ea10, ΔQ).

According to another embodiment, the genetically modified phage is P53 corresponding to the sequence NC_001415 wherein the coding sequences of genes Q, Xis and Int are deleted (one example of P53 is the sequence DE3 Δxis-ea10, ΔQ).

The present invention also relates to a process for producing a peptide, polypeptide or protein of interest, wherein said method comprises:

cultivating a host cell of the invention, comprising:
- at least two copies of a nucleic acid sequence encoding a poison protein, preferably CcdB,
- at least one copy of a nucleic acid sequence encoding the antidote protein to the poison protein, preferably CcdA, and
- at least one copy of the nucleic acid sequence encoding the peptide, polypeptide or protein of interest, and recovering the peptide, polypeptide or protein of interest.

In one embodiment, the at least two copies of a nucleic acid sequence encoding a poison protein are inserted within the genome of the host cell.

In one embodiment, the at least one copy of a nucleic acid sequence encoding the antidote protein to the poison protein and the at least one copy of the nucleic acid sequence encoding the peptide, polypeptide or protein of interest are carried by the same vector. Therefore, only host cells containing the vector are propagated, while host cells without the vector die due to the toxic effect of the poison protein.

In one embodiment of the invention, the nucleic acid sequence encoding the peptide, polypeptide or protein of interest is comprised within the expression system. According to this embodiment, the production of the peptide, polypeptide or protein of interest is direct, i.e. it results from the expression of the gene of the expression system, for example by culture in a medium wherein the promoter comprised in the expression system is induced. For example, in one embodiment, the nucleic acid sequence encoding the peptide, polypeptide or protein of interest is placed under the control of a pLac or pTRC promoter, and the expression of the peptide, polypeptide or protein of interest is induced when IPTG is added to the culture medium. Moreover, in another embodiment, the nucleic acid sequence encoding the peptide, polypeptide or protein of interest is placed under the control of a Para promoter, and the expression of the peptide, polypeptide or protein of interest is induced when arabinose is added to the culture medium.

In another embodiment, the host cell of the invention further comprises another expression system comprising the nucleic acid sequence of the T7 RNA polymerase under the control of a lac promoter, preferably the lacUV5 promoter, inserted in its genome.

According to this embodiment, the process for producing the peptide, polypeptide or protein of interest comprises the transformation of the host cell with a vector, preferably a plasmid, comprising the nucleic acid sequence of the peptide, polypeptide or protein of interest under the control of the T7 promoter and the nucleic acid sequence encoding the antidote protein. The expression from the T7 promoter is under the control of T7 RNA polymerase, which is stringently specific for the T7 promoter, i.e. the T7 promoter can only be utilized by the RNA polymerase of bacteriophage T7. When IPTG is added to the culture medium, T7 RNA polymerase is expressed by transcription from the lac promoter which will allows the expression of the peptide, polypeptide or protein of interest.

According to one embodiment, the peptide, polypeptide or protein of interest is secreted by the host cell in the fermentation broth. According to this embodiment, the peptide, polypeptide or protein of interest may be easily recovered from the fermentation broth using methods well-known in the art.

According to another embodiment, the peptide, polypeptide or protein of interest is not secreted by the host cell in the fermentation broth. Methods for recovering an intracellular or periplasmic peptide, polypeptide or protein of interest are also well-known in the art.

Examples of such methods include, but are not limited to, the use of trichloroacetic acid (TCA) or cracking buffer containing sodium dodecyl sulfate (SDS) to recover total proteins in denaturing conditions or the use of sonication, French press or equivalent to disrupt bacteria under pressure in order to recover total cytoplasmic proteins in native (not denaturing) conditions. Next, the peptide, polypeptide or protein of interest can be purified using specific methods including but not limited to the use of affinity or ion exchange columns.

The present invention also refers to a method for preparing a host cell as hereinabove described.

The method for preparing a host cell of the invention comprises inserting at least two copies, preferably two copies, of the nucleic acid sequence encoding the poison protein within the genome of the host cell. Preferably, said poison protein is CcdB, more preferably said the nucleic acid sequence encoding the poison protein is SEQ ID NO: 1.

In one embodiment, the method for preparing a host cell of the invention comprises a step of deletion, wherein nucleic acid sequences of the host cell are deleted.

Methods for inserting or deleting the sequence of a gene are well known by the skilled artisan. The more efficient method is the homologous recombination method mediated by the lambda Red-encoded genes or the recE and recT genes from the prophage Rac. This method was well described by several researchers including Datsenko and Wanner (PNAS 97-12, 6640-6645, 2000) and Stewart et al. (WO0104288). PCR products are generated using primers with 20- to 60-nt extensions that are homologous to regions adjacent to the gene to be deleted or to the region wherein a nucleic acid sequence will be inserted. Since only a small amount of bacteria will effectively recombine the fragment of interest, it is necessary to have a strong selection marker to select it. Antibiotic markers can be used to select the recombinants: the modified primers are used to amplify an antibiotic resistance gene. After transformation and activation of the recombination genes, recombinant bacteria are selected on medium containing the appropriate antibiotic. In this case, the targeted gene or region is replaced by an antibiotic resistance gene. In order to use the same strategy for the next deletion, it is necessary to remove this antibiotic resistance gene during a second step. As described in Datsenko and Wanner, it is possible to use antibiotic resistance gene that are flanked by FRT (FLP recognition target) sites. The resistance genes are then eliminated by using a helper plasmid encoding the FLP recombinase. The antibiotic resistance gene is removed by this site-specific recombinase but this method leaves traces: one site-specific recombination site is still present after removal of the antibiotic resistance gene.

To avoid the presence of this site, more preferably, the method of the invention uses galK as a marker gene. The principle of the galK selection is described in Warming et al. (Nucleic acid research, 2005, 33(4)). This method uses galK as a positive selection marker (growth on minimal medium containing galactose) during the first recombination (insertion). The removal of this marker is performed during a second homologous recombination step. During this step, galK is used as a negative selection marker on minimal medium containing 2-deoxy-galactose (DOG). The galK gene product, galactokinase, catalyzes the first step in the galactose degradation pathway. Galactokinase also efficiently catalyzes the phosphorylation of the DOG galactose analog. The product of this reaction cannot be further metabolized, leading to the accumulation of a toxic molecule (2-deoxy-galactose-1-phosphate). The advantage of this method is to avoid the presence of specific recombination site after deletion of the targeted gene and removal of the selective marker.

In one embodiment, the method of the invention further comprises a step of infection of the host cell by a genetically modified phage as defined hereinabove. In one embodiment of the invention, said infection step includes the use of a helper phage. In the meaning of the present invention, the term "helper phage" refers to a phage used to complement a deletion or an inactivation of another phage. The helper phage will provide the missing functions to said another phage to be able to infect bacteria or to prepare phage stock. Usually, the helper phage cannot form a lysogen by itself because it is cI minus (it has no repressor and is thus virulent).

Processes for infecting a host cell with a phage using a helper phage are well known in the art. In one embodiment, a first step is the preparation of the lysates and a second one is the lysogenization. Briefly, the bacterial lysates of the helper phage may be prepared using standard methods as described in "Molecular cloning: a laboratory manual", Sambrook et al. (2001, ISBN 978-087969577-4) or in "Large- and Small-Scale Preparation of Bacteriophage lambda lysate and DNA", Su et al., BioTechniques 25:44-46 (July 1998). Preparation of the phage of interest may be done using the same principle, after phage induction (most often using UV irradiation or any situation where a lysogen undergoes DNA damage or the SOS response of the host or Cro production) in order to launch the lytic cycle and using a helper phage to provide the missing functions. An alternative to the helper phage is the use of a plasmid encoding the missing functions.

Next, the phage lysates may be mixed with the targeted bacteria and plated on LB plates in order to get lysogens (as described in lambda DE3 lysogenization kit from Novagen, User Protocol TB031 or an alternative method is described in Studier and Moffat, Journal of Molecular Biology, 1986, 189:113-130). A selection phage can be used to select specifically bacteria containing the phage of interest. This selection phage is a virulent phage having the same immunity as the phage of interest. Consequently, the selection phage is unable to form plaques or to kill bacteria lysogens for the phage of interest because this phage produces the cI repressor (also called C2 in DE3 lambda phage).

In one embodiment, the method of the invention further comprises transforming the host cell of the invention with a vector, preferably a plasmid as described hereinabove, carrying (1) a nucleic acid sequence encoding the antidote to the poison protein and (2) a nucleic acid sequence encoding the peptide, polypeptide or protein of interest. Methods for transforming a cell with a vector are well-known in the art and include, but are not limited to, chemical transformation and electroporation.

The method for producing a peptide, polypeptide or protein of interest using the host cell of the invention thus presents the following advantages:
  it may be applied to any peptides, polypeptides or proteins, even to peptides, polypeptides or proteins which are toxic to the host cell;
  it may be applied to any host cell, as the insertion of the ccdB gene within the genome of a host cell is easy for the skilled artisan;
  as shown in the examples below, it results in an increased production yield of the peptide, polypeptide or protein of interest;
  as shown in the examples below, it allows increasing stability of the vector comprising the nucleic acid sequence encoding the peptide, polypeptide or protein of interest, especially when the peptide, polypeptide or protein of interest is toxic for the host cell; and
  in some embodiments, it does not comprise using antibiotics, and both the host cell and the vector are free of antibiotic-resistance genes.

EXAMPLES

The present invention is further illustrated by the following examples.

Example 1: Duplication of the ccdB Gene Increases YieldPproduction

Figure 1:
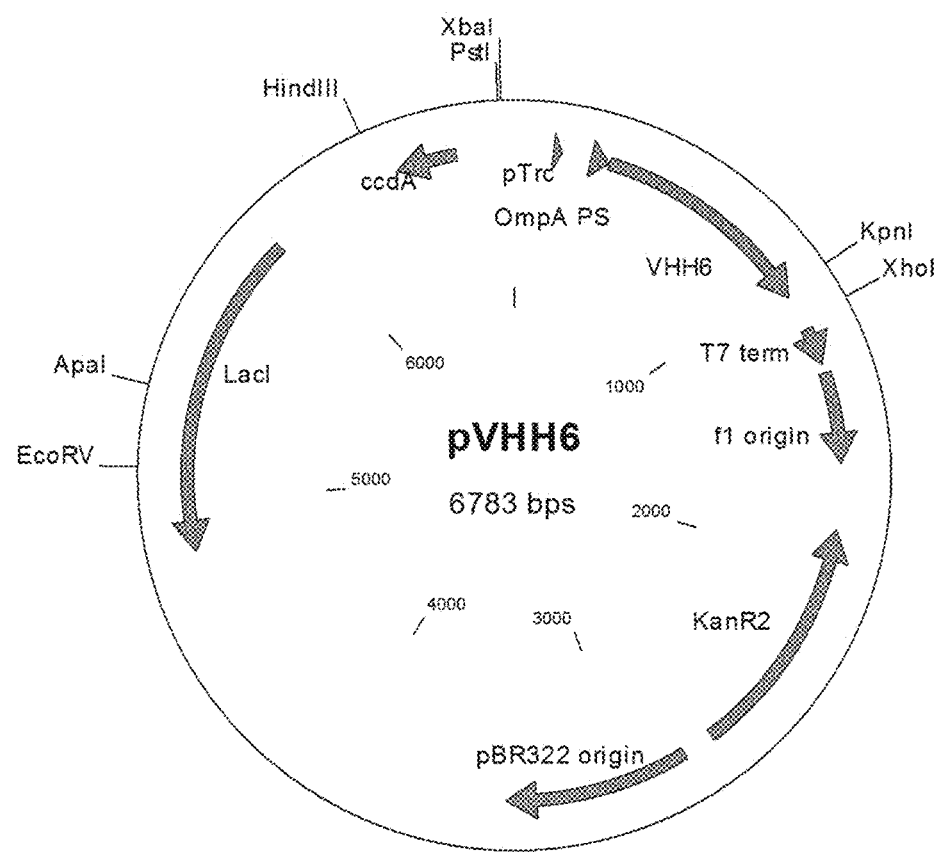
FIG. 1 is a map of the pVHH6 vector.

In order to test the stability brought by the Staby® technology (technology based on the insertion of one copy of the ccdB gene within the host chromosome, Delphi Genetics, StabyExpress® products, patent WO9958652), we produced a secreted protein (a variable heavy chain antibody fragment named VHH6) which seems to have also toxic properties in E. coli. The W3110 E. coli strain (genetic background: E. coli K12, genotype: F− lambda− INV(rrnD-rrnE) rph-1) was used as producer host and expression was realized with pTrc promoter on a pBR322 vector (pVHH6; FIG. 1). The production of the W3110 strain using classical antibiotic stabilisation system (here the kanamycin resistance) was compared to the production of the W3110ccdB strain which has been modified to use the Staby® technology (ccdB gene being introduced inside the strain chromosome). Vectors used for this comparison both contained the ccdA gene and the vector used in W3110ccdB was deleted for the kanamycin resistance gene (pVHH6ΔKan).

Strains were grown at 30° C. in LB medium (10 ml) with or without antibiotics and induced (0.5 mM IPTG) for 4 h when $OD_{600}$ reaches 0.5. No production was visible when analysed by SDS-PAGE despite 100% of plasmid stability in both selection systems under these gentle induction conditions. Stronger induction condition has been applied as followed (here after continuous fermentation based on perfusion). Strains were grown in 500 ml fermenters and $OD_{600}$ was maintained constant at 0.3 by perfusion: addition of fresh medium (up to 5l) and removing of the overflow to maintain always $OD_{600}$ to 0.3 in the fermenter. After 5l of perfusion, the $OD_{600}$ increased and induction was finally realized for 24 h when cultures reached an $OD_{600}$ of 0.5. When antibiotic selection system is used to stabilize the expression vector, the final plasmid stability was determined by plating bacteria on plates containing or not the appropriate antibiotics (according to the resistance gene encoded by the plasmid). Plates without antibiotics is used to determine the total number of bacteria and plates containing antibiotics are used to determine the number of bacteria still containing the plasmid.

The plasmid stability was evaluated to about 0% for the bacteria using the antibiotics (no colony on plates containing antibiotics).

Figure 2:
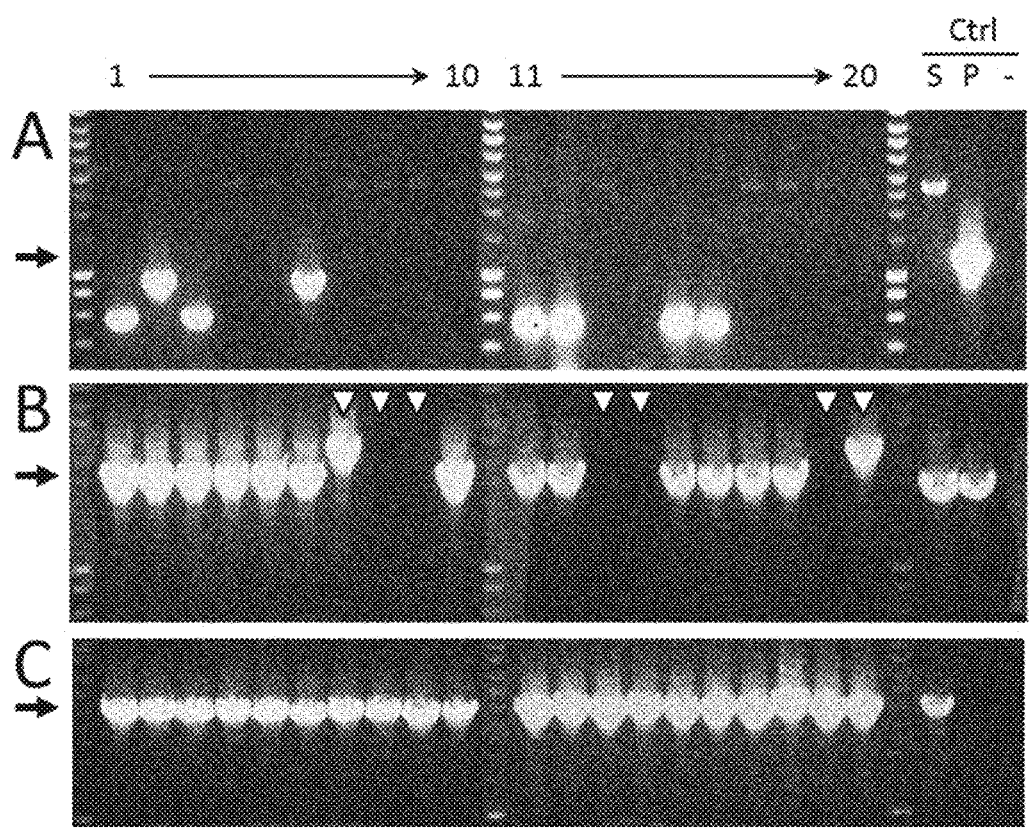
FIG. 2 is a photograph showing the PCR screening on the W3110ccdB strain after 24 h of induction of pVHH6ΔKan. Culture after induction has been streaked on plates without antibiotics and PCR done on 20 colonies. PCR results over VHH6 (A), ccdB (B) and strain specific (C) genes are shown. Arrows on the left show expected size of the PCR products. Head arrows show ccdB alterations.

When using the Staby® system based on ccdA and ccdB, no antibiotic resistance gene is present. Consequently, the presence or absence of the plasmid is tested by PCR. Since we are using the Staby® system, we hypothesize that due to the presence of the selection ccdB gene in the chromosome bacteria and the ccdA antidote gene in the plasmid, all bacteria growing on plates should contain the plasmid. Unexpectedly, we observed a stability of about 65% by PCR experiments on colonies (FIG. 2B). Indeed, even if the stability is drastically increased, this is the first time that the Staby® technology does not give 100% of stability.

Moreover, among the 65% of retention, the gene of interest (VHH6 gene) was mutated by partial or full deletions in all plasmid tested (FIG. 2A). Bands of ccdB PCR which are higher than expected were extracted and sequenced. Sequencing results show that the ccdB gene is inactivated by small insertion sequence (insAB) insertion (SEQ ID NO: 16). According to the strain specific PCR results (FIG. 2C), unamplified band over ccdB gene could be due to large deletion or insertion in the ccdB region. This experiment has been replicated and equivalent results were observed.

Therefore, the Staby® technology has to be improved in order to avoid this kind of stabilisation system inactivation. A second copy of the poison gene has been inserted between the yjjK and slt genes (resulting in W3110 2ccdB strain). These genes have been chosen because they stand at the opposite side of the *E. coli* chromosome regarding to the first ccdB gene location and because the intergenic space seems to be non-coding.

In order to compare the production in W3110, W3110ccdB and W31102ccdB strains, the following protocol has been applied. Single colonies were grown overnight in 10 ml LB medium at 37° C. The following day, 1 µl from each culture was used for inoculation of 10 ml fresh LB medium. Cultures were grown overnight at 37° C. This step was repeated once again to perform additional generations (as realized in the fermenter). The following day, 10 µl from each culture was used for inoculation of 10 ml fresh LB medium. Cultures were grown at 30° C. and induced at $OD_{600}$ 0.5 for 24 h. Kanamycin was used all along these steps only for the W3110 strain. Despite the use of this antibiotic to maintain the expression plasmid, its stability was about 0% after induction. On the other side, the plasmid stability was about 100% for both Staby® systems (i.e. with 1 or 2 ccdB genes) under this more gentle protocol: every PCR done over ccdB genes and plasmid ccdA genes were at the expected size. Only some VHH6 genes were mutated (27%) for the W31102ccdB culture.

Figure 3:
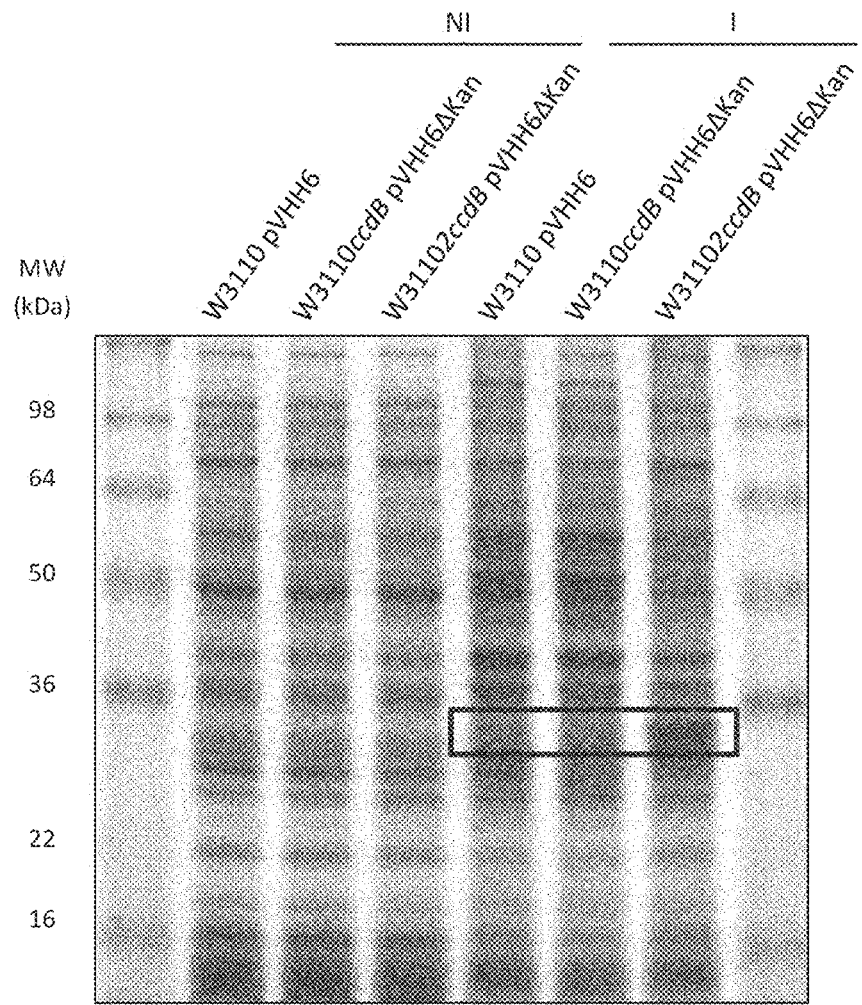
FIG. 3 is a photograph showing production comparison of W3110 pVHH6, W3110ccdB pVHH6ΔKan and W31102ccdB pVHH6ΔKan strains on SDS-PAGE. Differences are observed between non-induced (NI) and induced (I) samples, but especially between induced samples (rectangle).

Productions were also compared by Coomassie blue SDS-PAGE (FIG. 3). Unexpectedly, the yield of production of the W31102ccdB strain is much higher than with other strains (VHH6=27 kDa). This kind of yield increase has already been reported by using the Staby® technology but with only one copy of the ccdB gene (Peubez et al., Microbial Cell Factories 2010, 9:65; Sodoyer et al., In: Antibiotic Resistant Bacteria—A Continuous Challenge in the New Millennium 2012). Here, the yield increase surprisingly happens only when two ccdB copies are present despite the fact that the plasmid is stable and present in the bacteria with one copy of the ccdB gene.

Example 2: Application of the Staby® 2ccdB Technology to Produce Other Proteins

Figure 4:
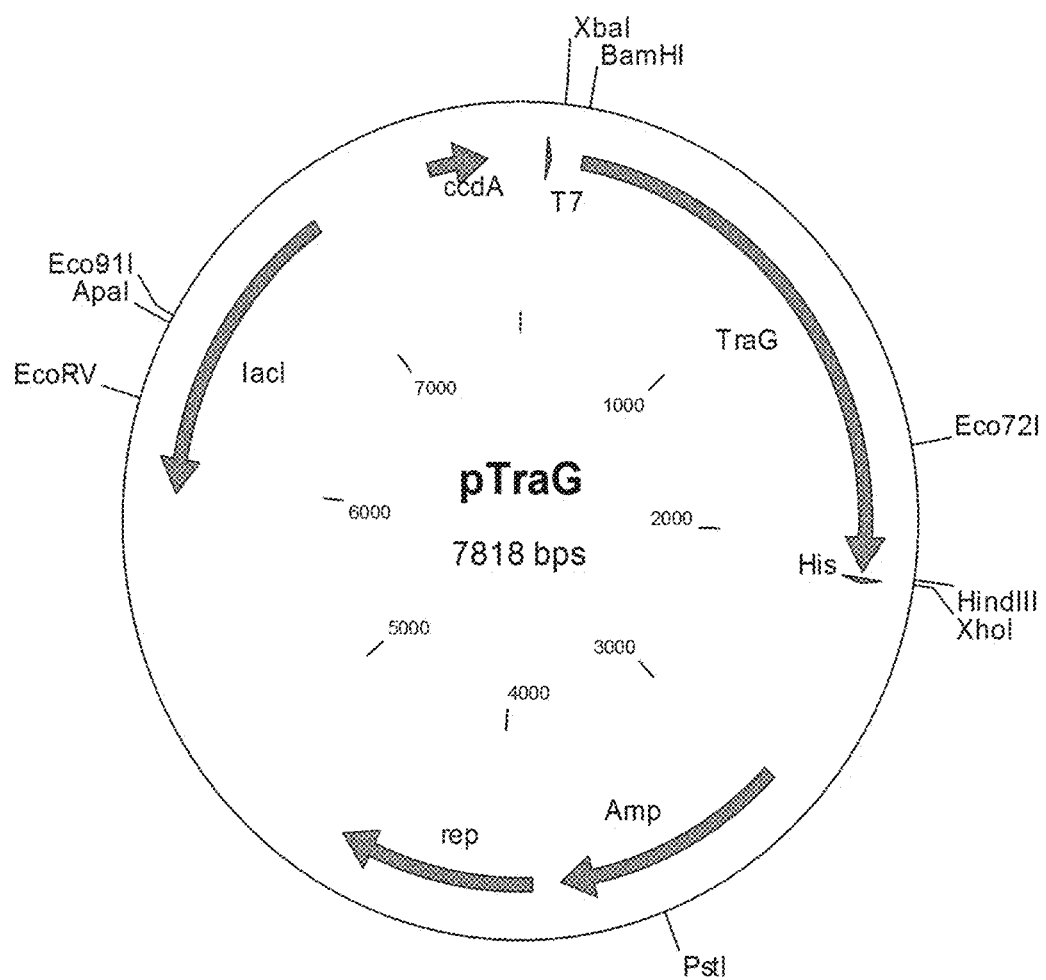
FIG. 4 is a map of the pTraG vector.

In order to test if the use of the strains with two copies of the ccdB gene is possible for all proteins (including proteins already well expressed with only one copy of ccdB), we tested the production of the TraG protein of 70 kDa (Szpirer et al., 2000, Mol. Microbiol. 37(6) 1283-1292). W3110 (DE3)ccdB and W3110(DE3)2ccdB strains with the plasmid coding for the antidote CcdA and TraG (pTraG) were constructed (FIG. 4). The traG gene was under the control of the T7 promoter. These strains and plasmid use the Staby® technology to stabilize the plasmids. The first observation was that in the presence of the plasmid encoding ccdA, the presence of two copies of the ccdB gene does not affect the viability nor the growth of the W3110 strain: one copy of the ccdA gene in the plasmid is enough to get full viability.

Figure 5:
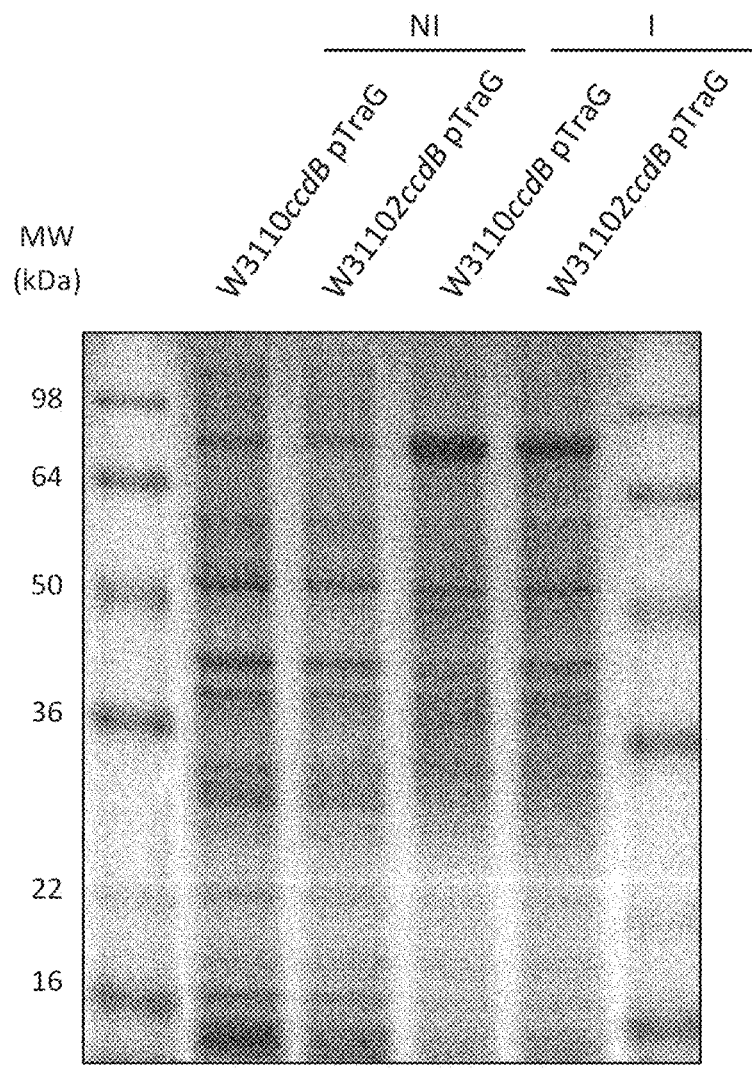
FIG. 5 is a photograph showing production comparison of W3110ccdB pTraG and W31102ccdB pTraG strains on SDS-PAGE. Differences are observed between non-induced (NI) and induced (I) samples, but not between induced samples.

The production of TraG under the classical Staby® system (1 ccdB gene) is equivalent to the one with the new Staby® system (2 ccdB genes) (FIG. 5). However the production with 1 ccdB gives already very good yield, so an increase of this yield is maybe not possible, even by applying the new Staby® system.

In order to confirm our previous results, another production has been realized. An antibody fragment has been chosen as a model (D1.3=24 kDa for heavy and light chains or 50 kDa for the associated chains) and expressed using a Para promoter (arabinose induction). The vector (pBAD24) has been adapted to the strains containing the ccdB gene(s) (insertion of ccdA and deletion of the ampicillin resistance gene).

Figure 6:
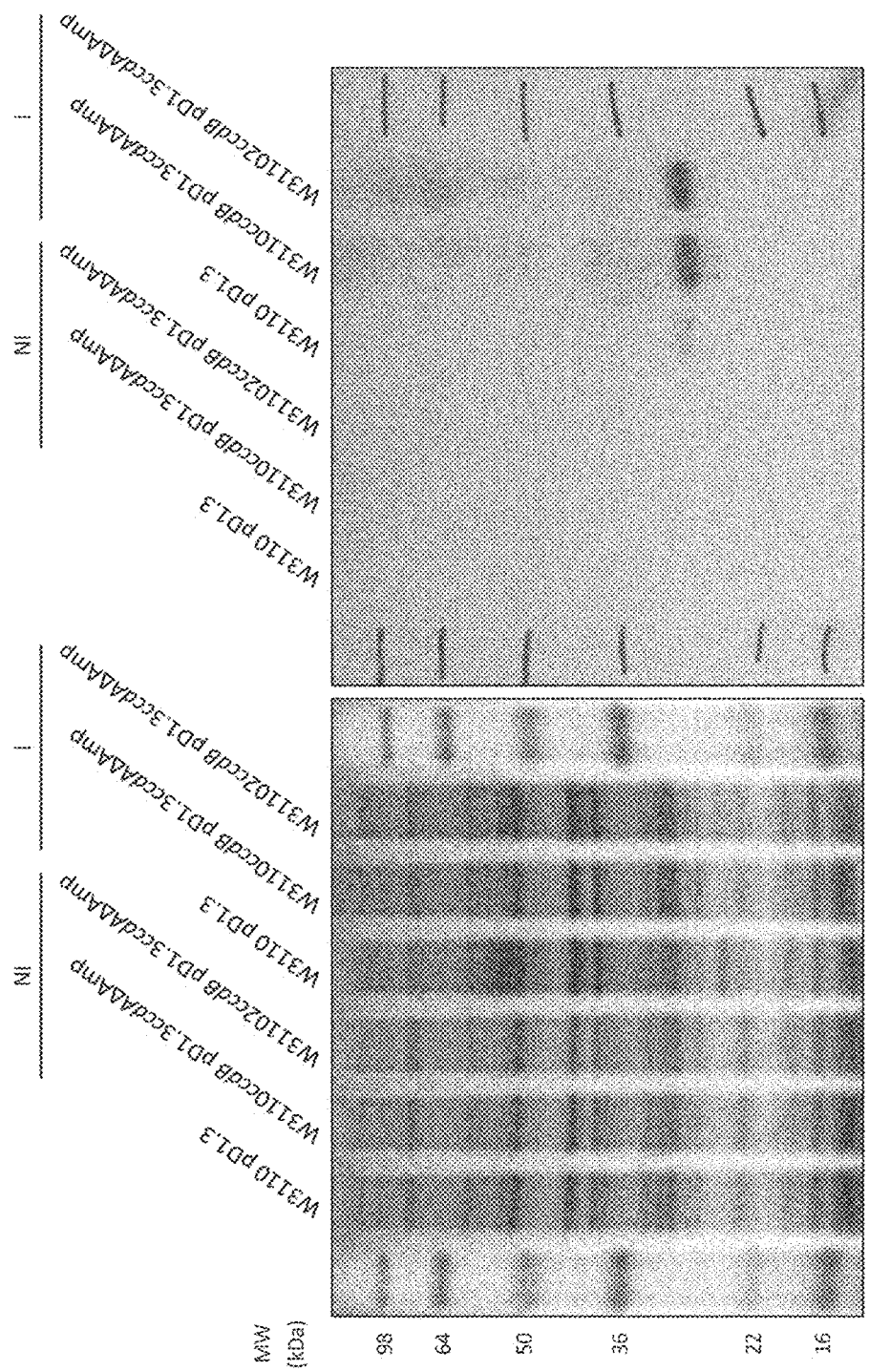
FIG. 6 is a combination of two photographs showing production comparison of W3110 pD1.3, W3110ccdB pD1.3ccdAAAmp and W31102ccdB pD1.3ccdAAAmp strains on SDS-PAGE by Coomassie blue staining (left) or by western blot (right). Differences are well observed by western blot between non-induced (NI) and induced (I) samples.

As shown in FIG. 6, the production yield is strongly increased by using 1 or 2 copies of the ccdB genes but we did not observe a difference between the two strains (including growth and speed).

In conclusion, the use of the strain with 2 copies of ccdB may be used for the production of any protein. However, the yield advantage depends on each protein and when the yield is already very high when using only 1 copy of ccdB, the strain encoding 2 copies gives the same results. Since, as industrial producers and researchers never know whether a protein will be difficult to produce or not when they are starting their experiments, it is an advantage to be able to use the same strain for classical and difficult-to-produce proteins and to start immediately with the strain designed for the hardest proteins.

Example 3: Application of the 2ccdB Technology to Produce Proteins in Other Host Strains

Figure 7:
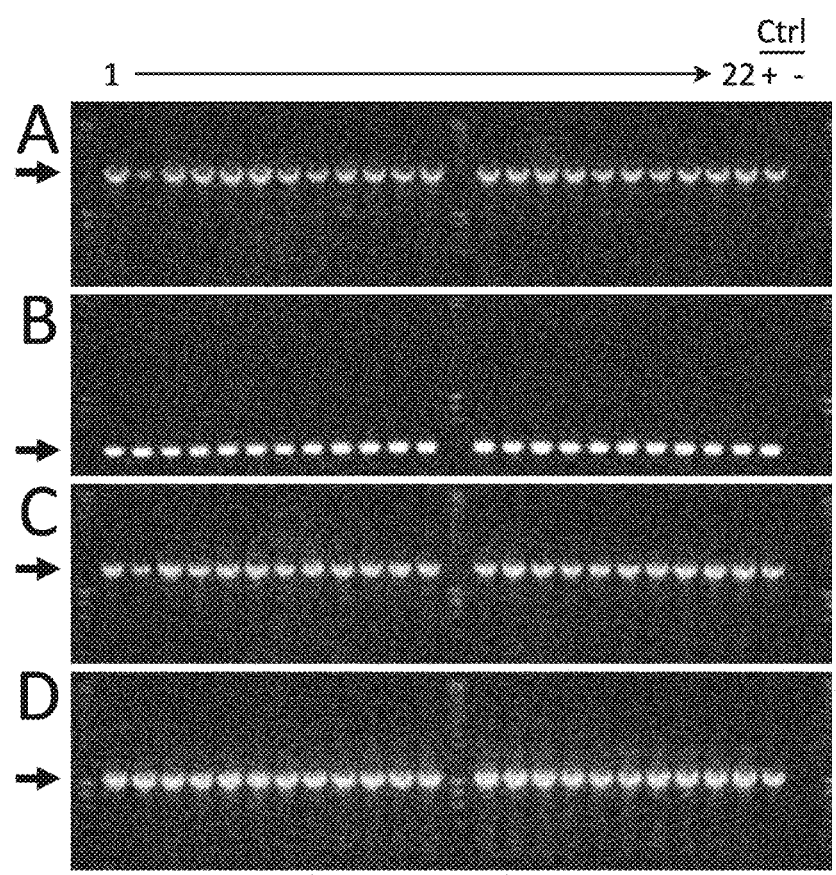
FIG. 7 is a photograph showing screening PCR on the SE3 (BL21(DE3)2ccdB) strain after 24 h of induction of pStaby1.2 TraG. Culture after induction has been streaked on Petri dishes and PCR done on 22 colonies. PCR results over TraG (A), ccdA (B), the first ccdB (C) and the second ccdB (D) genes are shown. Arrows on the left show expected size of the PCR products.

*E. coli* strains are divided in K12 and B types. As the W3110 strain is a K12 strain, the applicability of the 2ccdB technology to the B strains has been tested. Thus two copies of ccdB have been introduced in the genome of an *E. coli* B (BL21(DE3) type—Genetic background: *E. coli* B—genotype F—ompT gal dcm lon $hsdS_B(r_B-m_B-)$ λ(DE3 [lacI lacUV5-T7 gene1])) to give the SE3 strain. Then, perfused fermentation has been realized to produce the TraG protein after several generations. Stability of the plasmids after 24 h of induction is of 100% (FIG. 7). Every ccdB genes are intact under these conditions of expression.

Similar results were obtained in another K12 derived strain having the following genotype: F–endA1 glnV44 thi-1 recA1 relA1 gyrA96 deoR nupG Φ80dlacZΔM15Δ (lacZYA-argF)U169, hsdR17(rK–mK+), λ–, dcm::FRTccdB yjjK::FRTccdB. This strain was derived from DH5 alpha in which 2 copies of ccdB gene were inserted as described above.

These results show that it is possible to construct different *E. coli* strains containing the insertion of 2 copies of the ccdB gene. The presence of these 2 copies is not deleterious.

Example 4: Duplication of the gyrA Gene

As described earlier, the Staby® technology is based on the toxicity of the CcdB protein for *E. coli*. As the CcdA antidote inhibits the expression of the ccdB gene, no selection pressure is applied against this toxin gene. It is so unlikely to find some *E. coli* resistant strains to CcdB. However, this kind of resistant has been artificially isolated by applying several round of growth in presence of mutagen agent (Bernard et al., J Mol Biol. 1992, 226:735). This resistant strain presents a mutation in the gyrA gene (the target of CcdB) changing the arginine 462 in a cysteine.

During the expression of our toxic protein model VHH6 (see Example 1), strains had been isolated with wild-type ccdB gene but without the plasmid (and so the ccdA gene). Thus, these strains were resistant to CcdB. The gyrA gene of these strains has been sequenced to confirm the arginine 462 modification in another already undescribed amino acid (serine).

By duplicating the ccdB gene as mentioned in this patent, we guess that the pressure of selection on the gyrA gene will increase and generate more easily CcdB resistant strains.

In order to avoid those mutants, the duplication of the gyrA gene has also been realized. This new copy of gyrA has been integrated in the same time that the second copy of ccdB (in the same insert) between the yjjK gene and the slt gene in the SE2 strain by transduction of a DNA fragment containing the gyrA, kanamycin and ccdB genes surrounded by homologous regions used as recombination arms. The recombination event was selected using the kanamycin resistance gene. This gene was surrounded by two FRT sites allowing its removal using the FLP recombinase. This construction has been successfully done and the viability of the strain has not changed. TraG expression abilities were tested as in Example 2 and performed with the derivative of SE2 strain called SE4 (BL21(DE3)2ccdB 2gyrA).

Figure 8:
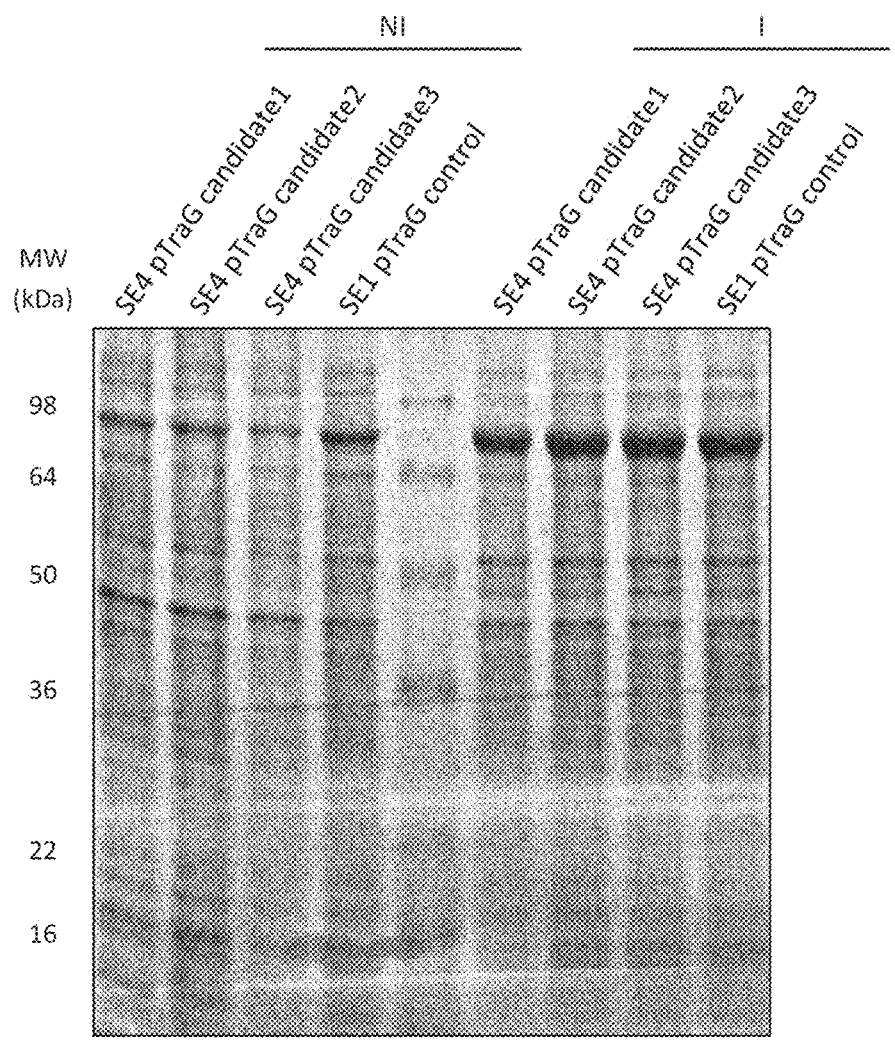
FIG. 8 is a photograph of a SDS-PAGE gel showing production comparison of SE1 pStabyTraG and SE4 (BL21 (DE3)2ccdB 2gyrA) pStabyTraG strains. Differences are observed between non-induced and induced (I) samples.

As shown on FIG. 8, the production of TraG under the classical Staby® system (1 ccdB gene) is equivalent to the one with the new Staby® system (2 ccdB genes+1 additional copy of gyrA). However the production with 1 ccdB gives already very good yield, so an increase of this yield is maybe not possible, even by applying the new Staby® system.

We can observe that the addition of 2 ccdB and 1 additional copy of gyrA (1 copy is already present) do not reduce the amount of protein due to higher toxicity of the CcdB poison protein.

Figure 9:
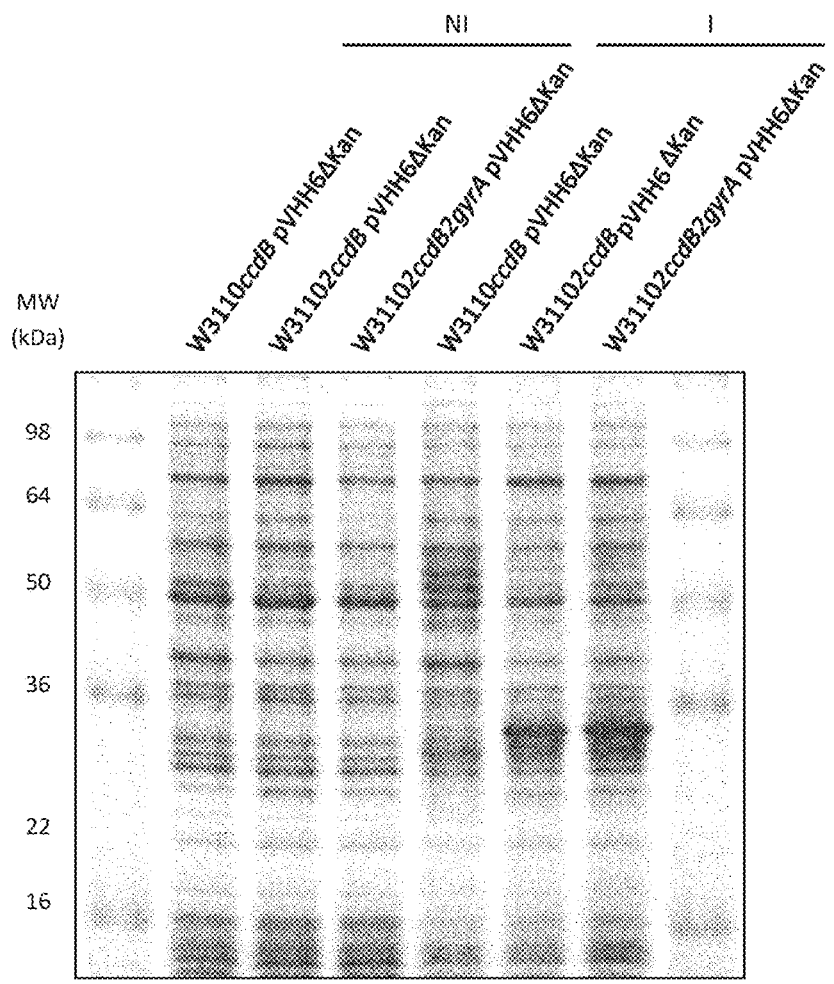
FIG. 9 is a photograph showing production comparison of W3110ccdB pVHH6ΔKan, W31102ccdB pVHH6ΔKan and W31102ccdB 2gyrA pVHH6ΔKan strains on SDS-PAGE. Differences are observed between non-induced (NI) and induced (I) samples, but especially between induced samples.

Similar genetic modifications were applied to *E. coli* W3110 derivative (strain called KW4: W31102ccdB 2gyrA). This strain has been compared to other W3110 strains for the production of the toxic protein model VHH6. After production, each strain was tested regarding the presence of the plasmid and 100% of retention was observed in all strains. As shown in FIG. 9, the production of VHH6 is better when 2 copies of the ccdB gene are present (FIG. 9). Moreover, as mentioned for the SE4 strain, the addition of 2 ccdB and 1 additional copy of gyrA (1 copy is already present) does not reduce the amount of protein produced and does not affect growth ability.

Example 5: Use of ccdB From *E. coli* O157

In order to validate that copies of the ccdB gene from another origin than the F plasmid may be used in the 2ccdB system, we constructed a strain containing a copy of ccdB from *E. coli* O157:1-17. The ccdB gene from *E. coli* O157:H7 has been chosen (1) because it has only 36% of homologies with the ccdB gene from the F plasmid (at amino acids level) and (2) because it is inhibited by the same CcdA protein from the F plasmid.

At first, a DNA fragment has been constructed containing the ccdBoi57 gene and a kanamycin resistance gene surrounded by 2 FRT sites allowing the excision of the resistance gene after insertion of the DNA fragment into the bacterial genome. This construction was ligated in a plasmid and transformed in B462 (a strain resistant to CcdB due to the presence of the gyrA462 mutation). In a second time, this fragment has been inserted between the yjjK and slt genes of *E. colii* W3110 containing a plasmid encoding ccdA under the control of the Pbad promoter to generate the new KW5 strain (W3110 yjjK ::FRTccdB$_{O157}$) after removal of the resistance gene. This strain grows as the WT strain and the ccdB$_{O157}$ gene kills bacteria as expected when the Pbad promoter is repressed (in the absence of arabinose). These results show that it is possible to construct a strain using the ccdB$_{O157}$ gene. The CcdB$_{O157}$ protein product is counteracted by the F plasmid CcdA and usable in the present invention.

Example 6: Further Modifications of the Host Cell of the Invention

We next tested the applicability of the 2ccdB system to a bacterial strain comprising a genetically modified phage comprising an expression system, and wherein the Q, S, R and Rz genes are deleted. The deletion of these genes prevents lysis of the host cell when accidental reactivation of the phage occurs.

A DNA fragment containing the kanamycin resistance gene with 2 FRT sites and surrounded by the region bordering the Q, S, R and Rz genes in order to allow their deletion by homologous recombination (as previously described in WO2013004817) was transduced in the SE2 strain [BL21(DE3) dcm::FRTccdB] to generate the strain BL21(DE3) dcm::FRTccdB QSRRz::FRT after removal of the kanamycin resistance gene. In a second time, another fragment encoding yjjK::FRTkanFRTccdB has been transduced in the BL21(DE3) dcm::FRTccdB QSRRz::FRT to generate the SE5 [BL21(DE3) dcm::FRTccdB yjjK::FRTccdB QSRRz::FRT] after removal of the kanamycin resistance gene. This final strain contains 2 ccdB genes as described above and the deletion of the Q, S, R, Rz genes avoiding bacterial lysis.

The SE5 strain has been compared to its unmodified-QSSRz homologous strain (SE3). There are growing both at the same rate of the SE1 strain and the production of a control protein (TraG) gave also the same results.

The invention claimed is:

1. Bacterial host cell comprising at least 2 chromosomal copies of a nucleic acid sequence encoding a poison protein, provided that said at least 2 copies are in a different replicon than a nucleic acid sequence encoding the antidote protein to the poison protein, wherein said cell further comprises at least one copy of a nucleic acid sequence encoding the antidote protein to the poison protein, and wherein said nucleic acid sequence encoding the antidote protein is carried by a plasmid further comprising an expression system wherein a nucleic acid sequence encoding a recombinant peptide, polypeptide or protein of interest is or may be inserted.

2. Host cell according to claim 1, wherein said poison protein is CcdB, encoded by SEQ ID NO: 1 or any nucleic acid sequence having at least 75% identity with SEQ ID NO: 1.

3. Host cell according to claim 1, wherein said antidote protein is CcdA, encoded by SEQ ID NO: 13 or any nucleic acid sequence having at least 75% identity with SEQ ID NO: 13.

4. Host cell according to claim 1, wherein said expression system comprises a promoter selected from the group comprising a T7 promoter, Ptrc, Para and Plac.

5. Host cell according to claim 1, wherein said expression system comprises a T7 promoter and the host cell further comprises a T7 RNA polymerase gene.

6. Host cell according to claim 1, wherein said expression system comprises a T7 promoter and the host cell further comprises a genetically modified phage inserted within its genome.

7. Host cell according to claim 1, wherein said expression system comprises a T7 promoter and the host cell further comprises a genetically modified phage defined as a phage wherein:
 a T7 expression system is inserted,
 the S, R, and/or the Q genes are inactivated, and
 the Int and/or Xis gene are inactivated.

8. Host cell according to claim 1, further comprising inactivation of at least one of the genes conA, galK, araB, araA, lon, ompT, rcsA, hsdR, mrr, endA and recA.

9. Host cell according to claim 1, further comprising at least two copies of a nucleic acid sequence encoding a functional GyrA protein.

10. A kit comprising:
 a host cell comprising at least 2 chromosomal copies of a nucleic acid sequence encoding a poison protein, provided that said at least 2 copies are in a different replicon than a nucleic acid sequence encoding the antidote protein to the poison protein, and
 a vector comprising at least one copy of the nucleic acid sequence encoding the antidote protein and at least one copy of an expression system wherein a nucleic acid sequence encoding a recombinant peptide, polypeptide or protein of interest is or may be inserted.

11. The kit according to claim 10, wherein the nucleic acid sequence encoding a peptide, polypeptide or protein of interest is under the control of a promoter selected from the group comprising a T7 promoter, Ptrc, Para and Plac.

12. A method for producing a recombinant peptide, polypeptide or protein of interest, wherein said method comprises:
 cultivating the host cell of claim 1, wherein the host cell further comprises at least one copy of the nucleic acid sequence encoding the peptide, polypeptide or protein of interest,
 and recovering the peptide, polypeptide or protein of interest.

13. The method according to claim 12, wherein the recombinant protein is a secreted protein, a transmembrane protein or a protein which is toxic for the bacterial strain.

14. The host cell of claim 5, wherein the T7 RNA polymerase gene is inserted in a genome of the host cell.

15. The host cell of claim 5, wherein the T7 RNA polymerase gene is inserted in a genome of the host cell in a T7 expression system.

* * * * *

SEQUENCE LISTING

<160> NUMBER OF SEQ ID NOS: 19

<210> SEQ ID NO 1
<211> LENGTH: 306
<212> TYPE: DNA
<213> ORGANISM: Escherichia coli
<220> FEATURE:
<223> OTHER INFORMATION: ccdB

<400> SEQUENCE: 1

```
atgcagttta aggtttacac ctataaaaga gagagccgtt atcgtctgtt tgtggatgta      60
cagagtgata ttattgacac gcccgggcga cggatggtga tcccccctggc cagtgcacgt   120
ctgctgtcag ataaagtctc ccgtgaactt tacccggtgg tgcatatcgg ggatgaaagc   180
tggcgcatga tgaccaccga tatggccagt gtgccggtct ccgttatcgg ggaagaagtg   240
gctgatctca gccaccgcga aaatgacatc aaaaacgcca ttaacctgat gttctgggga   300
atataa                                                              306
```

<210> SEQ ID NO 2
<211> LENGTH: 2244
<212> TYPE: DNA
<213> ORGANISM: Escherichia coli
<220> FEATURE:
<223> OTHER INFORMATION: tonA DNA

<400> SEQUENCE: 2

```
atggcgcgtt ccaaaactgc tcagccaaaa cactcactgc gtaaaatcgc agttgtagta      60
gccacagcgg ttagcggcat gtctgtttat gcacaggcag cggttgaacc gaaagaagac   120
actatcaccg ttaccgctgc acctgcgccg caagaaagcg catgggggcc tgctgcaact   180
attgcggcgc gacagtctgc taccggcact aaaaccgata cgccgattca aaaagtgcca   240
cagtctattt ctgttgtgac cgccgaagag atggcgctgc atcagccgaa gtcggtaaaa   300
gaagcgctta gctacacgcc gggtgtctct gttggtacgc gtggcgcatc aaacacctat   360
gaccacctga tcattcgcgg ctttgcggca gaaggccaaa gccagaataa ctatctgaat   420
ggcctgaagt tgcagggcaa cttctataac gatgcggtca ttgacccgta tatgctggaa   480
cgcgctgaaa ttatgcgtgg cccggtttcc gtgctttacg gtaaaagcag tcctggcggc   540
ctgttgaata tggtcagcaa gcgtccgacc accgaaccgc tgaaagaagt tcagtttaaa   600
gccggtactg acagcctgtt ccagactggt tttgacttta gcgattcgtt ggatgatgac   660
ggtgtttact cttatcgcct gaccggtctt gcgcgttctg ccaatgccca gcagaaaggg   720
tcagaagagc agcgttatgc tattgcaccg gcgttcacct ggcgtccgga tgataaaacc   780
aattttacct tcctttctta cttccagaac gagccggaaa ccggttatta cggctggttg   840
ccgaaagagg gaaccgttga gccgctgccg aacggtaagc gtctgccgac agactttaat   900
gaagggggcga agaacaacac ctattctcgt aatgagaaga tggtcggcta cagcttcgat   960
cacgaattta acgacacctt tactgtgcgt cagaacctgc gctttgctga aacaaaaacc  1020
tcgcaaaaca gcgtttatgg ttacggcgtc tgctccgatc cggcgaatgc ttacagcaaa  1080
cagtgtgcgg cattagcgcc agcggataaa ggccattatc tggcacgtaa atacgtcgtt  1140
gatgatgaga agctgcaaaa cttctccgtt gatacccagt gcagagcaa gtttgccact  1200
ggcgatatcg accacaccct gctgaccggt gtcgacttta tgcgtatgcg taatgacatc  1260
aacgcctggt ttggttacga cgactctgtg ccactgctca atctgtacaa tccggtgaat  1320
accgatttcg acttcaatgc caaagatccg gcaaactccg gcccttaccg cattctgaat  1380
```

```
aaacagaaac aaacgggcgt ttatgttcag gatcaggcgc agtgggataa agtgctggtc    1440
accctaggcg gtcgttatga ctgggcagat caagaatctc ttaaccgcgt tgccgggacg    1500
accgataaac gtgatgacaa acagtttacc tggcgtggtg gtgttaacta cctgtttgat    1560
aatggtgtaa cacctlactt cagctatagc gaatcgtttg aaccttcttc gcaagttggg    1620
aaggatggta atattttcgc accgtctaaa ggtaagcagt atgaagtcgg cgtgaaatat    1680
gtaccggaag atcgtccgat tgtagttact ggtgccgtgt ataatctcac taaaaccaac    1740
aacctgatgg cggaccctga gggttccttc ttctcggttg aaggtggcga gatccgcgca    1800
cgtggcgtag aaatcgaagc gaaagcggcg ctgtcggcga gtgttaacgt agtcggttct    1860
tatacttaca ccgatgcgga atacaccacc gatactacct ataaaggcaa tacgcctgca    1920
caggtgccaa acacatggc ttcgttgtgg gctgactaca ccttctttga cggtccgctt    1980
tcaggtctga cgctgggcac cggtggtcgt tatactggct ccagttatgg tgatccggct    2040 aactcctta aagtgggaag ttatacggtc gtggatgcgt tagtacgtta tgatctggcg    2100
cgagtcggca tggctggctc caacgtggcg ctgcatgtta caacctgtt cgatcgtgaa    2160 tacgtcgcca gctgctttaa cacttatggc tgcttctggg gcgcagaacg tcaggtcgtt    2220
gcaaccgcaa ccttccgttt ctaa                                          2244

<210> SEQ ID NO 3
<211> LENGTH: 1149
<212> TYPE: DNA
<213> ORGANISM: Escherichia coli
<220> FEATURE:
<223> OTHER INFORMATION: galK DNA

<400> SEQUENCE: 3
atgagtctga agaaaaaaac acaatctctg tttgccaacg catttggcta ccctgccact    60
cacaccattc aggcgcctgg ccgcgtgaat ttgattggtg aacacaccga ctacaacgac    120
ggtttcgttc tgcccctgcgc gattgattat caaaccgtga tcagttgtgc accacgcgat    180
gaccgtaaag ttcgcgtgat ggcagccgat tatgaaaatc agctcgacga gttttccctc    240
gatgcgccca ttgtcgcaca tgaaaactat caatgggcta actacgttcg tggcgtggtg    300
aaacatctgc aactgcgtaa caacagcttg gcggcgtgg acatggtgat cagcggcaat    360
gtgccgcagg gtgccgggtt aagttcttcc gcttcactgg aagtcgcggt cggaaccgta    420
ttgcagcagc tttatcatct gccgctggac ggcgcacaaa tcgcgcttaa cggtcaggaa    480
gcagaaaacc agtttgtagg ctgtaactgc gggatcatgg atcagctaat ttccgcgctc    540
ggcaagaaag atcatgcctt gctgatcgat tgccgctcac tggggaccaa agcagtttcc    600
atgcccaaag gtgtggctgt cgtcatcatc aacagtaact tcaaacgtac cctggttggc    660
agcgaataca cacccgtcg tgaacagtgc gaaaccggtg cgcgtttctt ccagcagcca    720
gccctgcgtg atgtcaccat tgaagagttc aacgctgttg cgcatgaact ggacccgatc    780
gtggcaaaac gcgtgcgtca tatactgact gaaaacgccc gcaccgttga agctgccagc    840
gcgctggagc aaggcgacct gaaacgtatg ggcgagttga tggcggagtc tcatgcctct    900
atgcgcgatg atttcgaaat caccgtgccg caaattgaca ctctggtaga aatcgtcaaa    960
gctgtgattg cgacaaagg tggcgtacgc atgaccggcg gcggatttgg cggctgtatc    1020
gtcgcgctga tccggaaga gctggtgcct gccgtacagc aagctgtcgc tgaacaatat    1080
gaagcaaaaa caggtattaa agagactttt tacgtttgta accatcaca aggagcagga    1140
```

```
cagtgctga                                                                    1149
```

<210> SEQ ID NO 4
<211> LENGTH: 1701
<212> TYPE: DNA
<213> ORGANISM: Escherichia coli
<220> FEATURE:
<223> OTHER INFORMATION: araB DNA

<400> SEQUENCE: 4

```
atggcgattg caattggcct cgattttggc agtgattctg tgcgagcttt ggcggtggac     60
tgcgctaccg gtgaagagat cgccaccagc gtagagtggt atccccgttg cagaaaggg     120
caattttgtg atgccccgaa taaccagttc cgtcatcatc cgcgtgacta cattgagtca    180
atggaagcgg cactgaaaac cgtgcttgca gagcttagcg tcgaacagcg cgcagctgtg    240
gtcgggattg gcgttgacag taccggctcg acgcccgcac cgattgatgc cgacggaaac    300
gtgctggcgc tgcgcccgga gtttgccgaa aacccgaacg cgatgttcgt attgtggaaa    360
gaccacactg cggttgaaga gcggaagag attacccgtt tgtgccacgc gccgggcaac     420
gttgactact cccgctacat tggtggtatt tattccagcg aatggttctg ggcaaaaatc    480
ctgcatgtga ctcgccagga cagcgccgtg gcgcaatctg ccgcatcgtg gattgagctg    540
tgcgactggg tgccagctct gctttccggt accaccccgcc cgcaggatat tcgtcgcgga    600
cgttgcagcg ccgggcataa atctctgtgg cacgaaagct ggggcggcct gccgccagcc    660
agtttctttg atgagctgga cccgatcctc aatcgccatt tgccttcccc gctgttcact    720
gacacttgga ctgccgatat tccggtgggc accttatgcc cggaatgggc gcagcgtctc    780
ggcctgcctg aaagcgtggt gatttccggc ggcgcgtttg actgccatat gggcgcagtt    840
ggcgcaggcg cacagcctaa cgcactggta aaagttatcg gtacttccac ctgcgacatt    900
ctgattgccg acaaacagag cgttggcgag cgggcagtta aaggtatttg cggtcaggtt    960
gatggcagcg tggtgcctgg atttatcggt ctggaagcag gccaatcggc gtttggtgat   1020
atctacgcct ggtttggtcg cgtactcggc tggccgctgg aacagcttgc cgcccagcat   1080
ccggaactga aaacgcaaat caacgccagc cagaaacaac tgcttccggc gctgaccgaa   1140
gcatgggcca aaaatccgtc tctggatcac ctgccggtgg tgctcgactg gtttaacggc   1200
cgccgcacac cgaacgctaa ccaacgcctg aaaggggtga ttaccgatct taacctcgct   1260
accgacgctc cgctgctgtt cggcggtttg attgctgcca ccgcctttgg cgcacgcgca   1320
atcatggagt gctttaccga tcaggggatc gccgttaata acgtgatggc actgggcggc   1380
atcgcgcgga aaaaccaggt cattatgcag gcctgctgcg acgtgctgaa tcgcccgctg   1440
caaattgttg cctctgacca gtgctgtgcg ctcggtgcgg cgattttgc tgccgtcgcc   1500
gcgaaagtgc acgcagacat cccatcagct cagcaaaaaa tggccagtgc ggtagagaaa   1560
accctgcaac cgtgcagcga gcaggcacaa cgctttgaac agctttatcg ccgctatcag   1620
caatgggcga tgagcgccga acaacactat cttccaactt ccgccccggc acaggctgcc   1680
caggccgttg cgactctata a                                             1701
```

<210> SEQ ID NO 5
<211> LENGTH: 1503
<212> TYPE: DNA
<213> ORGANISM: Escherichia coli
<220> FEATURE:
<223> OTHER INFORMATION: araA DNA

<400> SEQUENCE: 5

-continued

```
atgacgattt ttgataatta tgaagtgtgg tttgtcattg gcagccagca tctgtatggc    60
ccggaaaccc tgcgtcaggt cacccaacat gccgagcacg tcgttaatgc gctgaatacg   120
gaagcgaaac tgccctgcaa actggtgttg aaaccgctgg gcaccacgcc ggatgaaatc   180
accgctattt gccgcgacgc gaattacgac gatcgttgcg ctggtctggt ggtgtggctg   240
cacaccttct ccccggccaa aatgtggatc aacggcctga ccatgctcaa caaaccgttg   300
ctgcaattcc acaccagtt caacgcggcg ctgccgtggg acagtatcga tatggacttt    360
atgaacctga accagactgc acatggcggt cgcgagttcg gcttcattgg cgcgcgtatg   420
cgtcagcaac atgccgtggt taccggtcac tggcaggata acaagcccca tgagcgtatc   480
ggctcctgga tgcgtcaggc ggtctctaaa caggatacccc gtcatctgaa agtctgccga   540
tttggcgata acatgcgtga agtggcggtc accgatggcg ataaagttgc cgcacagatc   600
aagttcggtt ctccgtcaa tacctgggcg gttggcgatc tggtgcaggt ggtgaactcc    660
atcagcgacg gcgatgttaa cgcgctggtc gatgagtacg aaagctgcta caccatgacg   720
cctgccacac aaatccacgg caaaaaacga cagaacgtgc tggaagcggc gcgtattgag   780
ctggggatga agcgtttcct ggaacaaggt ggcttccacg cgttcaccac caccctttgaa   840
gatttgcacg gtctgaaaca gcttcctggt ctggccgtac agcgtctgat gcagcagggt   900
tacggctttg cgggcgaagg cgactggaaa actgccgccc tgcttcgcat catgaaggtg   960
atgtcaaccg gtctgcaggg cggcacctcc tttatggagg actacaccta tcacttcgag  1020
aaaggtaatg acctggtgct cggctcccat atgctgaaag tctgcccgtc gatcgccgca  1080
gaagagaaac cgatcctcga cgttcagcat ctcggtattg gtggtaagga cgatcctgcc  1140
cgcctgatct tcaatacccca aaccggccca gcgattgtcg ccagcttgat tgatctcggc  1200
gatcgttacc gtctactggt taactgcatc gacacggtga aaacaccgca ctccctgccg  1260
aaactgccgg tggcgaatgc gctgtggaaa gcgcaaccgg atctgccaac tgcttccgaa  1320
gcgtggatcc tcgctggtgg cgcgcaccat accgtcttca gccatgcact gaacctcaac  1380
gatatgcgcc aattcgccga gatgcacgac attgaaatca cggtgattga taacgacaca  1440
cgcctgccag cgtttaaaga cgcgctgcgc tggaacgaag tgtattacgg gtttcgtcgc  1500
taa                                                                1503
```

<210> SEQ ID NO 6
<211> LENGTH: 2355
<212> TYPE: DNA
<213> ORGANISM: Escherichia coli
<220> FEATURE:
<223> OTHER INFORMATION: lon DNA

<400> SEQUENCE: 6

```
atgaatcctg agcgttctga acgcattgaa atccccgtat tgccgctgcg cgatgtggtg    60
gtttatccgc acatggtcat ccccttattg gtcgggcggg aaaaatctat ccgttgtctg   120
gaagcggcga tggaccatga taaaaaaatt atgctggtcg cgcagaaaga agcttcaacg   180
gatgagccgg gtgtaaacga tcttttcacc gtcgggaccg tggcctctat attgcagatg   240
ctgaaactgc ctgacggcac cgtcaaagtg ctggtcgagg ggttacagcg cgcgcgtatt   300
tctgcgctct ctgacaatgg cgaacacttt tctgcgaagg cggagtatct ggagtcgccg   360
accattgatg agcgggaaca ggaagtgctg gtgcgtactg caatcagcca gttcgaaggc   420
tacatcaagc tgaacaaaaa aatcccacca gaagtgctga cgtcgctgaa tagcatcgac   480
```

```
gatccggcgc gtctggcgga taccattgct gcacatatgc cgctgaaact ggctgacaaa      540
cagtctgttc tggagatgtc cgacgttaac gaacgtctgg aatatctgat ggcaatgatg      600
gaatcggaaa tcgatctgct gcaggttgag aaacgcattc gcaaccgcgt taaaaagcag      660
atggagaaat cccagcgtga gtactatctg aacgagcaaa tgaaagctat tcagaaagaa      720
ctcggtgaaa tggacgacgc gccggacgaa aacgaagccc tgaagcgcaa aatcgacgcg      780
gcgaagatgc cgaaagaggc aaaagagaaa gcggaagcag agttcagaa gctgaaaatg      840 atgtctccga tgtcggcaga agcgaccgta gtgcgtggtt atatcgactg gatggtacag      900
gtgccgtgga atgcgcgtag caaggtcaaa aaagacctgc gtcaggcgca ggaaatcctt      960
gataccgacc attatggtct ggagcgcgtg aaagatcgaa tccttgagta tcttgcggtt     1020
caaagccgtg tcaacaaaat caagggaccg atcctctgcc tggtaggggcc gccgggggta     1080 ggtaaaacct ctcttggtca gtccattgcc aaagccaccg gcgtaaaata tgtccgtatg     1140
gcgctgggcg gcgtgcgtga tgaagcgaaa atccgtggtc accgccgtac ttacatcggt     1200
tctatgccgg gtaaactgat ccagaaaatg gcgaaagtgg cgtgaaaaa cccgctgttc     1260 ctgctcgatg agatcgacaa aatgtcttct gacatgcgtg gcgatccggc ctctgcactg     1320
cttgaagtgc tggatccaga gcagaacgta gcgttcagcg accactacct ggaagtggat     1380
tacgatctca gcgacgtgat gtttgtcgcg acgtcgaact ccatgaacat tccggcaccg     1440
ctgctggatc gtatgaagt gattcgcctc tccggttata ccgaagatga aaaactgaac     1500
atcgccaaac gtcacctgct gccgaagcag attgaacgta atgcactgaa aaaggtgag     1560 ctgaccgtcg acgatagcgc cattatcggc attattcgtt actacacccg tgaggcgggc     1620
gtgcgtggtc tggagcgtga atctccaaa ctgtgtcgca aagcggttaa gcagttactg     1680
ctcgataagt cattaaaaca tatcgaaatt aacggcgata acctgcatga ctatctcggt     1740
gttcagcgtt tcgactatgg tcgcgcggat aacgaaaacc gtgtcggtca ggtaaccggt     1800
ctggcgtgga cggaagtggg cggtgacttg ctgaccattg aaaccgcatg tgttccgggt     1860
aaaggcaaac tgacctatac cggttcgctc ggcgaagtga tgcaggagtc cattcaggcg     1920
gcgttaacgg tggttcgtgc gcgtgcgaa aaactgggga tcaaccctga ttttacgaa     1980 aaacgtgaca tccacgtcca cgtaccggaa ggtgcgacgc cgaaagatgg tccgagtgcc     2040
ggtattgcta tgtgcaccgc gctggttttct tgcctgaccg gtaacccggt tcgtgccgat     2100
gtggcaatga ccggtgagat cactctgcgt ggtcaggtac tgccgatcgg tggtttgaaa     2160
gaaaaactcc tggcagcgca tcgcggcggg attaaaacag tgctaattcc gttcgaaaat     2220
aaacgcgatc tggaagagat tcctgacaac gtaattgccg atctggacat tcatcctgtg     2280
aagcgcattg aggaagttct gactctggcg ctgcaaaatg aaccgtctgg tatgcaggtt     2340
gtgactgcaa aatag                                                      2355
```

<210> SEQ ID NO 7
<211> LENGTH: 954
<212> TYPE: DNA
<213> ORGANISM: Escherichia coli
<220> FEATURE:
<223> OTHER INFORMATION: ompT DNA

<400> SEQUENCE: 7

```
atgcgggcga aacttctggg aatagtcctg acaaccccta ttgcgatcag ctcttttgct        60
tctaccgaga ctttatcgtt tactcctgac aacataaatg cggacattag tcttggaact       120
ctgagcggaa aaacaaaaga gcgtgtttat ctagccgaag aaggaggccg aaaagtcagt       180
```

```
caactcgact ggaaattcaa taacgctgca attattaaag gtgcaattaa ttgggatttg      240
atgccccaga tatctatcgg ggctgctggc tggacaactc tcggcagccg aggtggcaat      300
atggtcgatc aggactggat ggattccagt aaccccggaa cctggacgga tgaaagtaga      360
caccctgata cacaactcaa ttatgccaac gaatttgatc tgaatatcaa aggctggctc      420
ctcaacgaac ccaattaccg cctgggactc atggccggat atcaggaaag ccgttatagc      480
tttacagcca gaggtggttc ctatatctac agttctgagg agggattcag agatgatatc      540
ggctccttcc cgaatggaga aagagcaatc ggctacaaac aacgttttaa aatgccctac      600
attggcttga ctggaagtta tcgttatgaa gattttgaac tcggtggcac atttaaatac      660
agcggctggg tggaatcatc tgataacgat gaacactatg acccgggaaa aagaatcact      720
tatcgcagta aggtcaaaga ccaaaattac tattctgttg cagtcaatgc aggttattac      780
gtcacaccta acgcaaaagt ttatgttgaa ggcgcatgga atcgggttac gaataaaaaa      840
ggtaatactt cactttatga tcacaataat aacacttcag actacagcaa aaatggagca      900
ggtatagaaa actataactt catcactact gctggtctta agtacacatt ttaa            954

<210> SEQ ID NO 8
<211> LENGTH: 624
<212> TYPE: DNA
<213> ORGANISM: Escherichia coli
<220> FEATURE:
<223> OTHER INFORMATION: rcsA DNA

<400> SEQUENCE: 8
atgtcaacga ttattatgga tttatgtagt tacacccgac taggtttaac cgggtatctg       60
ttgagtagag gggttaaaaa aagagaaatc aacgacattg aaaccgttga tgaccttgcc      120
atagcttgtg attcacagcg ccccttcagt gtgtttatta atgaggactg tttcatccac      180
gatgcttcta acagtcagcg tatcaagctc atcattaatc aacatcccaa tacgttattt      240
atcgttttta tggcaattgc caatgttcat tttgatgaat atctattggt cagaaaaaat      300
ttattgatca gttctaaatc gattaaaccg gaatctctcg acgatatcct ggcgatatt       360 ctgaaaaaag agacaacgat aacctcgttt ttaaatatgc cgacgttatc attgagccga      420
accgaatcga gtatgttgcg aatgtggatg gcaggtcagg gaaccattca aatctctgac      480
caaatgaata tcaaagccaa gaccgtttca tcgcataaag gtaatattaa acgtaagatc      540
aaaacgcata taaacaggt tatctaccat gtcgtccgac tgacggataa tgtgactaat      600 ggtattttg tcaacatgcg ctaa                                             624

<210> SEQ ID NO 9
<211> LENGTH: 3567
<212> TYPE: DNA
<213> ORGANISM: Escherichia coli
<220> FEATURE:
<223> OTHER INFORMATION: hsdR DNA

<400> SEQUENCE: 9
atgttatggg ccttaaatat ttggacaggc ccgcacagca atggattaat aacaatgatg       60
aataaatcca tttttgaatt cctgaagggc gtcaacgact tcacttatgc catcgcctgt      120
gcggcggaaa ataactaccc ggatgatccc aacacgacgc tgattaaaat gcgtatgttt      180
ggcgaagcca cagcgaaaca tcttggtctg ttactcaaca tccccccttg tgagaatcaa      240
cacgatctcc tgcgtgaact cggcaaaatc gcctttgttg atgacaacat cctctctgta      300
```

```
tttcacaaat tacgccgcat tggtaaccag gcggtgcacg aatatcataa cgatctcaac      360
gatgcccaga tgtgcctgcg actcgggttc cgcctggctg tctggtacta ccgtctggtc      420
actaaagatt atgacttccc ggtgccggtg tttgtgttgc cggaacgtgg tgaaaacctc      480
tatcaccaga aagtgctgac gctaaaacaa cagcttgaac agcaggtgcg agaaaaagcg      540
cagactcagg cagaagtcga agcgcaacag cagaagctgg ttgccctgaa cggctatatc      600
gccattctgg aaggcaaaca gcaggaaacc gaagcgcaaa cccaggctcg ccttgcggca      660
ctggaagcac agctcgccga agaacgcg gaactggcaa aacagaccga acaggaacgt       720
aaggcttacc acaaagaaat taccgatcag gccatcaagc gcacactcaa ccttagcgaa      780
gaagagagtc gcttcctgat tgatgcgcaa ctgcgtaaag caggctggca ggccgacagc      840
aaaaccctgc gcttctccaa aggcgcacgt ccggaacccg gcgtcaataa agccattgcc      900
gaatggccga ccggaaaaga tgaaacgggt aatcagggct tgcggatta tgtgctgttt       960 gtcggcctca aacccatcgc ggtggtagag gcgaaacgta acaatatcga cgttcccgcc     1020
aggctcaatg agtcgtatcg ctacagtaaa tgtttcgata atggcttcct gcgggaaacc     1080
ttgcttgagc actactcacc ggatgaagtg catgaagcag tgccagagta tgaaaccagc     1140
tggcaggaca ccagcggcaa acaacggttt aaaatcccct tctgctactc gaccaacggg     1200
cgcgaatacc gcgcaacaat gaagaccaaa agcggcatct ggtatcgcga cgtgcgtgat     1260
acccgcaata tgtcgaaagc cttacccgag tggcaccgcc cggaagagct gctggaaatg     1320
ctcggcagcg aaccgcaaaa acagaatcag tggtttgccg ataaccctgg catgagcgag     1380
ctgggcctgc gttattatca ggaagatgcc gtccgcgcgg ttgaaaaggc aatcgtcaag     1440
gggcaacaag agatcctgct ggcgatggcg accggtaccg gtaaaacccg tacggcaatc     1500
gccatgatgt tccgcctgat ccagtcccag cgttttaaaac gcattctctt ccttgtcgac     1560
cgccgttctc ttggcgaaca ggcgctgggc gcgtttgaag atacgcgtat taacggcgac     1620
accttcaaca gcattttcga cattaaaggg ctgacggata aattcccgga agacagcacc     1680
aaaattcacg ttgccaccgt acagtcgctg gtgaaacgca ccctgcaatc agatgaaccg     1740
atgccggtgg cccgttacga ctgtatcgtc gttgacgaag cgcatcgcgg ctatattctc     1800
gataaagagc agaccgaagg cgaactgcag ttccgcagcc agctggatta cgtctctgcc     1860
taccgtcgca ttctcgatca cttcgatgcg gtaaaaatcg ctctcaccgc cacccccggcg     1920 ctacatactg tgcagatttt cggcgagccg gtttaccgtt atacctaccg taccgcggtt     1980
atcgacggtt ttctgatcga ccaggatccg cctattcaga tcatcacccg caacgcgcag     2040
gaggggtttt atctctccaa aggcgagcag gtagagcgca tcagcccgca gggagaagtg     2100
atcaatgaca ccctggaaga cgatcaggat tttgaagtcg ccgactttaa ccgtggcctg     2160
gtgatcccgg cgtttaaccg cgccgtctgt aacgaactca ccaattatct tgacccgacc     2220
ggatcgcaaa aaacgctggt cttctgcgtc accaatgccc atgccgatat ggtggtggaa     2280
gagctgcgtg ccgcgttcaa gaaaaagtat ccgcaactgg agcacgacgc gatcatcaag     2340
atcaccggtg atgccgataa agacgcgcgc aaagtgcaga ccatgatcac ccgcttcaat     2400
aaagagcggt gcccaatat cgtggtaacc gtcgacctgc tgacgaccgg cgtcgatatt     2460
ccgtcgatct gtaatatcgt gttcctgcgt aaagtacgca gccgcattct gtacgaacag     2520
atgaaaggcc gcgccacgcg cttatgcccg gaggtgaata aaaccagctt taagattttt     2580
gactgtgtcg atatctacag cacgctggag agcgtcgaca ccatgcgtcc ggtggtggtg     2640
cgcccgaagg tggaactgca aacgctggtc aatgaaatta ccgattcaga aacctataaa     2700
```

```
atcaccgaag cggatggccg cagttttgcc gagcacagcc atgaacaact ggtggcgaag    2760
ctccagcgta tcatcggtct ggccacgttt aaccgtgacc gcagcgaaac gatagataaa    2820
caggtgcgtc gtctggatga gctatgccag gacgcggcgg gcgtgaactt aacggcttc     2880 gcctcgcgcc tgcgggaaaa agggccgcac tggagcgccg aagtctttaa caaactgcct    2940
ggctttatcg cccgtctgga aaagctgaaa acggacatca acaacctgaa tgatgcgccg    3000
atcttcctcg atatcgacga tgaagtggtg agtgtaaaat cgctgtacgg tgattacgac    3060
acgccgcagg atttcctcga agcctttgac tcgctggtgc aacgttcccc gaacgcgcaa    3120
ccggcattgc aggcagttat taatcgcccg cgcgatctca cccgtaaagg ctggtcgag     3180 ctacaggagt ggtttgaccg ccagcacttt gaggaatctt ccctgcgcaa agcatggaaa    3240
gagacgcgca atgaagatat cgccgccggg ctgattggtc atattcgccg cgctgcggtg    3300
ggcgatgcgc tgaaaccgtt tgaggaacgt gtcgatcacg cgctgacgcg cattaagggc    3360
gaaaacgact ggagcagcga gcaattaagc tggctcgatc gtttagcgca ggcgctgaaa    3420
gagaaagtgg tgctcgacga cgatgtcttc aaaaccggca acttccaccg tcgcggcggg    3480
aaggcgatgc tgcaaagaac ctttgacgat aatctcgata ccctgctggg caaattcagc    3540
gattatatct gggacgagct ggcctga                                        3567
```

<210> SEQ ID NO 10
<211> LENGTH: 915
<212> TYPE: DNA
<213> ORGANISM: Escherichia coli
<220> FEATURE:
<223> OTHER INFORMATION: mrr DNA

<400> SEQUENCE: 10

```
atgacggttc ctacctatga caaatttatt gaacctgttc tgcgttatct ggcaacaaaa     60
ccggaaggtg cagccgcgcg tgatgttcat gaggctgccg cggatgcatt aggactggat    120
gacagccagc gagcgaaagt cattaccagc ggacaacttg tttataaaaa tcgtgcaggc    180
tgggcgcatg accgtttaaa acgtgccggg ttgtcgcaaa gtttgtcgcg tggcaaatgg    240
tgcctgactc ctgcgggttt tgactgggtt gcgtctcatc cccagccaat gacggagcag    300
gagacgaacc atctggcctt cgcttttgtg aatgtcaaac ttaagtcacg gccggatgcc    360
gtcgatttag atccgaaagc cgactctccc gatcatgaag aacttgcaaa gagcagcccg    420
gacgatcggt tagatcaggc gctaaaagag cttcgtgatg cggtggctga tgaggttctg    480
gaaaacttat tgcaggtttc tccttcgcgc tttgaagtca ttgttctgga tgttttgcat    540
cgcctggggt atggcggcca ccgtgatgat ttgcagcgtg ttggcggtac tggagatggt    600
ggcatcgatg gtgtgatatc gcttgataaa cttggcctgg agaaagttta tgttcaggca    660
aaacgttggc agaatactgt aggcaggcca gaattacagg cattttacgg cgcactggct    720
gggcaaaaag cgaaacgtgg ggtgtttatt accacttctg gatttacttc tcaggcgcgt    780
gactttgccc aatccgtcga gggtatggtg ttggttgatg gggaacgcct ggtgcactta    840
atgatcgaaa acgaagtagg ggtttcttca cgtttgttga aggtgccgaa actggatatg    900
gactattttg agtga                                                     915
```

<210> SEQ ID NO 11
<211> LENGTH: 708
<212> TYPE: DNA
<213> ORGANISM: Escherichia coli
<220> FEATURE:

<223> OTHER INFORMATION: endA DNA

<400> SEQUENCE: 11

| | | | | | |
|---|---|---|---|---|---|
| atgtaccgtt | atttgtctat | tgctgcggtg | gtactgagcg | cagcatttc | cggcccggcg | 60 |
| ttggccgaag | gtatcaatag | tttttctcag | gcgaaagccg | cggcggtaaa | agtccacgct | 120 |
| gacgcgcccg | gtacgtttta | ttgcggatgt | aaaattaact | ggcagggcaa | aaaaggcgtt | 180 |
| gttgatctgc | aatcgtgcgg | ctatcaggtg | cgcaaaaatg | aaaaccgcgc | cagccgcgta | 240 |
| gagtgggaac | atgtcgttcc | cgcctggcag | ttcggtcacc | agcgccagtg | ctggcaggac | 300 |
| ggtggacgta | aaaactgcgc | taaagatccg | gtctatcgca | agatggaaag | cgatatgcat | 360 |
| aacctgcagc | cgtcagtcgg | tgaggtgaat | ggcgatcgcg | gcaactttat | gtacagccag | 420 |
| tggaatggcg | gtgaaggcca | gtacggtcaa | tgcgccatga | aggtcgattt | caaagaaaaa | 480 |
| gctgccgaac | caccagcgcg | tgcacgcggt | gccattgcgc | gcacctactt | ctatatgcgc | 540 |
| gaccaataca | acctgacact | ctctcgccag | caaacgcagc | tgttcaacgc | atggaacaag | 600 |
| atgtatccgg | ttaccgactg | ggagtgcgag | cgcgatgaac | gcatcgcgaa | ggtgcagggc | 660 |
| aatcataacc | cgtatgtgca | acgcgcttgc | caggcgcgaa | agagctaa | | 708 |

<210> SEQ ID NO 12
<211> LENGTH: 1062
<212> TYPE: DNA
<213> ORGANISM: Escherichia coli
<220> FEATURE:
<223> OTHER INFORMATION: recA DNA

<400> SEQUENCE: 12

| | | | | | |
|---|---|---|---|---|---|
| atggctatcg | acgaaaacaa | acagaaagcg | ttggcggcag | cactgggcca | gattgagaaa | 60 |
| caatttggta | aaggctccat | catgcgcctg | ggtgaagacc | gttccatgga | tgtgaaaacc | 120 |
| atctctaccg | gttcgctttc | actggatatc | gcgcttgggg | caggtggtct | gccgatgggc | 180 |
| cgtatcgtcg | aaatctacgg | accggaatct | tccggtaaaa | ccacgctgac | gctgcaggtg | 240 |
| atcgccgcag | cgcagcgtga | aggtaaaacc | tgtgcgttta | tcgatgctga | acacgcgctg | 300 |
| gacccaatct | acgcacgtaa | actgggcgtc | gatatcgaca | acctgctgtg | ctcccagccg | 360 |
| gacaccggcg | agcaggcact | ggaaatctgt | gacgccctgg | cgcgttctgg | cgcagtagac | 420 |
| gttatcgtcg | ttgactccgt | ggcggcactg | acgccgaaag | cggaaatcga | aggcgaaatc | 480 |
| ggcgactctc | acatgggcct | tgcggcacgt | atgatgagcc | aggcgatgcg | taagctggcg | 540 |
| ggtaacctga | gcagtccaa | cacgctgctg | atcttcatca | accagatccg | tatgaaaatt | 600 |
| ggtgtgatgt | tcggtaaccc | ggaaaccact | accggtggta | acgcgctgaa | attctacgcc | 660 |
| tctgttcgtc | tcgacatccg | tcgtatcggc | gcggtgaaag | agggcgaaaa | cgtggtgggt | 720 |
| agcgaaaccc | gcgtgaaagt | ggtgaagaac | aaaatcgctg | cgccgtttaa | acaggctgaa | 780 |
| ttccagatcc | tctacggcga | aggtatcaac | ttctacggcg | aactggttga | cctgggcgta | 840 |
| aaagagaagc | tgatcgagaa | agcaggcgcg | tggtacagct | acaaaggtga | aagatcggt | 900 |
| cagggtaaag | cgaatgcgac | tgcctggctg | aaagataacc | cggaaaccgc | gaaagagatc | 960 |
| gagaagaaag | tacgtgagtt | gctgctgagc | aacccgaact | caacgccgga | tttctctgta | 1020 |
| gatgatagcg | aaggcgtagc | agaaactaac | gaagattttt | aa | | 1062 |

<210> SEQ ID NO 13
<211> LENGTH: 219
<212> TYPE: DNA
<213> ORGANISM: Escherichia coli
<220> FEATURE:
<223> OTHER INFORMATION: CcdA DNA

<400> SEQUENCE: 13

| | | | | | |
|---|---|---|---|---|---|
| atgaagcagc | gtattacagt | gacagttgac | agcgacagct | atcagttgct | caaggcatat | 60 |
| gatgtcaata | tctccggtct | ggtaagcaca | accatgcaga | atgaagcccg | tcgtctgcgt | 120 |
| gccgaacgct | ggaaagcgga | aaatcaggaa | gggatggctg | aggtcgcccg | gtttattgaa | 180 |
| atgaacggct | cttttgctga | cgagaacagg | gactggtga | | | 219 |

<210> SEQ ID NO 14
<211> LENGTH: 29865
<212> TYPE: DNA
<213> ORGANISM: Artificial Sequence
<220> FEATURE:
<223> OTHER INFORMATION: phage P11

<400> SEQUENCE: 14

| | | | | | |
|---|---|---|---|---|---|
| gcttttttat | actaagttgg | cattataaaa | aagcattgct | tatcaatttg | ttgcaacgaa | 60 |
| caggtcacta | tcagtcaaaa | taaaatcatt | atttgatttc | aattttgtcc | cactccctgc | 120 |
| ctctgtcatc | acgatactgt | gatgccatgg | tgtccgactt | atgcccgaga | agatgttgag | 180 |
| caaacttatc | gcttatctgc | ttctcataga | gtcttgcaga | caaactgcgc | aactcgtgaa | 240 |
| aggtaggcgg | atccagatcc | cggacaccat | cgaatggcgc | aaaacctttc | gcggtatggc | 300 |
| atgatagcgc | ccggaagaga | gtcaattcag | ggtggtgaat | gtgaaaccag | taacgttata | 360 |
| cgatgtcgca | gagtatgccg | gtgtctctta | tcagaccgtt | tcccgcgtgg | tgaaccaggc | 420 |
| cagccacgtt | tctgcgaaaa | cgcgggaaaa | agtggaagcg | gcgatggcgg | agctgaatta | 480 |
| cattcccaac | cgcgtggcac | aacaactggc | gggcaaacag | tcgttgctga | ttggcgttgc | 540 |
| cacctccagt | ctggccctgc | acgcgccgtc | gcaaattgtc | gcggcgatta | aatctcgcgc | 600 |
| cgatcaactg | ggtgccagcg | tggtggtgtc | gatggtagaa | cgaagcggcg | tcgaagcctg | 660 |
| taaagcggcg | gtgcacaatc | ttctcgcgca | acgcgtcagt | gggctgatca | ttaactatcc | 720 |
| gctggatgac | caggatgcca | ttgctgtgga | agctgcctgc | actaatgttc | cggcgttatt | 780 |
| tcttgatgtc | tctgaccaga | cacccatcaa | cagtattatt | ttctcccatg | aagacggtac | 840 |
| gcgactgggc | gtggagcatc | tggtcgcatt | gggtcaccag | caaatcgcgc | tgttagcggg | 900 |
| cccattaagt | tctgtctcgg | cgcgtctgcg | tctggctggc | tggcataaat | atctcactcg | 960 |
| caatcaaatt | cagccgatag | cggaacggga | aggcgactgg | agtgccatgt | ccggttttca | 1020 |
| acaaaccatg | caaatgctga | atgagggcat | cgttcccact | gcgatgctgg | ttgccaacga | 1080 |
| tcagatggcg | ctgggcgcaa | tgcgcgccat | taccgagtcc | gggctgcgcg | ttggtgcgga | 1140 |
| tatctcggta | gtgggatacg | acgataccga | agacagctca | tgttatatcc | cgccgttaac | 1200 |
| caccatcaaa | caggattttc | gcctgctggg | gcaaaccagc | gtggaccgct | tgctgcaact | 1260 |
| ctctcagggc | caggcggtga | agggcaatca | gctgttgccc | gtctcactgg | tgaaaagaaa | 1320 |
| aaccaccctg | gcgcccaata | cgcaaaccgc | ctctccccgc | gcgttggccg | attcattaat | 1380 |
| gcagctggca | cgacaggttt | cccgactgga | aagcgggcag | tgagcgcaac | gcaattaatg | 1440 |
| taagttagct | cactcattag | gcaccccagg | ctttacactt | tatgcttccg | gctcgtataa | 1500 |
| tgtgtggaat | tgtgagcgga | taacaatttc | acacaggaaa | cagctatgac | catgattacg | 1560 |
| gattcactgg | ccgtcgtttt | acaacgtcgt | gactgggaaa | accctggcgt | tacccaactt | 1620 |
| aatcgccttg | cagcacatcc | ccctttcgcc | agctggcgta | atagcgaaga | ggcccgcacc | 1680 |

```
gatcgcccttt cccaacagtt gcgcagcctg aatggcgaat ggcgctttgc ctggtttccg    1740
gcaccagaag cggtgccgga aagctggctg gagtgcgatc ttcctgaggc cgatactgtc    1800
gtcgtcccct caaactggca gatgcacggt tacgatgcgc ccatctacac caacgtgacc    1860
tatcccatta cggtcaatcc gccgtttgtt cccacggaga atccgacggg ttgttactcg    1920
ctcacattta atgttgatga aagctggcta caggaaggcc agacgcgaat tattttttgat   1980
ggcgtcggga tctgatccgg atttactaac tggaagaggc actaaatgaa cacgattaac    2040
atcgctaaga acgacttctc tgacatcgaa ctggctgcta tcccgttcaa cactctggct    2100
gaccattacg gtgagcgttt agctcgcgaa cagttggccc ttgagcatga gtcttacgag    2160
atgggtgaag cacgcttccg caagatgttt gagcgtcaac ttaaagctgg tgaggttgcg    2220
gataacgctg ccgccaagcc tctcatcact accctactcc ctaagatgat gcacgcatc    2280
aacgactggt ttgaggaagt gaaagctaag cgcggcaagc gcccgacagc cttccagttc    2340
ctgcaagaaa tcaagccgga agccgtagcg tacatcacca ttaagaccac tctggcttgc    2400
ctaaccagtg ctgacaatac aaccgttcag gctgtagcaa gcgcaatcgg tcgggccatt    2460
gaggacgagg ctcgcttcgg tcgtatccgt gaccttgaag ctaagcactt caagaaaaac    2520
gttgaggaac aactcaacaa gcgcgtaggg cacgtctaca agaaagcatt tatgcaagtt    2580
gtcgaggctg acatgctctc taagggtcta ctcggtggcg aggcgtggtc ttcgtggcat    2640
aaggaagact ctattcatgt aggagtacgc tgcatcgaga tgctcattga gtcaaccgga    2700
atggttagct acaccgccaa aaatgctggc gtagtaggtc aagactctga gactatcgaa    2760
ctcgcacctg aatacgctga ggctatcgca acccgtgcag gtgcgctggc tggcatctct    2820
ccgatgttcc aaccttgcgt agttcctcct aagccgtgga ctggcattac tggtggtggc    2880
tattgggcta acgtcgtcg tcctctggcg ctggtgcgta ctcacagtaa gaaagcactg    2940
atgcgctacg aagacgttta catgcctgag gtgtacaaag cgattaacat tgcgcaaaac    3000
accgcatgga aaatcaacaa gaaagtccta gcggtcgcca acgtaatcac caagtggaag    3060
cattgtccgg tcgaggacat ccctgcgatt gagcgtgaag aactcccgat gaaaccggaa    3120
gacatcgaca tgaatcctga ggctctcacc gcgtggaaac gtgctgccgc tgctgtgtac    3180
cgcaaggaca aggctcgcaa gtctcgccgt atcagccttg agttcatgct tgagcaagcc    3240
aataagtttg ctaaccataa ggccatctgg ttcccttaca acatggactg gcgcggtcgt    3300
gtttacgctg tgtcaatgtt caacccgcaa ggtaacgata tgaccaaagg actgcttacg    3360
ctggcgaaag gtaaaccaat cggtaaggaa ggttactact ggctgaaaat ccacggtgca    3420
aactgtgcgg gtgtcgataa ggttccgttc cctgagcgca tcaagttcat tgaggaaaac    3480
cacgagaaca tcatggcttg cgctaagtct ccactggaga acacttggtg ggctgagcaa    3540
gattctccgt tctgcttcct tgcgttctgc tttgagtacg ctggggtaca gcaccacggc    3600
ctgagctata actgctccct tccgctggcg tttgacgggt cttgctctgg catccagcac    3660
ttctccgcga tgctccgaga tgaggtaggt ggtcgcgcgg ttaacttgct tcctagtgaa    3720
accgttcagg acatctacgg gattgttgct aagaaagtca acgagattct acaagcagac    3780
gcaatcaatg gaccgataaa cgaagtagtt accgtgaccg atgagaacac tggtgaaatc    3840
tctgagaaag tcaagctggg cactaaggca ctggctggtc aatggctggc ttacggtgtt    3900
actcgcagtg tgactaagcg ttcagtcatg acgctggctt acgggtccaa agagttcggc    3960
ttccgtcaac aagtgctgga agataccatt cagccagcta ttgattccgg caagggtctg    4020
atgttcactc agccgaatca ggctgctgga tacatggcta agctgatttg ggaatctgtg    4080
```

```
agcgtgacgg tggtagctgc ggttgaagca atgaactggc ttaagtctgc tgctaagctg   4140
ctggctgctg aggtcaaaga taagaagact ggagagattc ttcgcaagcg ttgcgctgtg   4200
cattgggtaa ctcctgatgg tttccctgtg tggcaggaat acaagaagcc tattcagacg   4260
cgcttgaacc tgatgttcct cggtcagttc cgcttacagc ctaccattaa caccaacaaa   4320
gatagcgaga ttgatgcaca caaacaggag tctggtatcg ctcctaactt tgtacacagc   4380
caagacggta gccaccttcg taagactgta gtgtgggcac acgagaagta cggaatcgaa   4440
tcttttgcac tgattcacga ctccttcggt accattccgg ctgacgctgc gaacctgttc   4500
aaagcagtgc gcgaaactat ggttgacaca tatgagtctt gtgatgtact ggctgatttc   4560
tacgaccagt tcgctgacca gttgcacgag tctcaattgg acaaaatgcc agcacttccg   4620
gctaaaggta acttgaacct ccgtgacatc ttagagtcgg acttcgcgtt cgcgtaacgc   4680
caaatcaata cgactccgga tccccttcga aggaaagacc tgatgctttt cgtgcgcgca   4740
taaaatacct tgatactgtg ccggatgaaa gcggttcgcg acgagtagat gcaattatgg   4800
tttctccgcc aagaatctct ttgcatttat caagtgtttc cttcattgat attccgagag   4860
catcaatatg caatgctgtt gggatggcaa ttttacgcc tgttttgctt tgctcgacat   4920
aaagatatcc atctacgata tcagaccact tcatttcgca taaatcacca actcgttgcc   4980
cggtaacaac agccagttcc attgcaagtc tgagccaaca tggtgatgat tctgctgctt   5040
gataaatttt caggtattcg tcagccgtaa gtcttgatct ccttacctct gattttgctg   5100
cgcgagtggc agcgacatgg tttgttgtta tatggcttc agctattgcc tctcggaatg   5160
catcgctcag tgttgatctg attaacttgg ctgacgccgc cttgccctcg tctatgtatc   5220
cattgagcat tgccgcaatt tcttttgtgg tgatgtcttc aagtggagca tcaggcagac   5280
ccctccttat tgctttaatt ttgctcatgt aatttatgag tgtcttctgc ttgattcctc   5340
tgctggccag gattttttcg tagcgatcaa gccatgaatg taacgtaacg gaattatcac   5400
tgttgattct cgctgtcaga ggcttgtgtt tgtgtcctga aaataactca atgttggcct   5460
gtatagcttc agtgattgcg attcgcctgt ctctgcctaa tccaaactct ttacccgtcc   5520
ttgggtccct gtagcagtaa tatccattgt ttcttatata aaggttaggg ggtaaatccc   5580
ggcgctcatg acttcgcctt cttcacactg gagggcaaag aagatttcca ataatcagaa   5640
caagtcggct cctgtttagt tacgagcgac attgctccgt gtattcactc gttgaaatga   5700
atacacagtg cagtgtttat tctgttattt atgccaaaaa taaaggccac tatcaggcag   5760
ctttgttgtt ctgtttacca agttctctgg caatcattgc cgtcgttcgt attgcccatt   5820
tatcgacata tttcccatct tccattacag gaaacatttc ttcaggctta accatgcatt   5880
ccgattgcag cttgcatcca ttgcatcgct tgaattgtcc acaccattga ttttatcaa   5940
tagtcgtagt catacggata gtcctggtat tgttccatca catcctgagg atgctcttcg   6000
aactcttcaa attcttcttc catatatcac ctcaaataag tggtttgctg cctaatttaa   6060
ttttctggcg accaacacaa gtcacaccca tttcactgcg tggcttgctg tagtaaatac   6120
ggttctgttt acgctcgact tcttctgcct tcttgcagcg aaggcttccg agtgatgctg   6180
ctttatctgc tctgacgcaa ccagagagct ttagcgcaat ttttcgcgcc agtgcttcat   6240
tactgcgtcg ctcggcaata agttctgctc tgcgagcttt gtagcggctt tttgccgtac   6300
ctttggattc tttccagaca atggttacca tgatggtctc ctttaagtgg ctttggcgca   6360
tgacgcgtcg aggtgcttat cttctcgatc gctgtcttgt agctgcaatt cgcgccatcc   6420
```

-continued

```
ccaaaaccac tcaagttctg gtctcaacgg ttaggttgag agtccgtcga tgttaaagag    6480
cctgccaatc tgttccgttt ggcttccagc gtcctgctga tggcttaaat ttaagacttc    6540
ttaatttatt ggtcaagtgc attttgaag aaaacttaat tttatgggcg tgaatttagt     6600
ttgtctttga tttttaacgg gaaataaaaa aggggcgaaa gccccttaag gaaggtttgc    6660
tagcttggca tcaacgacaa cgccaatgat tttacagttc ccattgattt caatcattgg    6720
gtattgtgga ttgagtggtt tcaggaattt tctaccggca tcaataacta acttttgaa    6780 tgtcgcctcg ttttctcctt caagtttggc gactaccagc tttccattac gtggttcgac    6840
ttctgggtcg acgagaataa tcatcccctc aggaatactc agtcctgccg gggcagtcat    6900
tgaatcgcct ttaacgtcga gccaaaaaga gtcttcagaa caatctaccg ttgtgtcgta    6960
ccagttatct attgcacgcc tatgatatgg ctctacagct tccatccaac atcctgcgct    7020
tacccaacta attagaggat acgaacctct tggatcatgc ctgctgtgat aggcaatgtt    7080
tgaaagacta tcctctcctt tcaacaggta atcaggggag cactgcaaag ccttggctaa    7140
ggccaatagg ttttcgccat tgggctcagt ttcagatcgc tcccattggg aaatagcaac    7200
attagacacg ccaaccatct tgccaagggc agcctgccta atcttgagtt cttttctgcg    7260
agcgcgaata cgctcaccca tcagttgtgt attcatagtt aagacatctt aaataaactt    7320
gacttaagat tcctttggtg gataatttaa gtgttcttta atttcggagc gagtctatgt    7380 acaaaaaga tgttattgac cacttcggaa cccagcgtgc tgttgctaaa gcactaggca    7440
ttagcgatgc agcagtctct cagtggaaag aagttatccc agagaaagac gcctatcgat    7500
tggaaatcgt tacagctggc gccctgaagt atcaagaaag tgcttaccgc caagcggcat    7560
aagcaaattg ctcttttaaca gttctggcct ttcacctcta accgggtgag caaacatcag    7620
cggcaaatcc attgggtgtg ccgctataac tcaatatcaa tataggtaaa ttaacaaatg    7680
gcacaagcaa gctacagcaa gccaacacag cgagaaattg atcgcgctga aactgattta    7740
ctcatcaacc tgtcaacgct tacccagcgc ggtctggcaa agatgattgg ctgtcatgaa    7800
tcgaagataa gcagaacgga ctggagattt attgcttcgg tcttgtgtgc tttcggaatg    7860
gcatcagaca tcagtccgat tagcagggct tttaagtatg cgcttgatgg actcacaaag    7920
aaaaaacgcc cggtgtgcaa gaccgagcgt tctgaacaaa tccagatgga gttctgaggt    7980
cattactgga tctatcaaca ggagtcatta tgacaaatac agcaaaaata ctcaacttcg    8040
gcagaggtaa ctttgccgga caggagcgta atgtggcaga tctcgatgat ggttacgcca    8100
gactatcaaa tatgctgctt gaggcttatt cgggcgcaga tctgaccaag cgacagttta    8160
aagtgctgct tgccattctg cgtaaaacct atgggtggaa taaaccaatg gacagaatca    8220
ccgattctca acttagcgag attacaaagt tacctgtcaa acggtgcaat gaagccaagt    8280
tagaactcgt cagaatgaat attatcaagc agcaaggcgg catgtttgga ccaaataaaa    8340
acatctcaga atggtgtatc cctcaaaacg agggaaaatc ccctaaaacg agggataaaa    8400
catccctcaa attgggggat tgctatccct caaaacaggg ggacacaaaa gacactatta    8460
caaaagaaaa aagaaaagat tattcgtcag agaattctgg cgaatcctct gaccagccag    8520
aaaacgacct ttctgtggtg aaaccggatg ctgcaattca gagcggcagc aagtggggga    8580
cagcagaaga cctgaccgcc gcagagtgga tgtttgacat ggtgaagact atcgcaccat    8640
cagccagaaa accgaatttt gctgggtggg ctaacgatat ccgcctgatg cgtgaacgtg    8700
acggacgtaa ccaccgcgac atgtgtgtgc tgttccgctg gcatgccag acaacttct     8760 ggtccggtaa cgtgctgagc ccggccaaac tccgcgataa gtggacccaa ctcgaaatca    8820
```

```
accgtaacaa gcaacaggca ggcgtgacag ccagcaaacc aaaactcgac ctgacaaaca   8880
cagactggat ttacggggtg gatctatgaa aaacatcgcc gcacagatgg ttaactttga   8940
ccgtgagcag atgcgtcgga tcgccaacaa catgccggaa cagtacgacg aaaagccgca   9000
ggtacagcag gtagcgcaga tcatcaacgg tgtgttcagc cagttactgg caactttccc   9060
ggcgagcctg gctaaccgtg accagaacga agtgaacgaa atccgtcgcc agtgggttct   9120
ggcttttcgg gaaaacggga tcaccacgat ggaacaggtt aacgcaggaa tgcgcgtagc   9180
ccgtcggcag aatcgaccat ttctgccatc acccgggcag tttgttgcat ggtgccggga   9240
agaagcatcc gttaccgccg gactgccaaa cgtcagcgag ctggttgata tggtttacga   9300
gtattgccgg aagcgaggcc tgtatccgga tgcggagtct tatccgtgga aatcaaacgc   9360
gcactactgg ctggttacca acctgtatca gaacatgcgg gccaatgcgc ttactgatgc   9420
ggaattacgc cgtaaggccg cagatgagct tgtccatatg actgcgagaa ttaaccgtgg   9480
tgaggcgatc cctgaaccag taaaacaact tcctgtcatg ggcggtagac ctctaaatcg   9540
tgcacaggct ctggcgaaga tcgcagaaat caaagctaag ttcggactga aggagcaag   9600
tgtatgacgg gcaaagaggc aattattcat tacctgggga cgcataatag cttctgtgcg   9660
ccggacgttg ccgcgctaac aggcgcaaca gtaaccagca taaatcaggc cgcggctaaa   9720
atggcacggg caggtcttct ggttatcgaa ggtaaggtct ggcgaacggt gtattaccgg   9780
tttgctacca gggaagaacg ggaaggaaag atgagcacga acctgatgaa caaactggat   9840
acgattggat tcgacaacaa aaaagacctg cttatctcgg tgggcgattt ggttgatcgt   9900
ggtgcagaga acgttgaatg cctggaatta atcacattcc cctggttcag agctgtacgt   9960
ggaaaccatg agcaaatgat gattgatggc ttatcagagc gtggaaacgt taatcactgg  10020
ctgcttaatg gcggtggctg gttctttaat ctcgattacg acaaagaaat tctggctaaa  10080
gctcttgccc ataaagcaga tgaacttccg ttaatcatcg aactggtgag caaagataaa  10140
aaatatgtta tctgccacgc cgattatccc tttgacgaat acgagtttgg aaagccagtt  10200
gatcatcagc aggtaatctg gaaccgcgaa cgaatcagca actcacaaaa cgggatcgtg  10260
aaagaaatca aggcgcgga cacgttcatc tttggtcata cgccagcagt gaaaccactc  10320
aagtttgcca accaaatgta tatcgatacc ggcgcagtgt tctgcggaaa cctaacattg  10380
attcaggtac agggagaagg cgcatgagac tcgaaagcgt agctaaattt cattcgccaa  10440
aaagcccgat gatgagcgac tcaccacggg ccacggcttc tgactctctt tccggtactg  10500
atgtgatggc tgctatgggg atggcgcaat cacaagccgg attcggtatg ctgcattct  10560
gcggtaagca cgaactcagc cagaacgaca acaaaaggc tatcaactat ctgatgcaat  10620
ttgcacacaa ggtatcgggg aaataccgtg gtgtggcata tcttgaagga atactaagg  10680
caaaggtact gcaagtgctc gcaacattcg cttatgcgga ttattgccgt agtgccgcga  10740
cgccgggggc aagatgcaga gattgccatg gtacaggccg tgcggttgat attgccaaaa  10800
cagagctgtg ggggagagtt gtcgagaaag agtgcggaag atgcaaaggc gtcggctatt  10860
caaggatgcc agcaagcgca gcatatcgcg ctgtgacgat gctaatccca aaccttaccc  10920
aacccacctg gtcacgcact gttaagccgc tgtatgacgc tctggtggtg caatgccaca  10980
aagaagagtc aatcgcagac aacattttga atgcggtcac acgttagcag catgattgcc  11040
acggatggca acatattaac ggcatgatat tgacttattg aataaaattg gtaaatttg  11100
actcaacgat gggttaattc gctcgttgtg gtagtgagat gaaagaggc ggcgcttact  11160
```

```
accgattccg cctagttggt cacttcgacg tatcgtctgg aactccaacc atcgcaggca   11220
gagaggtctg caaaatgcaa tcccgaaaca gttcgcaggt aatagttaga gcctgcataa   11280
cggtttcggg attttttata tctgcacaac aggtaagagc attgagtcga taatcgtgaa   11340
gagtcggcga gcctggttag ccagtgctct ttccgttgtg ctgaattaag cgaataccgg   11400
aagcagaacc ggatcaccaa atgcgtacag gcgtcatcgc cgcccagcaa cagcacaacc   11460
caaactgagc cgtagccact gtctgtcctg aattccatgc ttgaacccgc ctatgcgcgg   11520
gttttctttt gtgcgcttgc aggccagctt gggatcagca gcctgacgga tgcggtgtcc   11580
ggcgacagcc tgactgccca ggaggcactc gcgacgctgg cattatccgg tgatgatgac   11640
ggaccacgac aggcccgcag ttatcaggtc atgaacggca tcgccgtgct gccggtgtcc   11700
ggcacgctgg tcagccggac gcgggcgctg cagccgtact cggggatgac cggttacaac   11760
ggcattatcg cccgtctgca acaggctgcc agcgatccga tggtggacgg cattctgctc   11820
gatatggaca cgcccggcgg gatggtggcg ggggcatttg actgcgctga catcatcgcc   11880
cgtgtgcgtg acataaaacc ggtatgggcg cttgccaacg acatgaactg cagtgcaggt   11940
cagttgcttg ccagtgccgc ctcccggcgt ctggtcacgc agaccgcccg gacaggctcc   12000
atcggcgtca tgatggctca cagtaattac ggtgctgcgc tggagaaaca gggtgtggaa   12060
atcacgctga tttacagcgg cagccataag gtggatggca accccctacag ccatcttccg   12120 gatgacgtcc gggagacact gcagtccggg atggacgcaa cccgccagat gtttgcgcag   12180
aaggtgtcgg catataccgg cctgtccgtg caggttgtgc tggataccga ggctgcagtg   12240
tacagcggtc aggaggccat tgatgccgga ctggctgatg aacttgttaa cagcaccgat   12300
gcgatcaccg tcatgcgtga tgcactggat gcacgtaaat cccgtctctc aggagggcga   12360
atgaccaaag agactcaatc aacaactgtt tcagccactg cttcgcaggc tgacgttact   12420
gacgtggtgc cagcgacgga gggcgagaac gccagcgcgg cgcagccgga cgtgaacgcg   12480
cagatcaccg cagcggttgc ggcagaaaac agccgcatta tggggatact caactgtgag   12540
gaggctcacg gacgcgaaga acaggcacgc gtgctggcag aaaccccccgg tatgaccgtg   12600 aaaacggccc gccgcattct ggccgcagca ccacagagtg cacaggcgcg cagtgacact   12660
gcgctggatc gtctgatgca gggggcaccg gcaccgctgg ctgcaggtaa cccggcatct   12720
gatgccgtta acgatttgct gaacacacca gtgtaaggga tgtttatgac gagcaaagaa   12780
acctttaccc attaccagcc gcagggcaac agtgacccgg ctcataccgc aaccgcgccc   12840
ggcggattga gtgcgaaagc gcctgcaatg accccgctga tgctgacac ctccagccgt   12900 aagctggttg cgtgggatgg caccaccgac ggtgctgccg ttggcattct tgcggttgct   12960
gctgaccaga ccagcaccac gctgacgttc tacaagtccg gcacgttccg ttatgaggat   13020
gtgctctggc cggaggctgc cagcgacgag acgaaaaaac ggaccgcgtt tgccggaacg   13080
gcaatcagca tcgtttaact ttacccttca tcactaaagg ccgcctgtgc ggcttttttt   13140
acgggatttt tttatgtcga tgtacacaac cgcccaactg ctggcggcaa atgagcagaa   13200
atttaagttt gatccgctgt ttctgcgtct cttttttccgt gagagctatc ccttcaccac   13260
ggagaaagtc tatctctcac aaattccggg actggtaaac atggcgctgt acgtttcgcc   13320 gattgttttcc ggtgaggtta tccgttcccg tggcggctcc acctctgaat ttacgccggg   13380
atatgtcaag ccgaagcatg aagtgaatcc gcagatgacc ctgcgtcgcc tgccggatga   13440
agatccgcag aatctggcgg acccggctta ccgccgccgt cgcatcatca tgcagaacat   13500
gcgtgacgaa gagctggcca ttgctcaggt cgaagagatg caggcagttt ctgccgtgct   13560
```

```
taagggcaaa tacaccatga ccggtgaagc cttcgatccg gttgaggtgg atatgggccg   13620
cagtgaggag aataacatca cgcagtccgg cggcacggag tggagcaagc gtgacaagtc   13680
cacgtatgac ccgaccgacg atatcgaagc ctacgcgctg aacgccagcg gtgtggtgaa   13740
tatcatcgtg ttcgatccga aaggctgggc gctgttccgt tccttcaaag ccgtcaagga   13800
gaagctggat acccgtcgtg gctctaattc cgagctggag acagcggtga aagacctggg   13860
caaagcggtg tcctataagg ggatgtatgg cgatgtggcc atcgtcgtgt attccggaca   13920
gtacgtggaa aacggcgtca aaagaacttc ctgccggac aacacgatgg tgctggggaa   13980
cactcaggca cgcggtctgc gcacctatgg ctgcattcag gatgcggacg cacagcgcga   14040
aggcattaac gcctctgccc gttacccgaa aaactgggtg accaccggcg atccggcgcg   14100
tgagttcacc atgattcagt cagcaccgct gatgctgctg gctgaccctg atgagttcgt   14160
gtccgtacaa ctggcgtaat catggccctt cggggccatt gtttctctgt ggaggagtcc   14220
atgacgaaag atgaactgat tgcccgtctc cgctcgctgg gtgaacaact gaaccgtgat   14280
gtcagcctga cggggacgaa agaagaactg gcgctccgtg tggcagagct gaaagaggag   14340
cttgatgaca cggatgaaac tgccggtcag gacaccctc tcagccggga aaatgtgctg   14400
accggacatg aaaatgaggt gggatcagcg cagccggata ccgtgattct ggatacgtct   14460
gaactggtca cggtcgtggc actggtgaag ctgcatactg atgcacttca cgccacgcgg   14520
gatgaacctg tggcatttgt gctgccggga acggcgtttc gtgtctctgc cggtgtggca   14580
gccgaaatga cagagcgcgg cctggccaga atgcaataac gggaggcgct gtggctgatt   14640
tcgataacct gttcgatgct gccattgccc gcgccgatga acgatacgc gggtacatgg   14700 gaacgtcagc caccattaca tccggtgagc agtcaggtgc ggtgatacgt ggtgttttg    14760 atgaccctga aaatatcagc tatgccggac agggcgtgcg cgttgaaggc tccagcccgt   14820
ccctgtttgt ccggactgat gaggtgcggc agctgcggcg tggagacacg ctgaccatcg   14880
gtgaggaaaa tttctgggta gatcgggttt cgccggatga tggcggaagt tgtcatctct   14940
ggcttggacg gggcgtaccg cctgccgtta accgtcgccg ctgaaagggg gatgtatggc   15000
cataaaaggt cttgagcagg ccgttgaaaa cctcagccgt atcagcaaaa cggcggtgcc   15060
tggtgccgcc gcaatggcca ttaaccgcgt tgcttcatcc gcgatatcgc agtcggcgtc   15120
acaggttgcc cgtgagacaa aggtacgccg gaaactggta aggaaagggc caggctgaa    15180 aagggccacg gtcaaaaatc cgcaggccag aatcaaagtt aaccgggggg atttgcccgt   15240
aatcaagctg gtaatgcgc gggttgtcct ttcgcgccgc aggcgtcgta aaaggggca    15300 gcgttcatcc ctgaaaggtg gcggcagcgt gcttgtggtg ggtaaccgtc gtattcccgg   15360
ccgtttattt cagcaactga aaaatggccg gtggcatgtc atgcagcgtg tggctgggaa   15420
aaaccgttac cccattgatg tggtgaaaat cccgatggcg gtgccgctga ccacggcgtt   15480
taaacaaaat attgagcgga tacgcgtgaa acgtcttccg aaaagagctgg gctatgcgct   15540 gcagcatcaa ctgaggatgg taataaagcg atgaaacata ctgaactccg tgcagccgta   15600
ctggatgcac tggagaagca tgacaccggg gcgacgttt ttgatggtcg ccccgctgtt    15660
tttgatgagg cggattttcc ggcagttgcc gtttatctca ccggcgctga atacacgggc   15720
gaagagctgg acagcgatac ctggcaggcg gagctgcata tcgaagtttt cctgcctgct   15780
caggtgccga ttcagagct ggatgcgtgg atggagtccc ggatttatcc ggtgatgagc    15840
gatatcccgg cactgtcaga tttgatcacc agtatggtgg ccagcggcta tgactaccgg   15900
```

```
cgcgacgatg atgcgggctt gtggagttca gccgatctga cttatgtcat tacctatgaa   15960
atgtgaggac gctatgcctg taccaaatcc tacaatgccg gtgaaaggtg ccgggaccac   16020
cctgtgggtt tataagggga gcggtgaccc ttacgcgaat ccgctttcag acgttgactg   16080
gtcgcgtctg gcaaaagtta aagacctgac gcccggcgaa ctgaccgctg agtcctatga   16140
cgacagctat ctcgatgatg aagatgcaga ctggactgcg accgggcagg ggcagaaatc   16200
tgccggagat accagcttca cgctggcgtg gatgcccgga gagcaggggc agcaggcgct   16260
gctggcgtgg tttaatgaag gcgatacccg tgcctataaa atccgcttcc cgaacggcac   16320
ggtcgatgtg ttccgtggct gggtcagcag tatcggtaag gcggtgacgg cgaaggaagt   16380
gatcacccgc acggtgaaag tcaccaatgt gggacgtccg tcgatggcag aagatcgcag   16440
cacggtaaca gcggcaaccg gcatgaccgt gacgcctgcc agcacctcgg tggtgaaagg   16500
gcagagcacc acgctgaccg tggccttcca gccggagggc gtaaccgaca agagctttcg   16560
tgcggtgtct gcggataaaa caaaagccac cgtgtcggtc agtggtatga ccatcaccgt   16620
gaacggcgtt gctgcaggca aggtcaacat tccggttgta tccggtaatg gtgagtttgc   16680
tgcggttgca gaaattaccg tcaccgccag ttaatccgga gagtcagcga tgttcctgaa   16740
aaccgaatca tttgaacata cggtgtgac cgtcacgctt tctgaactgt cagccctgca   16800
gcgcattgag catctcgccc tgatgaaacg gcaggcagaa caggcggagt cagacagcaa   16860
ccggaagttt actgtggaag acgccatcag aaccggcgcg tttctggtgg cgatgtccct   16920
gtggcataac catccgcaga agacgcagat gccgtccatg aatgaagccg ttaaacagat   16980
tgagcaggaa gtgcttacca cctggcccac ggaggcaatt tctcatgctg aaaacgtggt   17040
gtaccggctg tctggtatgt atgagtttgt ggtgaataat gcccctgaac agacagagga   17100
cgccgggccc gcagagcctg tttctgcggg aaagtgttcg acggtgagct gagttttgcc   17160
ctgaaactgg cgcgtgagat ggggcgaccc gactggcgtg ccatgcttgc cgggatgtca   17220
tccacggagt atgccgactg gcaccgcttt tacagtaccc attattttca tgatgttctg   17280
ctggatatgc acttttccgg gctgacgtac accgtgctca gcctgttttt cagcgatccg   17340
gatatgcatc cgctggattt cagtctgctg aaccggcgcg aggctgacga agagcctgaa   17400
gatgatgtgc tgatgcagaa agcggcaggg cttgccggag gtgtccgctt tggcccggac   17460
gggaatgaag ttatccccgc ttccccggat gtggcggaca tgacggagga tgacgtaatg   17520
ctgatgacag tatcagaagg gatcgcagga ggagtccggt atggctgaac cggtaggcga   17580
tctggtcgtt gatttgagtc tggatgcggc cagatttgac gagcagatgg ccagagtcag   17640
gcgtcatttt tctggtacgg aaagtgatgc gaaaaaaaca gcggcagtcg ttgaacagtc   17700
gctgagccga caggcgctgg ctgcacagaa agcggggatt tccgtcgggc agtataaagc   17760
cgccatgcgt atgctgcctg cacagttcac cgacgtggcc acgcagcttg caggcgggca   17820
aagtccgtgg ctgatcctgc tgcaacaggg ggggcaggtg aaggactcct tcggcgggat   17880
gatccccatg ttcagggggc ttgccggtgc gatcaccctg ccgatggtgg ggccacctc   17940 gctggcggtg gcgaccggtg cgctggcgta tgcctggtat cagggcaact caaccctgtc   18000
cgatttcaac aaaacgctgg tccttttccgg caatcaggcg ggactgacgg cagatcgtat   18060
gctggtcctg tccagagccg ggcaggcggc agggctgacg tttaaccaga ccagcgagtc   18120
actcagcgca ctggttaagg cgggggtaag cggtgaggct cagattgcgt ccatcagcca   18180
gagtgtggcc cgtttctcct ctgcatccgg cgtggaggtg gacaaggtcg ctgaagcctt   18240
cgggaagctg accacagacc cgacgtcggg gctgacggcg atggctcgcc agttccataa   18300
```

```
cgtgtcggcg gagcagattg cgtatgttgc tcagttgcag cgttccggcg atgaagccgg   18360
ggcattgcag gcggcgaacg aggccgcaac gaaagggttt gatgaccaga cccgccgcct   18420
gaaagagaac atgggcacgc tggagacctg gcagacagg actgcgcggg cattcaaatc    18480
catgtgggat gcggtgctgg atattggtcg tcctgatacc gcgcaggaga tgctgattaa   18540
ggcagaggct gcgtataaga aagcagacga catctggaat ctgcgcaagg atgattattt   18600
tgttaacgat gaagcgcggg cgcgttactg ggatgatcgt gaaaaggccc gtcttgcgct   18660
tgaagccgcc cgaaagaagg ctgagcagca gactcaacag gacaaaaatg cgcagcagca   18720
gagcgatacc gaagcgtcac ggctgaaata taccgaagag gcgcagaagg cttacgaacg   18780
gctgcagacg ccgctggaga aatataccgc ccgtcaggaa gaactgaaca aggcactgaa   18840
agacgggaaa atcctgcagg cggattacaa cacgctgatg gcggcggcga aaaggatta    18900 tgaagcgacg ctgaaaaagc cgaaacagtc cagcgtgaag gtgtctgcgg gcgatcgtca   18960
ggaagacagt gctcatgctg ccctgctgac gcttcaggca gaactccgga cgctggagaa   19020
gcatgccgga gcaaatgaga aaatcagcca gcagcgccgg gatttgtgga aggcggagag   19080
tcagttcgcg gtactggagg aggcggcgca acgtcgccag ctgtctgcac aggagaaatc   19140
cctgctggcg cataaagatg agacgctgga gtacaaacgc cagctggctg cacttggcga   19200
caaggttacg tatcaggagc gcctgaacgc gctggcgcag caggcggata aattcgcaca   19260
gcagcaacgg gcaaaacggg ccgccattga tgcgaaaagc cgggggctga ctgaccggca   19320
ggcagaacgg gaagccacgg aacagcgcct gaaggaacag tatggcgata tccgctggc    19380 gctgaataac gtcatgtcag agcagaaaaa gacctgggcg gctgaagacc agcttcgcgg   19440
gaactggatg gcaggcctga agtccggctg gagtgagtgg gaagagagcg ccacggacag   19500
tatgtcgcag gtaaaaagtg cagccacgca gacctttgat ggtattgcac agaatatggc   19560
ggcgatgctg accggcagtg agcagaactg gcgcagcttc acccgttccg tgctgtccat   19620
gatgacagaa attctgctta agcaggcaat ggtggggatt gtcggagta tcggcagcgc    19680 cattggcggg gctgttggtg gcggcgcatc cgcgtcaggc ggtacagcca ttcaggccgc   19740
tgcggcgaaa ttccattttg caaccggagg atttacggga accggcggca aatatgagcc   19800
agcggggatt gttcaccgtg gtgagtttgt cttcacgaag gaggcaacca gccggattgg   19860 cgtgggaat ctttaccggc tgatgcgcgg ctatgccacc ggcggttatg tcggtacacc    19920
gggcagcatg gcagacagcc ggtcgcaggc gtccgggacg tttgagcaga taaccatgt    19980 ggtgattaac aacgacggca cgaacgggca gataggtccg gctgctctga aggcggtgta   20040
tgacatggcc cgcaagggtg cccgtgatga aattcagaca cagatgcgtg atggtggcct   20100
gttctccgga ggtggacgat gaagaccttc gctggaaagt gaaacccgg tatggatgtg    20160 gcttcggtcc cttctgtaag aaaggtgcgc tttggtgatg ctattctca gcgagcgcct    20220 gccgggctga atgccaacct gaaaacgtac agcgtgacgc tttctgtccc ccgtgaggag   20280
gccacggtac tggagtcgtt tctggaagag cacgggggct ggaaatcctt tctgtggacg   20340
ccgccttatg agtggcggca gataaaggtg acctgcgcaa atggtcgtc gcgggtcagt    20400 atgctgcgtg ttgagttcag cgcagagttt gaacaggtgg tgaactgatg caggatatcc   20460
ggcaggaaac actgaatgaa tgcacccgtg cggagcagtc ggccagcgtg gtgctctggg   20520
aaatcgacct gacagaggtc ggtggagaac gttatttttt ctgtaatgag cagaacgaaa   20580
aaggtgagcc ggtcacctgg caggggcgac agtatcagcc gtatcccatt caggggagcg   20640
```

```
gttttgaact gaatggcaaa ggcaccagta cgcgccccac gctgacggtt tctaacctgt   20700
acggtatggt caccgggatg gcggaagata tgcagagtct ggtcggcgga acggtggtcc   20760
ggcgtaaggt ttacgcccgt tttctggatg cggtgaactt cgtcaacgga aacagttacg   20820
ccgatccgga gcaggaggtg atcagccgct ggcgcattga gcagtgcagc gaactgagcg   20880
cggtgagtgc ctcctttgta ctgtccacgc cgacggaaac ggatggcgct gttttttccgg  20940 gacgtatcat gctggccaac acctgcacct ggacctatcg cggtgacgag tgcggttata   21000
gcggtccggc tgtcgcggat gaatatgacc agccaacgtc cgatatcacg aaggataaat   21060
gcagcaaatg cctgagcggt tgtaagttcc gcaataacgt cggcaacttt ggcggcttcc   21120
tttccattaa caaactttcg cagtaaatcc catgacacag acagaatcag cgattctggc   21180
gcacgcccgg cgatgtgcgc cagcggagtc gtgcggcttc gtggtaagca cgccggaggg   21240
ggaaagatat ttcccctgcg tgaatatctc cggtgagccg gaggcgtatt ccgtatgtc    21300 gccggaagac tggctgcagg cagaaatgca gggtgagatt gtggcgctgg tccacagcca   21360
ccccggtggt ctgcccctggc tgagtgaggc cgaccggcgg ctgcaggtgc agagtgattt   21420
gccgtggtgg ctggtctgcc ggggggacgat tcataagttc cgctgtgtgc cgcatctcac   21480
cgggcggcgc tttgagcacg gtgtgacgga ctgttacaca ctgttccggg atgcttatca   21540
tctggcgggg attgagatgc cggactttca tcgtgaggat gactggtggc gtaacggcca   21600
gaatctctat ctggataatc tggaggcgac ggggctgtat caggtgccgt tgtcagcggc   21660
acagccgggc gatgtgctgc tgtgctgttt tggttcatca gtgccgaatc acgccgcaat   21720
ttactgcggc gacggcgagc tgctgcacca tattcctgaa caactgagca acgagagag   21780 gtacaccgac aaatggcagc gacgcacaca ctccctctgg cgtcaccggg catggcgcgc   21840
atctgccttt acgggatttt acaacgattt ggtcgccgca tcgaccttcg tgtgaaaacg   21900
ggggctgaag ccatccgggc actggccaca cagctcccgg cgtttcgtca gaaactgagc   21960
gacggctggt atcaggtacg gattgccggg cgggacgtca gcacgtccgg gttaacggcg   22020
cagttacatg agactctgcc tgatggcgct gtaattcata ttgttcccag agtcgccggg   22080
gccaagtcag gtggcgtatt ccagattgtc ctggggggctg ccgccattgc cggatcattc   22140
tttaccgccg gagccacccct tgcagcatgg ggggcagcca ttggggccgg tggtatgacc   22200
ggcatcctgt ttctctcgg tgccagtatg gtgctcggtg gtgtggcgca gatgctggca   22260
ccgaaagcca gaactccccg tatacagaca acggataacg gtaagcagaa cacctatttc   22320
tcctcactgg ataacatggt tgcccagggc aatgttctgc ctgttctgta cggggaaatg   22380
cgcgtggggt cacgcgtggt ttctcaggag atcagcacgg cagacgaagg ggacggtggt   22440
caggttgtgg tgattggtcg ctgatgcaaa atgttttatg tgaaaccgcc tgcgggcggt   22500
tttgtcattt atggagcgtg aggaatgggt aaaggaagca gtaagggggca taccccgcgc   22560 gaagcgaagg acaacctgaa gtccacgcag ttgctgagtg tgatcgatgc catcagcgaa   22620
gggccgattg aaggtccggt ggatggctta aaaagcgtgc tgctgaacag tacgccggtg   22680
ctggacactg aggggaatac caacatatcc ggtgtcacgg tggtgttccg ggctggtgag   22740
caggagcaga ctccgccgga gggatttgaa tcctccggct ccgagacggt gctgggtacg   22800
gaagtgaaat atgacacgcc gatcaccccgc accattacgt ctgcaaacat cgaccgtctg   22860
cgctttacct tcggtgtaca ggcactggtg gaaaccacct caaagggtga caggaatccg   22920
tcggaagtcc gcctgctggt tcagatacaa cgtaacggtg gctgggtgac ggaaaaagac   22980
atcaccatta agggcaaaac cacctcgcag tatctggcct cggtggtgat gggtaacctg   23040
```

```
ccgccgcgcc cgtttaatat ccggatgcgc aggatgacgc cggacagcac cacagaccag   23100
ctgcagaaca aaacgctctg gtcgtcatac actgaaatca tcgatgtgaa acagtgctac   23160
ccgaacacgg cactggtcgg cgtgcaggtg gactcggagc agttcggcag ccagcaggtg   23220
agccgtaatt atcatctgcg cgggcgtatt ctgcaggtgc cgtcgaacta aacccgcag    23280 acgcggcaat acagcggtat ctgggacgga acgtttaaac cggcatacag caacaacatg   23340
gcctggtgtc tgtgggatat gctgacccat ccgcgctacg gcatgggaa acgtcttggt    23400 gcggcggatg tggataaatg ggcgctgtat gtcatcggcc agtactgcga ccagtcagtg   23460
ccggacggct ttggcggcac ggagccgcgc atcacctgta atgcgtacct gaccacacag   23520
cgtaaggcgt gggatgtgct cagcgatttc tgctcggcga tgcgctgtat gccggtatgg   23580
aacgggcaga cgctgacgtt cgtgcaggac cgaccgtcgg ataagacgtg gacctataac   23640
cgcagtaatg tggtgatgcc ggatgatggc gcgccgttcc gctacagctt cagcgccctg   23700
aaggaccgcc ataatgccgt tgaggtgaac tggattgacc cgaacaacgg ctgggagacg   23760
gcgacagagc ttgttgaaga tacgcaggcc attgcccgtt acggtcgtaa tgttacgaag   23820
atggatgcct ttggctgtac cagccggggg caggcacacc gcgccgggct gtggctgatt   23880
aaaacagaac tgctggaaac gcagaccgtg gatttcagcg tcggcgcaga agggcttcgc   23940
catgtaccgg gcgatgttat tgaaatctgc gatgatgact atgccggtat cagcaccggt   24000
ggtcgtgtgc tggcggtgaa cagccagacc cggacgctga cgctcgaccg tgaaatcacg   24060
ctgccatcct ccggtaccgc gctgataagc ctggttgacg gaagtggcaa tccggtcagc   24120
gtggaggttc agtccgtcac cgacggcgtg aaggtaaaag tgagccgtgt tcctgacggt   24180
gttgctgaat acagcgtatg ggagctgaag ctgccgacgc tgcgccagcg actgttccgc   24240
tgcgtgagta tccgtgagaa cgacgacggc acgtatgcca tcaccgccgt gcagcatgtg   24300
ccggaaaaag aggccatcgt ggataacggg gcgcactttg acggcgaaca gagtggcacg   24360
gtgaatggtg tcacgccgcc agcggtgcag cacctgaccg cagaagtcac tgcagacagc   24420
ggggaatatc aggtgctggc gcgatgggac acaccgaagg tggtgaaggg cgtgagtttc   24480
ctgctccgtc tgaccgtaac agcggacgac ggcagtgagc ggctggtcag cacggcccgg   24540
acgacggaaa ccacataccg cttcacgcaa ctggcgctgg ggaactacag gctgacagtc   24600
cgggcggtaa atgcgtgggg gcagcagggc gatccggcgt cggtatcgtt ccggattgcc   24660
gcaccggcag caccgtcgag gattgagctg acgccgggct attttcagat aaccgccacg   24720
ccgcatcttg ccgtttatga cccgacggta cagtttgagt tctggttctc ggaaaagcag   24780
attgcggata tcagacaggt tgaaaccagc acgcgttatc ttggtacggc gctgtactgg   24840
atagccgcca gtatcaatat caaaccgggc catgattatt acttttatat ccgcagtgtg   24900
aacaccgttg gcaaatcggc attcgtggag gccgtcggtc gggcgagcga tgatgcggaa   24960
ggttacctgg atttttttcaa aggcaagata accgaatccc atctcggcaa ggagctgctg   25020
gaaaaagtcg agctgacgga ggataacgcc agcagactgg aggagttttc gaaagagtgg   25080
aaggatgcca gtgataagtg gaatgccatg tgggctgtca aaattgagca gaccaaagac   25140
ggcaaacatt atgtcgcggg tattggcctc agcatggagg acacggagga aggcaaactg   25200
agccagtttc tggttgccgc caatcgtatc gcatttattg acccggcaaa cgggaatgaa   25260
acgccgatgt ttgtggcgca gggcaaccag atattcatga cgacgtgtt cctgaagcgc    25320 ctgacggccc ccaccattac cagcggcggc aatcctccgg ccttttccct gacaccggac   25380
```

```
ggaaagctga ccgctaaaaa tgcggatatc agtggcagtg tgaatgcgaa ctccgggacg   25440
ctcagtaatg tgacgatagc tgaaaactgt acgataaacg gtacgctgag ggcggaaaaa   25500
atcgtcgggg acattgtaaa ggcggcgagc gcggcttttc cgcgccagcg tgaaagcagt   25560
gtggactggc cgtcaggtac ccgtactgtc accgtgaccg atgaccatcc ttttgatcgc   25620
cagatagtgg tgcttccgct gacgtttcgc ggaagtaagc gtactgtcag cggcaggaca   25680
acgtattcga tgtgttatct gaaagtactg atgaacggtg cggtgattta tgatggcgcg   25740
gcgaacgagg cggtacaggt gttctcccgt attgttgaca tgccagcggg tcggggaaac   25800
gtgatcctga cgttcacgct tacgtccaca cggcattcgg cagatattcc gccgtatacg   25860
tttgccagcg atgtgcaggt tatggtgatt aagaaacagg cgctgggcat cagcgtggtc   25920
tgagtgtgtt acagaggttc gtccgggaac gggcgtttta ttataaaaca gtgagaggtg   25980
aacgatgcgt aatgtgtgta ttgccgttgc tgtctttgcc gcacttgcgg tgacagtcac   26040
tccggcccgt gcggaaggtg gacatggtac gtttacggtg ggctattttc aagtgaaacc   26100
gggtacattg ccgtcgttgt cgggcgggga taccggtgtg agtcatctga aagggattaa   26160
cgtgaagtac cgttatgagc tgacggacag tgtgggggtg atggcttccc tggggttcgc   26220
cgcgtcgaaa aagagcagca cagtgatgac cggggaggat acgtttcact atgagagcct   26280
gcgtggacgt tatgtgagcg tgatggccgg accggtttta caaatcagta agcaggtcag   26340
tgcgtacgcc atgccggag tggctcacag tcggtggtcc ggcagtacaa tggattaccg   26400
taagacggaa atcactcccg ggtatatgaa agagacgacc actgccaggg acgaaagtgc   26460
aatgcggcat acctcagtgg cgtggagtgc aggtatacag attaatccgg cagcgtccgt   26520
cgttgttgat attgcttatg aaggctccgg cagtggcgac tggcgtactg acggattcat   26580
cgttggggtc ggttataaat tctgattagc caggtaacac agtgttatga cagcccgccg   26640
gaaccggtgg gcttttttgt ggggtgaata tggcagtaaa gatttcagga gtcctgaaag   26700
acggcacagg aaaaccggta cagaactgca ccattcagct gaaagccaga cgtaacagca   26760
ccacggtggt ggtgaacacg gtgggctcag agaatccgga tgaagccggg cgttacagca   26820
tggatgtgga gtacggtcag tacagtgtca tcctgcaggt tgacggtttt ccaccatcgc   26880
acgccgggac catcaccgtg tatgaagatt cacaaccggg gacgctgaat gattttctct   26940
gtgccatgac ggaggatgat gcccggccgg aggtgctgcg tcgtcttgaa ctgatggtgg   27000
aagaggtggc gcgtaacgcg tccgtggtgg cacagagtac ggcagacgcg aagaaatcag   27060
ccggcgatgc cagtgcatca gctgctcagg tcgcggccct tgtgactgat gcaactgact   27120
cagcacgcgc cgccagcacg tccgccggac aggctgcatc gtcagctcag gaagcgtcct   27180
ccggcgcaga agcggcatca gcaaaggcca ctgaagcgga aaaagtgcc gcagccgcag   27240 agtcctcaaa aaacgcggcg gccaccagtg ccggtgcggc gaaaacgtca gaaacgaatg   27300
ctgcagcgtc acaacaatca gccgccacgt ctgcctccac cgcggccacg aaagcgtcag   27360
aggccgccac ttcagcacga gatgcggtgg cctcaaaaga ggcagcaaaa tcatcagaaa   27420
cgaacgcatc atcaagtgcc ggtcgtgcag cttcctcggc aacggcggca gaaaattctg   27480
ccagggcggc aaaaacgtcc gagacgaatg ccaggtcatc tgaaacagca gcggaacgga   27540
gcgcctctgc cgcggcagac gcaaaaacag cggcggcggg gagtgcgtca acggcatcca   27600
cgaaggcgac agaggctgcg ggaagtgcgg tatcagcatc gcagagcaaa agtgcggcag   27660
aagcggcggc aatacgtgca gaaaattcgg caaaacgtgc agaagatata gcttcagctg   27720
tcgcgcttga ggatgcggac acaacgagaa aggggatagt gcagctcagc agtgcaacca   27780
```

```
acagcacgtc tgaaacgctt gctgcaacgc caaaggcggt taaggtggta atggatgaaa   27840
cgaacagaaa agcccactgg acagtccggc actgaccgga acgccaacag caccaaccgc   27900
gctcagggga acaaacaata cccagattgc gaacaccgct tttgtactgg ccgcgattgc   27960
agatgttatc gacgcgtcac ctgacgcact gaatacgctg aatgaactgg ccgcagcgct   28020
cgggaatgat ccagattttg ctaccaccat gactaacgcg cttgcgggta acaaccgaa    28080 gaatgcgaca ctgacggcgc tggcagggct ttccacggcg aaaataaat taccgtattt    28140 tgcggaaaat gatgccgcca gcctgactga actgactcag gttggcaggg atattctggc   28200
aaaaaattcc gttgcagatg ttcttgaata ccttggggcc ggtgagaatt ctaagcggag   28260
atcgcctagt gattttaaac tattgctggc agcattcttg agtccaatat aaaagtattg   28320 tgtaccttt gctgggtcag gttgttcttt aggaggagta aaaggatcaa atgcactaaa    28380
cgaaactgaa acaagcgatc gaaaatatcc ctttgggatt cttgactcga taagtctatt   28440
attttcagag aaaaaatatt cattgttttc tgggttggtg attgcaccaa tcattccatt   28500
caaaattgtt gttttaccac acccattccg cccgataaaa gcatgaatgt tcgtgctggg   28560
catagaatta accgtcacct caaaaggtat agttaaatca ctgaatccgg gagcactttt   28620
tctattaaat gaaaagtgga aatctgacaa ttctggcaaa ccatttaaca cacgtgcgaa   28680
ctgtccatga atttctgaaa gagttacccc tctaagtaat gaggtgttaa ggacgctttc   28740
attttcaatg tcggctaatc gatttggcca tactactaaa tcctgaatag ctttaagaag   28800
gttatgttta aaaccatcgc ttaatttgct gagattaaca tagtagtcaa tgctttcacc   28860
taaggaaaaa aacatttcag ggagttgact gaattttta tctattaatg aataagtgct   28920
tacttcttct ttttgaccta caaaaccaat tttaacattt ccgatatcgc attttcacc    28980 atgctcatca aagacagtaa gataaaacat tgtaacaaag gaatagtcat tccaaccatc   29040
tgctcgtagg aatgccttat ttttttctac tgcaggaata tacccgcctc tttcaataac   29100
actaaactcc aacatatagt aacccttaat tttattaaaa taaccgcaat ttatttggcg   29160
gcaacacagg atctctcttt taagttactc tctattacat acgttttcca tctaaaaatt   29220
agtagtattg aacttaacgg ggcatcgtat tgtagttttc catatttagc tttctgcttc   29280
cttttggata acccactgtt attcatgttg catggtgcac tgtttatacc aacgatatag   29340
tctattaatg catatatagt atcgccgaac gattagctct tcaggcttct gaagaagcgt   29400
ttcaagtact aataagccga tagatagcca cggacttcgt agccattttt cataagtgtt   29460
aacttccgct cctcgctcat aacagacatt cactacagtt atggcggaaa ggtatgcatg   29520
ctgggtgtgg ggaagtcgtg aaagaaaaga agtcagctgc gtcgtttgac atcactgcta   29580
tcttcttact ggttatgcag gtcgtagtgg gtggcacaca aagctttgca ctggattgcg   29640
aggctttgtg cttctctgga gtgcgacagg tttgatgaca aaaattagc gcaagaagac    29700 aaaaatcacc ttgcgctaat gctctgttac aggtcactaa taccatctaa gtagttgatt   29760
catagtgact gcatatgttg tgttttacag tattatgtag tctgttttt atgcaaaatc    29820 taatttaata tattgatatt tatatcattt tacgtttctc gttca                   29865
```

<210> SEQ ID NO 15
<211> LENGTH: 2628
<212> TYPE: DNA
<213> ORGANISM: Escherichia coli
<220> FEATURE:
<223> OTHER INFORMATION: gyra gene

<400> SEQUENCE: 15

```
atgagcgacc ttgcgagaga aattacaccg gtcaacattg aggaagagct gaagagctcc    60
tatctggatt atgcgatgtc ggtcattgtt ggccgtgcgc tgccagatgt ccgagatggc   120
ctgaagccgg tacaccgtcg cgtactttac gccatgaacg tactaggcaa tgactggaac   180
aaagcctata aaaaatctgc ccgtgtcgtt ggtgacgtaa tcggtaaata ccatccccat   240
ggtgactcgg cggtctatga cacgatcgtc cgcatggcgc agccattctc gctgcgttat   300
atgctggtag acggtcaggg taacttcggt tctatcgacg gcgactctgc ggcggcaatg   360
cgttatacgg aaatccgtct ggcgaaaatt gcccatgaac tgatggccga tctcgaaaaa   420
gagacggtcg atttcgttga taactatgac ggcacggaaa aaattccgga cgtcatgcca   480
accaaaattc ctaacctgct ggtgaacggt tcttccggta tcgccgtagg tatggcaacc   540
aacatcccgc cgcacaacct gacggaagtc atcaacggtt gtctggcgta tattgatgat   600
gaagacatca gcattgaagg gctgatggaa cacatcccgg ggccggactt cccgacggcg   660
gcaatcatta acggtcgtcg cggtattgaa gaagcttacc gtaccggtcg cggcaaggtg   720
tatatccgcg ctcgcgcaga agtggaagtt gacgccaaaa ccggtcgtga accattatc    780
gtccacgaaa ttccgtatca ggtaaacaaa gcgcgcctga tcgagaagat tgcggaactg   840
gtaaaagaaa aacgcgtgga aggcatcagc gcgctgcgtg acgagtctga caaagacggt   900
atgcgcatcg tgattgaagt gaaacgcgat gcggtcggtg aagttgtgct caacaacctc   960
tactcccaga cccagttgca ggtttctttc ggtatcaaca tggtggcatt gcaccatggt  1020
cagccgaaga tcatgaacct gaaagacatc atcgcggcgt tgttcgtca ccgccgtgaa   1080
gtggtgaccc gtcgtactat tttcgaactg cgtaaagctc gcgatcgtgc tcatatcctt  1140
gaagcattag ccgtggcgct ggcgaacatc gacccgatca tcgaactgat ccgtcatgcg  1200
ccgacgcctg cagaagcgaa aactgcgctg gttgctaatc cgtggcagct gggcaacgtt  1260
gccgcgatgc tcgaacgtgc tggcgacgat gctgcgcgtc cggaatggct ggagccagag  1320
ttcggcgtgc gtgatggtct gtactacctg accgaacagc aagctcaggc gattctggat  1380
ctgcgttttgc agaaactgac cggtcttgag cacgaaaaac tgctcgacga atacaaagag  1440
ctgctggatc agatcgcgga actgttgcgt attcttggta gcgccgatcg tctgatggaa  1500
gtgatccgtg aagagctgga gctggttcgt gaacagttcg gtgacaaacg tcgtactgaa  1560
atcaccgcca acagcgcaga catcaacctg gaagatctga tcacccagga agatgtggtc  1620
gtgacgctct ctcaccaggg ctacgttaag tatcagccgc tttctgaata cgaagcgcag  1680
cgtcgtggcg ggaaaggtaa atctgccgca cgtattaaag aagaagactt tatcgaccga  1740
ctgctggtgg cgaacactca cgaccatatt ctgtgcttct ccagccgtgg tcgcgtctat  1800
tcgatgaaag tttatcagtt gccggaagcc actcgtggcg cgcgcggtcg tccgatcgtc  1860
aacctgctgc cgctggagca ggacgaacgt atcactgcga tcctgccagt gaccgagttt  1920
gaagaaggcg tgaaagtctt catggcgacc gctaacggta ccgtgaagaa aactgtcctc  1980
accgagttca ccgtctgcg taccgccggt aaagtggcga tcaaactggt tgacggcgat  2040
gagctgatcg gcgttgacct gaccagcggc gaagacgaag taatgctgtt ctccgctgaa  2100
ggtaaagtgg tgcgctttaa agagtcttct gtccgtgcga tgggctgcaa caccaccggt  2160
gttcgcggta ttcgcttagg tgaaggcgat aaagtcgtct ctctgatcgt gcctcgtggc  2220
gatgcgcaa tcctcaccgc aacgcaaaac ggttacggta acgtaccgc agtgcggaa     2280
tacccaacca gtcgcgtgc gacgaaaggg gttatctcca tcaaggttac cgaacgtaac  2340
```

```
ggtttagttg ttggcgcggt acaggtagat gactgcgacc agatcatgat gatcaccgat    2400
gccggtacgc tggtacgtac tcgcgtttcg gaaatcagca tcgtgggccg taacacccag    2460
ggcgtgatcc tcatccgtac tgcggaagat gaaaacgtag tgggtctgca acgtgttgct    2520
gaaccggttg acgaggaaga tctggatacc atcgacggca gtgccgcgga aggggacgat    2580
gaaatcgctc cggaagtgga cgttgacgac gagccagaag aagaataa                 2628

<210> SEQ ID NO 16
<211> LENGTH: 768
<212> TYPE: DNA
<213> ORGANISM: Artificial Sequence
<220> FEATURE:
<223> OTHER INFORMATION: Insertion sequence

<400> SEQUENCE: 16
ggtaatgact ccaacttatt gatagtgttt tatgttcaga taatgcccga tgactttgtc     60
atgcagctcc accgattttg agaacgacag cgacttccgt cccagccgtg ccaggtgctg    120
cctcagattc aggttatgcc gctcaattcg ctgcgtatat cgcttgctga ttacgtgcag    180
cttccccttc aggcgggatt catacagcgg ccagccatcc gtcatccata tcaccacgtc    240
aaagggtgac agcaggctca taagacgccc agcgtcgcc atagtgcgtt caccgaatac    300
gtgcgcaaca accgtcttcc ggagactgtc atacgcgtaa acagccagc ctggcgcga    360 tttagccccg acatagcccc actgttcgtc catttccgcg cagacgatga cgtcactgcc    420
cggctgtatg cgcgaggtta ccgactgcgg cctgagtttt ttaagtgacg taaaatcgtg    480
ttgaggccaa cgcccataat gcgggctgtt gcccggcatc aacgccatt catggccata    540 tcaatgattt tctggtgcgt accgggttga aagcggtgt aagtgaactg cagttgccat    600
gttttacggc agtgagagca gagatagcgc tgatgtccgg cggtgctttt gccgttacgc    660
accaccccgt cagtagctga acaggaggga cagctgatag aaacagaagc cactggagca    720
cctcaaaaac accatcatac actaaatcag taagttggca gcatcacc                 768

<210> SEQ ID NO 17
<211> LENGTH: 21
<212> TYPE: PRT
<213> ORGANISM: Artificial Sequence
<220> FEATURE:
<223> OTHER INFORMATION: OmpA signal peptide

<400> SEQUENCE: 17

Met Lys Lys Thr Ala Ile Ala Ile Ala Val Ala Leu Ala Gly Phe Ala
1               5                   10                  15

Thr Val Ala Gln Ala
            20

<210> SEQ ID NO 18
<211> LENGTH: 20
<212> TYPE: PRT
<213> ORGANISM: Artificial Sequence
<220> FEATURE:
<223> OTHER INFORMATION: DsbA signal peptide

<400> SEQUENCE: 18

Met Lys Lys Ile Trp Leu Ala Leu Ala Gly Leu Val Leu Ala Phe Ser
1               5                   10                  15

Ala Ser Ala Ala
            20
```

```
<210> SEQ ID NO 19
<211> LENGTH: 21
<212> TYPE: PRT
<213> ORGANISM: Artificial Sequence
<220> FEATURE:
<223> OTHER INFORMATION: PhoA signal peptide

<400> SEQUENCE: 19

Met Lys Gln Ser Thr Ile Ala Leu Ala Leu Leu Pro Leu Leu Phe Thr
1               5                   10                  15

Pro Val Thr Lys Ala
            20
```